US 11,660,196 B2

(12) United States Patent
Bhattacharyya et al.

(10) Patent No.: US 11,660,196 B2
(45) Date of Patent: May 30, 2023

(54) 3-D PRINTING OF BONE GRAFTS

(71) Applicant: Warsaw Orthopedic, Inc., Warsaw, IN (US)

(72) Inventors: Subhabrata Bhattacharyya, Metuchen, NJ (US); David R. Kaes, Toms River, NJ (US); Guobao Wei, Milltown, NJ (US); Anil Mistry, Edison, NJ (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 15/493,236

(22) Filed: Apr. 21, 2017

(65) Prior Publication Data
US 2018/0303616 A1    Oct. 25, 2018

(51) Int. Cl.
*A61F 2/28*    (2006.01)
*B33Y 10/00*    (2015.01)
(Continued)

(52) U.S. Cl.
CPC ............ *A61F 2/30942* (2013.01); *A61F 2/28* (2013.01); *A61F 2/2846* (2013.01); *A61F 2/4455* (2013.01); *A61L 27/18* (2013.01); *A61L 27/3608* (2013.01); *A61L 27/54* (2013.01); *A61L 27/56* (2013.01); *A61L 27/58* (2013.01); *B29C 64/171* (2017.08); *B29C 64/386* (2017.08); *B33Y 10/00* (2014.12); *B33Y 50/02* (2014.12); *B33Y 70/10* (2020.01);
(Continued)

(58) Field of Classification Search
CPC ............. A61F 2002/30962; A61F 2002/30985
See application file for complete search history.

(56) References Cited

U.S. PATENT DOCUMENTS

| 4,430,760 A | 2/1984 | Smestad |
| 5,204,055 A | 4/1993 | Sachs et al. |

(Continued)

FOREIGN PATENT DOCUMENTS

| CN | 102149859 A | 8/2011 |
| WO | 2004016438 A1 | 2/2004 |

(Continued)

OTHER PUBLICATIONS

U.S. Appl. No. 62/116,351, filed Feb. 13, 2015.*
(Continued)

*Primary Examiner* — David H Willse
(74) *Attorney, Agent, or Firm* — Sorell, Lenna & Schmidt, LLP

(57) ABSTRACT

Computer implemented methods of producing a bone graft are provided. These methods include obtaining a 3-D image of an intended bone graft site; generating a 3-D digital model of the bone graft based on the 3-D image of the intended bone graft site, the 3-D digital model of the bone graft being configured to fit within a 3-D digital model of the intended bone graft site; storing the 3-D digital model on a database coupled to a processor, the processor having instructions for retrieving the stored 3-D digital model of the bone graft and for combining a carrier material with, in or on a bone material based on the stored 3-D digital model and for instructing a 3-D printer to produce the bone graft. A layered 3-D printed bone graft prepared by the computer implemented method is also provided.

11 Claims, 13 Drawing Sheets

(51) Int. Cl.
  *B33Y 50/02* (2015.01)
  *B33Y 80/00* (2015.01)
  *B33Y 70/10* (2020.01)
  *B29C 64/171* (2017.01)
  *A61F 2/30* (2006.01)
  *A61L 27/58* (2006.01)
  *A61L 27/36* (2006.01)
  *A61L 27/54* (2006.01)
  *A61F 2/44* (2006.01)
  *A61L 27/18* (2006.01)
  *A61L 27/56* (2006.01)
  *B29C 64/386* (2017.01)
  *A61L 27/04* (2006.01)
  *B29L 31/00* (2006.01)

(52) U.S. Cl.
  CPC ....... *B33Y 80/00* (2014.12); *A61F 2002/2835* (2013.01); *A61F 2002/30062* (2013.01); *A61F 2002/30677* (2013.01); *A61F 2002/30948* (2013.01); *A61F 2002/30952* (2013.01); *A61F 2002/30962* (2013.01); *A61F 2002/30971* (2013.01); *A61F 2002/30985* (2013.01); *A61F 2310/00041* (2013.01); *A61F 2310/00359* (2013.01); *A61L 27/04* (2013.01); *A61L 2400/06* (2013.01); *A61L 2430/02* (2013.01); *B29K 2995/0056* (2013.01); *B29L 2031/7532* (2013.01)

(56) References Cited

U.S. PATENT DOCUMENTS

| | | |
|---|---|---|
| 6,440,444 B2 | 8/2002 | Boyce et al. |
| 7,832,457 B2 | 11/2010 | Calnan et al. |
| 8,778,252 B2 | 7/2014 | Mackie et al. |
| 8,798,780 B2 | 8/2014 | Menchik et al. |
| 9,034,356 B2 | 5/2015 | Shimp et al. |
| 9,101,475 B2 | 8/2015 | Wei et al. |
| 9,220,598 B2 | 12/2015 | Betz et al. |
| 9,277,850 B2 | 3/2016 | Kubach |
| 9,333,082 B2 | 5/2016 | Wei et al. |
| 9,364,583 B2 | 6/2016 | McKay |
| 9,492,278 B2 | 11/2016 | Wei et al. |
| 2001/0035886 A1 | 11/2001 | Bradshaw et al. |
| 2005/0021142 A1 | 1/2005 | Ganz et al. |
| 2005/0208168 A1 | 9/2005 | Hickerson et al. |
| 2008/0042321 A1 | 2/2008 | Russell et al. |
| 2008/0262616 A1 | 10/2008 | McKay |
| 2010/0049322 A1 | 2/2010 | McKay |
| 2011/0054408 A1 | 3/2011 | Wei et al. |
| 2012/0165969 A1 | 6/2012 | Elsey |
| 2012/0271418 A1* | 10/2012 | Hollister ............... A61F 2/2803 623/17.11 |
| 2014/0191439 A1 | 7/2014 | Davis |
| 2014/0212471 A1 | 7/2014 | Drapeau et al. |
| 2014/0236299 A1 | 8/2014 | Roeder et al. |
| 2015/0054195 A1 | 2/2015 | Greyf |
| 2015/0096266 A1 | 4/2015 | Divine et al. |
| 2015/0259548 A1 | 9/2015 | Wang et al. |
| 2015/0374450 A1* | 12/2015 | Mansfield ............. B29C 64/165 264/219 |
| 2016/0038207 A1 | 2/2016 | Wei et al. |
| 2016/0250038 A1 | 9/2016 | Wei et al. |
| 2016/0318247 A1* | 11/2016 | Schlachter ............. B33Y 10/00 |
| 2017/0024501 A1* | 1/2017 | Greyf .................... B29C 64/165 |
| 2018/0021140 A1* | 1/2018 | Angelini ............. C12N 5/0062 623/23.72 |

FOREIGN PATENT DOCUMENTS

| | | |
|---|---|---|
| WO | 2014092651 A1 | 6/2014 |
| WO | 2015167520 A1 | 11/2015 |
| WO | 2016085907 A1 | 6/2016 |

OTHER PUBLICATIONS

Extended European Search Report issued by the European Patent Office dated May 29, 2020 and issued in European Patent Application No. 20156067.9 in the name of Warsaw Orthopedic, Inc.

Office Action issued by the European Patent Office dated Mar. 16, 2021 and issued in European Patent Application No. 20156067.9 in the name of Warsaw Orthopedic, Inc.

First Office Action issued by the Chinese Patent Office dated May 21, 2021 in corresponding Chinese Patent Appl. No. 20180360497.6 (English translation provided).

Office Action/Communication pursuant to Article 94(3) EPC dated Sep. 7, 2022 by the European Patent Office in corresponding European patent application No. 20156067.9.

\* cited by examiner

3-D PRINTING OF BONE GRAFTS

BACKGROUND

Three-dimensional (3-D) printing is an additive printing process used to make three-dimensional solid objects from a digital model. 3-D printing techniques are considered additive processes because they involve the application of successive layers of material.

3-D printing technology is applied in various industries for manufacturing and planning. For example, the automotive, aerospace and consumer goods industries use 3-D printing to create prototypes of parts and products. 3-D printing has also been used in the architectural industry for printing structural models. The applications of 3-D printing in private and government defense have grown rapidly as well.

Traditional 3-D printing allows an object to be created by depositing a material over a flat fabrication platform one layer at a time. Once a first layer is deposited, a second layer is deposited on top of the first layer. The process is repeated as necessary to create a multi-laminate solid object. However, 3-D printing does not allow for continuous extrusion to create an object. 3-D printing also has not been widely appreciated for use in manufacturing bone grafts used to repair bone defects.

Bone defects may be caused by a number of different factors including, but not limited to, trauma, pathological disease or surgical intervention. Because bone provides both stability and protection to an organism, these defects can be problematic. In order to address these defects, compositions that contain both natural and synthetic materials have been developed. These compositions may, depending upon the materials contained within them, be used to repair tissues and to impart desirable biological and/or mechanical properties to the bone defect.

Among the known bone repair materials and bone void fillers is autologous cancellous bone. This type of bone has the advantage of being both osteoinductive and non-immunogenic. Unfortunately, this type of bone is not available under all circumstances. Moreover, donor site morbidity and trauma add to the limitations of autologous cancellous bone.

Generally, bone tissue regeneration is achieved by filling a bone repair site with a bone graft. Over time, the bone graft is incorporated by the host and new bone remodels the bone graft. In order to place the bone graft, it is common to use a monolithic bone graft or to form an osteoimplant comprising particulated bone in a carrier. The carrier material is thus chosen to be biocompatible, to be resorbable, and to have release characteristics such that the bone graft is accessible. Ordinarily, the formed implant, whether monolithic or particulated and in a carrier, is substantially solid at the time of implantation and, thus does not conform to the implant site. Further, the implant is substantially complete at the time of implantation and thus provides little ability for customization, for example, by the addition or subtraction of autograft material.

Regarding bone grafts, allograft bone is a reasonable bone graft substitute for autologous bone. It is readily available from cadavers and avoids the surgical complications and patient morbidity associated with harvesting autologous bone. Allograft bone is essentially a load-bearing matrix comprising cross-linked collagen, hydroxyapatite, and osteoinductive bone morphogenetic proteins (BMPs). Human allograft bone is widely used in orthopedic surgery.

Demineralized bone matrix (DBM) is also considered allograft bone, namely, bone from other humans, that has had the inorganic, mineral material removed, leaving behind the organic collagen matrix and BMPs that induce bone formation. DBM is conducive to osteoinduction, but lacks the load bearing strength.

Traditional methods of 3D printing do not allow for producing a custom-made bone graft by controlling the bone material with, in or on the carrier material during manufacturing to form the desired osteoconductive, osteoinductive and/or osteogenic bone graft that aids in influx and efflux of cells to repair the damaged bone. Thus, there is a need for a computer implemented method of producing a bone graft having the desired osteoconductive, osteoinductive and/or osteogenic properties that can be customized to the intended bone graft site.

SUMMARY

The present disclosure provides a system and method of producing custom bone grafts that are made of a biocompatible material that can be used as ink in a 3-D printer to produce bone grafts of any desired shape. The present disclosure also provides, in some embodiments, a system and method of producing custom bone grafts that contain a bioactive agent that can be released at the bone graft site.

In some embodiments, there is a computer implemented method for producing a bone graft. The method comprises obtaining a 3-D image of an intended bone graft site; generating a 3-D digital model of the bone graft based on the 3-D image of the intended bone graft site, the 3-D digital model of the bone graft being configured to fit within the bone graft site. The method also includes storing the 3-D digital model on a database coupled to a processor, the processor having instructions for retrieving the stored 3-D digital model of the bone graft and for combining a carrier material (e.g., biodegradable polymer) with, in or on a bone material based on the stored 3-D digital model and for instructing a 3-D printer to produce the bone graft.

According to other aspects, provided is a layered 3-D printed bone graft. In some embodiments, the layered bone graft comprises a first layer of biodegradable polymer, a second layer of bone material disposed on the first layer of biodegradable polymer, a third layer of biodegradable polymer disposed on the second layer, each layer repeating until a 3-D printer has completed the layered bone graft. In other embodiments, the layered 3-D printed bone graft comprises a first layer of biodegradable polymer mixed with bone material; a second layer of biodegradable polymer mixed with bone material, the second layer disposed on the first layer, a third layer of biodegradable polymer mixed with bone material, the third layer disposed on the second layer, each layer repeating until the 3-D printer has completed the layered bone graft.

According to other embodiments, provided is a method of treating a bone defect in a patient in need thereof. In certain aspects, the method comprises administering a layered 3-D printed bone graft to the bone defect, wherein the layered 3-D printed bone graft comprises a first layer of biodegradable polymer, a second layer of bone material disposed on the first layer of biodegradable polymer, a third layer of biodegradable polymer disposed on the second layer, each layer repeating until a 3-D printer has completed the layered bone graft. In other aspects, the method of treatment includes administering a layered 3-D printed bone graft which comprises a first layer of biodegradable polymer mixed with bone material, a second layer of biodegradable polymer mixed with bone material, the second layer disposed on the first layer, a third layer of biodegradable polymer mixed with bone material, the third layer disposed on the second layer, each layer repeating until the 3-D printer has completed the layered bone graft.

While multiple embodiments are disclosed, still other embodiments of the present application will become apparent to those skilled in the art from the following detailed description, which is to be read in connection with the accompanying drawings. As will be apparent, the present disclosure is capable of modifications in various obvious aspects, all without departing from the spirit and scope of the present disclosure. Accordingly, the detailed description is to be regarded as illustrative in nature and not restrictive.

BRIEF DESCRIPTION OF THE FIGURES

In part, other aspects, features, benefits and advantages of the embodiments will be apparent regarding the following description, appended claims and accompanying drawings.

Figure 1:
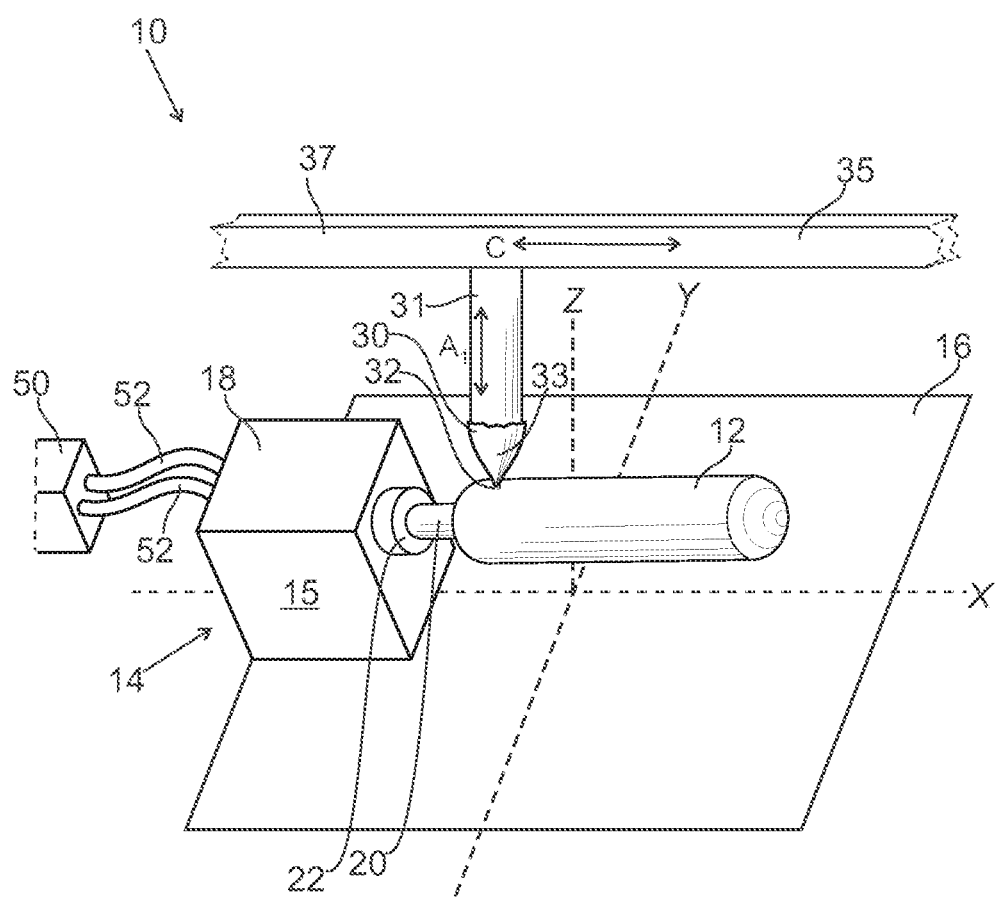
FIG. 1 illustrates a perspective view of an exemplary 3-D printing device according to an aspect of the present application. The 3-D printing device includes a rotatable printing surface to facilitate continuous extrusion of a predetermined hollow implant.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

Definitions

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Similarly, when values are expressed as approximations, by use of the antecedent "about," it will be understood that the particular value forms another embodiment that is +/−10% of the recited value. Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value.

Notwithstanding that the numerical ranges and parameters setting forth the broad scope of this application are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, for example, 5.5 to 10.

Allograft, as used herein, refers to a graft of tissue obtained from a donor of the same species as, but with a different genetic make-up from the recipient, as a tissue transplant between two humans.

The bone graft can have a bioactive agent disposed in or on the bone graft. Bioactive agent or bioactive compound is used herein to refer to a compound or entity that alters, inhibits, activates, or otherwise affects biological or chemical events. For example, bioactive agents may include, but are not limited to, osteogenic or chondrogenic proteins or peptides, anti-AIDS substances, anti-cancer substances, antibiotics, immunosuppressants, anti-viral substances, enzyme inhibitors, hormones, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and antiadhesion molecules, vasodilating agents, inhibitors of DNA, RNA or protein synthesis, anti-hypertensives, analgesics, anti-pyretics, steroidal and non-steroidal anti-inflammatory agents, clonidine, a statin, bone morphogenetic protein, anti-angiogenic factors, angiogenic factors, anti-secretory factors, anticoagulants and/or antithrombotic agents, local anesthetics, prostaglandins, anti-depressants, anti-psychotic substances, anti-emetics, and imaging agents. In certain embodiments, the bioactive agent is a drug. Bioactive agents further include RNAs, such as siRNA, and osteoclast stimulating factors. In some embodiments, the bioactive agent may be a factor that stops, removes, or reduces the activity of bone growth inhibitors. In some embodiments, the bioactive agent is a growth factor, cytokine, extracellular matrix molecule or a fragment or derivative thereof, for example, a cell attachment sequence such as RGD.

Biocompatible, as used herein, is intended to describe materials that, upon administration in vivo, do not induce undesirable long-term effects.

Biodegradable includes compounds or components that will degrade over time by the action of enzymes, by hydrolytic action and/or by other similar mechanisms in the human body. In various embodiments, "biodegradable" includes that components can break down or degrade within the body to non-toxic components as cells (e.g., bone cells) infiltrate the components and allow repair of the defect. By "biodegradable" it is meant that the compounds or components will erode or degrade over time due, at least in part, to contact with substances found in the surrounding tissue, fluids or by cellular action. By "bioabsorbable" it is meant that the compounds or components will be broken down and absorbed within the human body, for example, by a cell or tissue. "Biocompatible" means that the compounds or components will not cause substantial tissue irritation or necrosis at the target tissue site and/or will not be carcinogenic.

Bone, as used herein, refers to bone that is cortical, cancellous or cortico-cancellous of autogenous, allogenic, xenogenic, or transgenic origin.

Bone graft, as used herein, refers to any implant prepared in accordance with the embodiments described herein and therefore may include expressions such as bone material and bone membrane.

Demineralized, as used herein, refers to any material generated by removing mineral material from tissue, for example, bone tissue. In certain embodiments, demineralized bone material may be added to the bone graft. The demineralized bone material described herein include preparations containing less than 5%, 4%, 3%, 2% or 1% calcium by weight. Partially demineralized bone (for example, preparations with greater than 5% calcium by weight but containing less than 100% of the original starting amount of calcium) is also considered within the scope of the disclosure. In some embodiments, partially demineralized bone contains preparations with greater than 5%, 10%, 15%, 20%, 25%, 30%, 35%, 40%, 45%, 50%, 55%, 60%, 65%, 70%, 75%, 80%, 85%, 90%, 95%, 96%, 97%, 98% or 99% of the original starting amount of calcium. In some embodiments, demineralized bone has less than 95% of its original mineral content. In some embodiments, demineralized bone has less than 95%, 90%, 85%, 80%, 75%, 70%, 65%, 60%, 55%, 50%, 45%, 40%, 35%, 30%, 25%, 20%, 15%, 10%, or 5% of its original mineral content. Demineralized is intended to encompass such expressions as "substantially demineralized," "partially demineralized," "superficially demineralized," and "fully demineralized." In some embodiments, part or the entire surface of the bone can be demineralized. For example, part or the entire surface of the bone material can be demineralized to a depth of from about 100 to about 5000 microns, or about 150 microns to about 1000 microns. In some embodiments, part or all of the surface of the bone material can be demineralized to a depth of from about 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2650, 2700, 2750, 2800, 2850, 2900, 2950, 3000, 3050, 3100, 3150, 3200, 3250, 3300, 3350, 3400, 3450, 3500, 3550, 3600, 3650, 3700, 3750, 3800, 3850, 3900, 3950, 4000, 4050, 4100, 4150, 4200, 4250, 4300, 4350, 4400, 4450, 4500, 4550, 4600, 4650, 4700, 4750, 4800, 4850, 4900, 4950 to about 5000 microns. If desired, the bone void filler can comprise demineralized material.

Partially demineralized bone is intended to refer to preparations with greater than 5% calcium by weight but containing less than 100% of the original starting amount of calcium. In some embodiments, partially demineralized bone comprises 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 and/or 99% of the original starting amount of calcium.

In some embodiments, the demineralized bone may be surface demineralized from about 1-99%. In some embodiments, the demineralized bone is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 and/or 99% surface demineralized. In various embodiments, the demineralized bone may be surface demineralized from about 15-25%. In some embodiments, the demineralized bone is 15, 16, 17, 18, 19, 20, 21, 22, 23, 24 and/or 25% surface demineralized.

Demineralized bone matrix (DBM), as used herein, refers to any material generated by removing mineral material from bone tissue. In some embodiments, the DBM compositions as used herein include preparations containing less than 5% calcium and, in some embodiments, less than 1% calcium by weight. In some embodiments, the DBM compositions include preparations that contain less than 5, 4, 3, 2 and/or 1% calcium by weight. In other embodiments, the DBM compositions comprise partially demineralized bone (for example, preparations with greater than 5% calcium by weight but containing less than 100% of the original starting amount of calcium).

Osteoconductive, as used herein, refers to the ability of a substance to serve as a template or substance along which bone may grow.

Osteogenic, as used herein, refers to materials containing living cells capable of differentiation into bone tissue.

Osteoinductive, as used herein, refers to the quality of being able to recruit cells from the host that have the potential to stimulate new bone formation. Any material that can induce the formation of ectopic bone in the soft tissue of an animal is considered osteoinductive. For example, most osteoinductive materials induce bone formation in athymic rats when assayed according to the method of Edwards et al., "Osteoinduction of Human Demineralized Bone: Characterization in a Rat Model," Clinical Orthopaedics & Rel. Res., 357:219-228, December 1998, incorporated herein by reference.

Osteoimplant is used herein in its broadest sense and is not intended to be limited to any particular shapes, sizes, configurations, compositions, or applications. Osteoimplant refers to any device or material for implantation that aids or augments bone formation or healing. An osteoimplant may include any material, such as allograft, xenograft, or synthetic material, used to promote or support bone healing. The osteoimplant may be homogeneous or heterogeneous. Osteoimplants are often applied at a bone defect site, e.g., one resulting from injury, defect brought about during the course of surgery, infection, malignancy, inflammation, or developmental malformation. Osteoimplants can be used in a variety of orthopedic, neurosurgical, dental, oral and maxillofacial surgical procedures such as the repair of simple and compound fractures and non-unions, external, and internal fixations, joint reconstructions such as arthrodesis, general arthroplasty, deficit filling, disectomy, laminectomy, anterior cervical and thoracic operations, or spinal fusions.

DBM preparations have been used for many years in orthopedic medicine to promote the formation of bone. For example, DBM has found use in the repair of fractures, in the fusion of vertebrae, in joint replacement surgery, and in treating bone destruction due to underlying disease such as a bone tumor. DBM has been shown to promote bone formation in vivo by osteoconductive and osteoinductive processes. The osteoinductive effect of implanted DBM compositions results from the presence of active growth factors present on the isolated collagen-based matrix. These factors include members of the TGF-R, IGF, and BMP protein families. Particular examples of osteoinductive factors include TGF-β, IGF-1 IGF-2, BMP-2, BMP-7, parathyroid hormone (PTH), and angiogenic factors. Other osteoinductive factors such as osteocalcin and osteopontin are also likely to be present in DBM preparations as well. There are also likely to be other unnamed or undiscovered osteoinductive factors present in DBM.

Superficially demineralized, as used herein, refers to bone-derived elements possessing at least about 90 weight percent of their original inorganic mineral content. In some embodiments, superficially demineralized contains at least about 90, 91, 92, 93, 94, 95, 96, 97, 98 and/or 99 weight percent of their original inorganic material. The expression "fully demineralized" as used herein refers to bone containing less than 8% of its original mineral context. In some embodiments, fully demineralized contains about less than 8, 7, 6, 5, 4, 3, 2 and/or 1% of its original mineral content.

The expression "average length to average thickness ratio" as applied to the DBM fibers of the present application means the ratio of the longest average dimension of the fiber (average length) to its shortest average dimension (average thickness). This is also referred to as the "aspect ratio" of the fiber.

Fibrous, as used herein, refers to bone elements whose average length to average thickness ratio or aspect ratio of the fiber is from about 50:1 to about 1000:1. In some embodiments, average length to average thickness ratio or aspect ratio of the fiber is from about 50:1, 75:1, 100:1, 125:1, 150:1, 175:1, 200:1, 225:1, 250:1, 275:1, 300:1, 325:1, 350:1, 375:1, 400:1, 425:1, 450:1, 475:1, 500:1, 525:1, 550:1, 575:1, 600:1, 625:1, 650:1, 675:1, 700:1, 725:1, 750:1, 775:1, 800:1, 825:1, 850:1, 875:1, 900:1, 925:1, 950:1, 975:1 and/or 1000:1. In overall appearance, the fibrous bone elements can be described as bone fibers, threads, narrow strips, or thin sheets. Often, where thin sheets are produced, their edges tend to curl up toward each other. The fibrous bone elements can be substantially linear in appearance or they can be coiled to resemble springs. In some embodiments, the bone fibers are of irregular shapes including, for example, linear, serpentine or curved shapes. The bone fibers are preferably demineralized however some of the original mineral content may be retained when desirable for a particular embodiment. In various embodiments, the bone fibers are mineralized. In some embodiments, the fibers are a combination of demineralized and mineralized.

Non-fibrous, as used herein, refers to elements that have an average width substantially larger than the average thickness of the fibrous bone element or aspect ratio of less than from about 50:1 to about 1000:1. The non-fibrous bone elements may be shaped in a substantially regular manner or specific configuration, for example, triangular prism, sphere, cube, cylinder and other regular shapes. By contrast, particles such as chips, shards, or powders possess irregular or random geometries. It should be understood that some variation in dimension will occur in the production of the elements of this application and elements demonstrating such variability in dimension are within the scope of this application and are intended to be understood herein as being within the boundaries established by the expressions "mostly irregular" and "mostly regular."

The bone implant devices and methods according to the present application increase DBM content in the device, increase the surface area of the DMB, and uniformly distribute the DBM throughout the delivery device to enhance bone growth when the delivery device is implanted at a bone defect. The bone implant devices and methods provided enhance bone growth by reducing the gaps that may exist between the DBM particles and reduce the distance for cells (for example, osteoclasts, osteoblasts, etc.) to travel throughout the device to allow those cells to receive an adequate osteoinductive signal as opposed to only along the surface of the device. In some embodiment, the device improves the fusion of adjacent interspinous processes.

The abbreviation "DLG" refers to poly(DL-lactide-co-glycolide).

The abbreviation "PDL" refers to poly(DL-lactide).

The abbreviation "PLG" refers to poly(L-lactide-co-glycolide).

The abbreviation "PCL" refers to polycaprolactone.

The abbreviation "DLCL" refers to poly(DL-lactide-co-caprolactone).

The abbreviation "LCL" refers to poly(L-lactide-co-caprolactone).

The abbreviation "PPG" refers to polyglycolide.

The abbreviation "PEG" refers to poly(ethylene glycol).

The abbreviation "PLGA" refers to poly(lactide-co-glycolide) also known as poly(lactic-co-glycolic acid), which are used interchangeably.

The abbreviation "PLA" refers to polylactide.

The abbreviation "PEA" refers to poly(ester)amides.

The abbreviation "POE" refers to poly(orthoester).

The terms "three-dimensional printing system," "three-dimensional printer," "printing," describe various solid freeform fabrication techniques for making three-dimensional articles or objects by selective deposition, jetting, fused deposition modeling, multijet modeling, and other additive manufacturing techniques now known in the art or that may be known in the future that use a build material or ink to fabricate three-dimensional objects.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

According to one aspect, there is a 3-D printed bone graft delivery device comprising: a porous biodegradable graft body for inducing bone growth at a surgical site, the porous biodegradable graft body having demineralized bone matrix (DBM) fibers disposed within the porous biodegradable body, and DBM powder disposed adjacent to, on or in the DBM fibers, wherein the porous biodegradable graft body facilitates transfer of cells into and out of the porous biodegradable graft body to induce bone growth at the surgical site.

3-D Printer Device

Provided is 3-D printing devices and methods of use for creating, in some embodiments, hollow structures such as mesh implants or bags. Also provided are 3-D printing devices including a rotatable printing surface to create such hollow structures or in some embodiments, solid structures. Further provided are devices and methods for 3-D printing onto a rotatable printing surface by continuous extrusion instead of stratified layers. Additionally, provided are devices and methods for creating structures having a meshed design that are strong, flexible, stretchable and biocompatible.

Turning now to FIGS. 1-7, provided is a 3-D printing device 10 for fabricating hollow structures, such as mesh bags 70 (e.g., mesh bags or mesh implants). 3-D printing is typically done in 2 dimensions, one layer at a time. Material is laid out on a flat surface and the three dimensional structures are built up one layer at a time, usually through a melting or sintering process. In some embodiments, a 3-D printer having a rotatable printing surface is provided to allow printing hollow structures, such as, for example, mesh bags. In some embodiments, a print head applies material to the print surface through continuous extrusion instead of stratified layers, as is done by traditional 3-D printing devices. In some embodiments, the 3-D printing device creates stronger structures and generates less waste than traditional 3-D printing devices.

As shown in FIG. 1, provided is 3-D printing device 10 for use in the fabrication of mesh bags 70. 3-D printing device 10 includes a table 14 having a base 16 and a printing surface 12. In some embodiments, printing surface 12 is mounted onto table 14 including base 16. Base 16 is configured for planar movement. In some embodiments, base 16 is movable in the x-y plane and is laterally movable in both the x axis and the y axis for precise positioning of printing surface 12. Printing surface 12, in some embodiments, is fixedly disposed with table 14 such that lateral movement of base 16 causes lateral movement of printing surface 12. Movement of base 16 allows for positioning of printing surface 12 relative to a print head 30 to facilitate depositing materials onto printing surface 12, as discussed herein.

Figure 2:
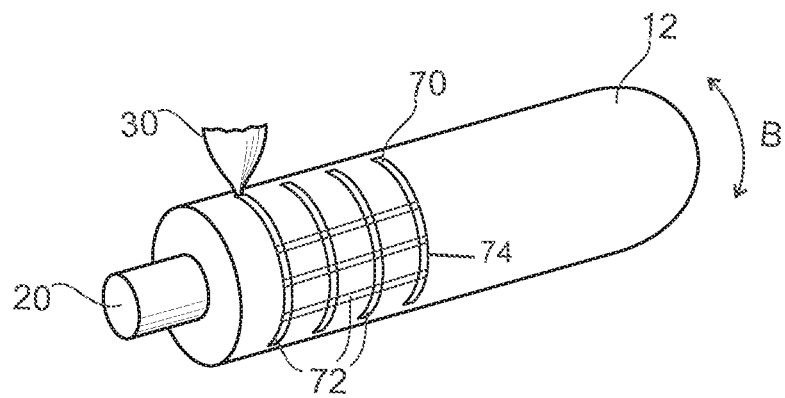
FIG. 2 illustrates a perspective view of components of an exemplary 3-D printing device according to an aspect of the present application. Specifically, shown is a printing surface having a cylindrical shape configured to create a cylindrically shaped hollow structure, such as a mesh bag. The printing surface is adjacent to and/or contacts a print head.
Figure 3:
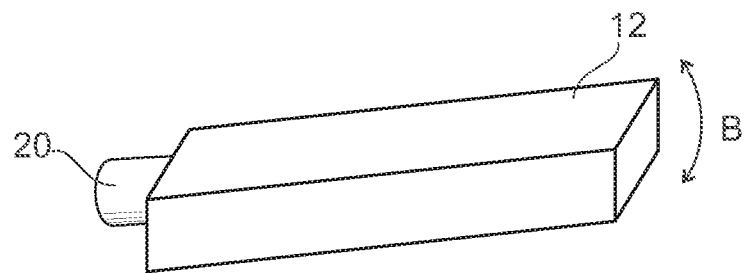
FIG. 3 illustrates a perspective view of components of an exemplary 3-D printing device according to an aspect of the present application. Specifically, shown is a printing surface having a rectangular cross-section configured to create a rectangular or square shaped hollow structure, such as a mesh bag.

Printing surface 12 is rotatable about an axis of rotation, as shown in FIGS. 2 and 3. In some embodiments, rotating printing surface 12 includes a cylindrical shape extending along a longitudinal axis, as shown in FIG. 2. The surface 12 can rotate along B. This allows printing of a round or circular implant with a hollow region as the implant takes on the shape of printing surface 12. The threads 72 may include bone material 74 (e.g., DBM particles, allograft tissue particles, cortical bone particles, etc.) uniformly disposed throughout the threads 72.

Figure 4:
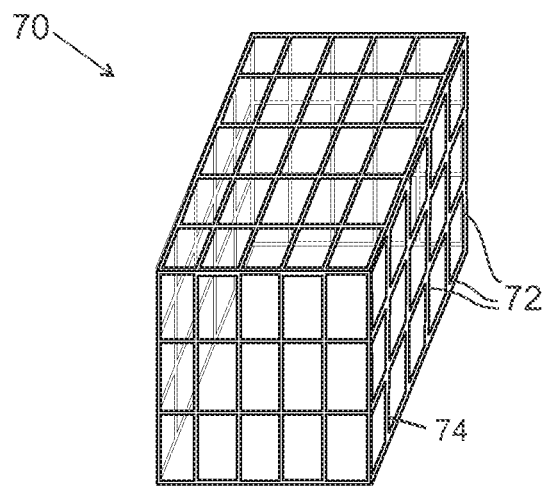
FIG. 4 illustrates a perspective view of an exemplary hollow structure created through use of a 3-D printing device, according to an aspect of the present application. The depicted hollow structure includes a rectangular cross-section.

In some embodiments, printing surface 12 includes other cross-sectional shapes, such as, for example, rectangular, oval, polygonal, irregular, undulating, or lobed. For example, as shown in FIG. 3, printing surface 12 may have a rectangular cross-section extending along a longitudinal axis. The surface 12 can rotate along B. This allows printing of a square or rectangular implant, as the print surface rotates, the implant will take the shape of the print surface. In alternative embodiments, printing surface 12 includes a uniform diameter and/or cross-section along its entire length. In other embodiments, printing surface 12 includes a changing diameter or cross-section along its length. For example, in some embodiments the diameter may increase from one end of printing surface 12 to the other. In some embodiments, the cross-section of printing surface 12 changes from one end to the other. For example, one end of printing surface 12 may have a circular cross-section while the opposite end may have a rectangular cross-section. The size and shape of printing surface 12 may be changed according to the specifications and needs of a particular medical procedure. In some embodiments, mesh bags 70 are printed onto printing surface 12 into which another object, such as for example, bone material (e.g. surface demineralized bone chips and fully demineralized bone fibers), can be placed inside a hollow region or compartment. The shape of printing surface 12 defines the shape of the hollow structure created. As shown in FIG. 2, the shape of mesh bag 70 created is cylindrical. As shown in FIG. 4, the shape of mesh bag 70 created is that of a hollowed out rectangular prism. The threads 72 may include bone material 74 (e.g., DBM particles, allograft tissue particles, cortical bone particles, etc.) uniformly disposed throughout the threads 72.

Printing surface 12 is rotatable about a rotation of axis defined by extension shaft 20, as discussed herein. In various embodiments, printing surface 12 is rotatable in either clockwise or counterclockwise directions. In various embodiments, printing surface 12 is rotatable in both clockwise and counterclockwise directions, as shown by arrow B in FIGS. 2 and 3. Printing surface 12 is configured to change direction of rotation multiple times throughout the course of fabrication of a hollow structure, such as, for example, mesh bag 70, as discussed herein. For example, printing surface 12 can rotate along a rotational axis 360 degrees clockwise and/or counterclockwise to print the implant.

In some embodiments, printing surface 12 is movable between an expanded configuration and a collapsed configuration. In some embodiments, a material 40 (which can be a biodegradable polymer) is deposited onto printing surface 12 while in the expanded configuration, and printing surface 12 is moved to the collapsed configuration to remove the printed hollow structure. Print head 30 can contact printing surface 12 or there can be a gap between printing surface 12 and print head 30 so that material 40 can be printed on printing surface 12.

In some embodiments, printing surface 12 is fixedly disposed with table 14 via a mounting bracket 18. Mounting bracket 18 may include covering 15 for protection. In some embodiments, mounting bracket 18 includes a motor to provide a rotational force to move printing surface 12. In some embodiments, mounting bracket 18 is connected to extension shaft 20. Printing surface 12 is connected to extension shaft 20 at a first end of printing surface 12. Extension shaft 20 defines an axis of rotation for printing surface 12 and is connected to mounting bracket 18 via a collet 22. In some embodiments, collet 22 is expandable to loosen the grip on extension shaft 20. This allows extension shaft 20 and printing surface 12 to be changed out for another printing surface 12 which may be sized and/or shaped differently to cater to the needs of a particular procedure.

In some embodiments, 3-D printing device 10 further includes print head 30, such as, for example, an applicator that is movable in a direction transverse to the plane of movement for base 16. In some embodiments, print head 30 is movable in the z axis, as shown by arrow $A_1$ in FIG. 1, to allow for different size fixtures, variable surface structures and to control the thickness of the extruded layer. Thus, print head 30 is movable to have an adjustable distance from printing surface 12. Additionally, print head 30 is movable to accommodate printing surfaces having various diameters or printing surfaces having gradient diameters. In some embodiments, print head 30 is also movable in the x and y planes parallel with the plane of movement for base 16. Thus, in some embodiments, print head 30 is movable in an opposite direction from the movement of printing surface 12 to facilitate faster printing. In some embodiments, print head 30 is suspended from a track 35. Track 35 provides a base of support for print head 30. In some embodiments, track 35 provides a predefined route of allowable movement for print head 30 in directions, shown as C. In some embodiments, track 35 is hollow to allow flow of material 40 to be delivered to printing surface 12, as described herein.

In some embodiments, printing surface 12 is treated with an adhesive material. The adhesive material may be textured or coated onto printing surface 12. The adhesive may be heat sensitive or heat activated such that printing surface 12 becomes adhesive to material 40 when printing surface 12 is heated, as discussed herein. An adhesive coating aids in preventing printed material 40 from falling off printing surface 12 during rotation. In some embodiments, the adhesive is deactivated through cooling. In some embodiments, the adhesive may be removed by placing printing surface 12 in a solvent to dissolve the adhesive material. Once the adhesive material is removed, a hollow structure printed to printing surface 12 may be removed.

Figure 6:
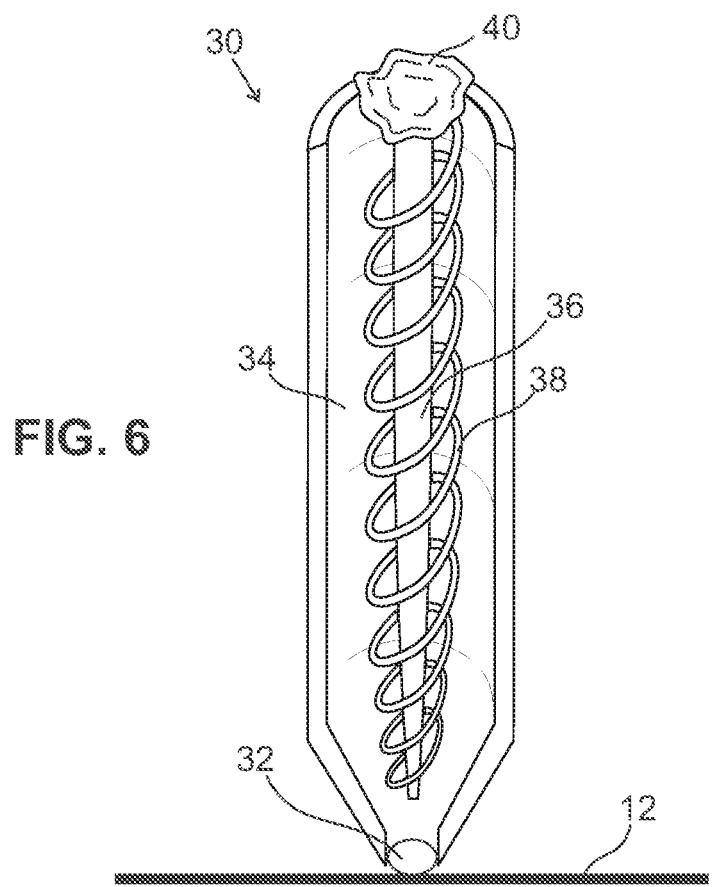
FIG. 6 illustrates a side view of components of an exemplary 3-D printing device according to an aspect of the present application. Specifically, shown is a print head which processes material to be extruded to the printing surface.

As shown in FIGS. 1 and 6, print head 30 includes a distal opening 32 through which material 40 is deposited on printing surface 12. A tube portion 31 of print head 30 includes a first diameter and extends distally to a head portion 33 having a second diameter. In some embodiments, the second diameter is smaller than the first diameter. In various embodiments, material 40 includes a biodegradable polymer. In some embodiments, material 40 comprises a bioerodible, a bioabsorbable, and/or a biodegradable biopolymer. Examples of suitable biopolymers include but are not limited to poly (alpha-hydroxy acids), poly (lactide-co-glycolide) (PLGA), polylactide (PLA), polyglycolide (PG), polyethylene glycol (PEG), conjugates of poly (alpha-hydroxy acids), poly(orthoester)s (POE), polyaspirins, polyphosphagens, collagen, starch, pre-gelatinized starch, hyaluronic acid, chitosans, gelatin, alginates, albumin, fibrin, vitamin E compounds, such as alpha tocopheryl acetate, d-alpha tocopheryl succinate, D,L-lactide, or L-lactide, caprolactone, dextrans, vinylpyrrolidone, polyvinyl alcohol (PVA), PVA-g-PLGA, PEGT-PBT copolymer (polyactive), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate) or combinations thereof. In various embodiments, material 40 comprises poly(lactide-co-glycolide) (PLGA), polylactide (PLA), polyglycolide (PGA), D-lactide, D,L-lactide, L-lactide, D,L-lactide-co-ε-caprolactone, D,L-lactide-co-glycolide-co-ε-caprolactone, L-lactide-co-ε-caprolactone or a combination thereof.

Print head 30 includes an inner lumen 34 and a central feed shaft 36 as illustrated in FIG. 6. Feed shaft 36 is configured to turn feed threads 38 to feed material 40 from the proximal end of print head 30 through opening 32. Material 40 is maintained in an external reservoir (not shown) and fed into lumen 34. In some embodiments, material 40 is driven into lumen 34 by gravity. In some embodiments material 40 is drawn into lumen 34 by turning feed shaft 36 and feed threads 38. In some embodiments, 3-D printing device includes multiple print heads 30, each configured to deposit material 40 onto printing surface 12.

In some embodiments, as illustrated in FIG. 1, 3-D printing device 10 further includes a temperature control unit 50 such as for example a heating or cooling unit connected to printing surface 12. In some embodiments, temperature control unit 50 includes a heating unit. In other embodiments, temperature control unit 50 includes a cooling unit. In some embodiments, temperature control unit 50 is used to heat printing surface 12 through electric heating elements underneath the surface of printing surface 12. Sufficient energy may be supplied through such electric conduits to provide a temperature on the surface of printing surface 12 to melt and bond material 40 applied from print head 30. In such an embodiment, as illustrated in FIG. 1, conduits 52 are electric heating conduits. In some embodiments, where material 40 comprises a highly viscous material, a heated printing surface 12 allows material 40 to flow. In other embodiments, material 40 is heated or cooled in a reservoir 37 to allow the desired flowability or viscosity of material 40 to make the implant.

In some embodiments, temperature control unit 50 comprises a cooling unit. The cooling unit is used to cool printing surface 12 through refrigerant supply and return lines underneath printing surface 12. In such an embodiment, the supply and return lines are conduits 52. The conduits 52 supply cooling fluid to printing surface 12 to cool and solidify hot material 40 extruded onto the surface. In alternative embodiments, reservoir 37 can have the cooling and heating unit to allow cooling or heating of material 40.

Figure 7:
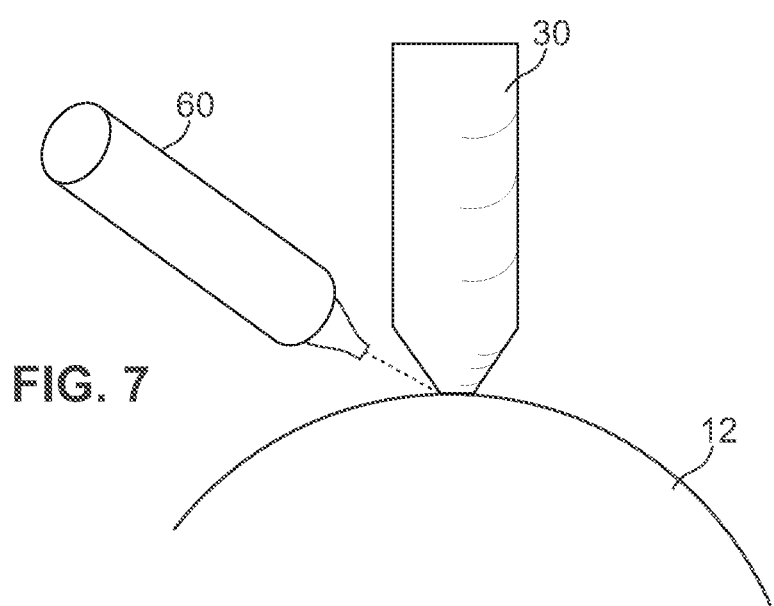
FIG. 7 illustrates a side view of components of an exemplary 3-D printing device according to an aspect of the present application. Specifically, shown is a radiation source, such as, for example, a laser mounted adjacent the print head to apply an energy to sinter or melt the material discharged from the print head.

According to some aspects, 3-D printing device 10 includes a radiation source configured to supply and transfer energy to at least a portion of the powder (e.g., polymer material) applied to the surface. In some embodiments, the radiation source is a laser 60 positioned adjacent print head 30. Laser 60 articulates such that the supplied beam can be focused on selected portions of printing surface 12. As shown in FIG. 7, laser 60 is configured to be used during or after print head 30 deposits material 40 (e.g., polymer material) onto printing surface 12. The beam of laser 60 is focused onto portions of material 40 on printing surface 12 to melt or sinter material 40 as desired. Once the printed hollow structure is complete, it may be removed from the residual powdered material 40 left on printing surface 12, or the residual powdered material 40 is brushed away. In some embodiments, laser 60 is focused at a point adjacent opening 32 to sinter material 40 as it is deposited onto printing surface 12. Such embodiments may facilitate the elimination of waste since the majority of material 40 extruded onto printing surface 12 is sintered.

In some embodiments, laser 60 may include any wavelength of visible light or UV light. In some embodiments, laser 60 emits alternative forms of radiation, such as, for example, microwave, ultrasound or radio frequency radiation. In some embodiments, laser 60 is configured to be focused on a portion of printing surface 12 to sinter material 40 deposited thereon. Laser 60 may be emitted in a beam having a small diameter. For example, the diameter of the beam may be between about 0.01 mm and about 0.8 mm. In some embodiments, the diameter of the beam may be between about 0.1 mm and about 0.4 mm. In some embodiments, the diameter of the beam is adjustable to customize the intensity of the sintering. In some embodiments, material 40 is deposited on printing surface 12 and print head 30 removes by, for example, heating material 40 to remove unwanted material 40 from printing surface 12 to make the implant. Material 40 remaining on printing surface 12 after removal of the unwanted material 40 will be the implant.

Figure 8:
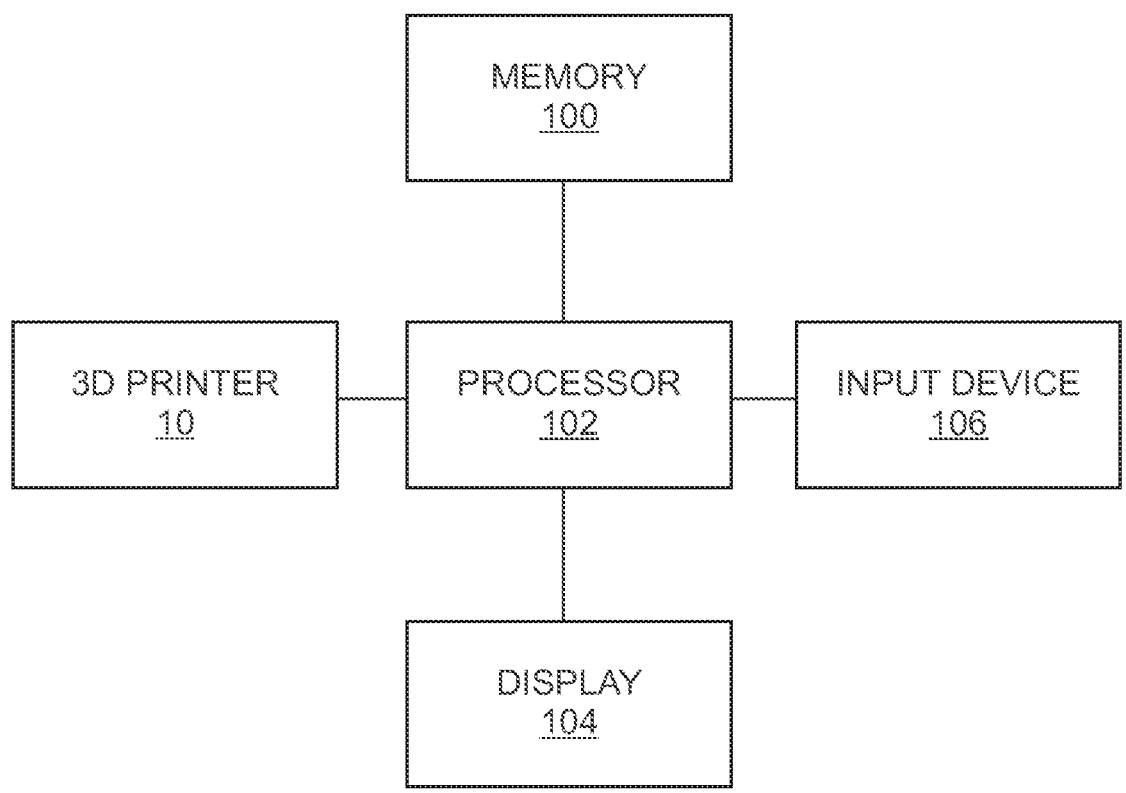
FIG. 8 illustrates an embodiment of a computer-implemented system for producing a hollow structure, such as a mesh bag.

In other aspects, as illustrated in FIG. 8, 3-D printing device 10 includes a controller or processor 102 to accept instructions and automatically manufacture a hollow structure, such as, for example, a mesh bag 70, based on the instructions. In some embodiments, processor 102 comprises memory 100 for temporary or permanent storage of instructions. Various instructions may be programmed and stored in memory 100 to make multiple designs of mesh bag 70 and/or mesh covers for mesh bag 70. In some embodiments, 3-D printing device 10 includes an input device 106, such as, for example, a keyboard to input commands and instructions. In some embodiments, processor 102 of 3-D printing device 10 is configured to receive commands and instructions from an external computer. For example, various instructions may be stored and executed locally on an external computer to operate 3-D printing device 10. In some embodiments, the computer and 3-D printing device 10 can be one single device with component parts.

In some embodiments, processor 102 comprises logic to execute one or more instructions to carry out instructions of the computer system (for example, transmit instructions to the 3-D printer, etc.). The logic for executing instructions may be encoded in one or more tangible media for execution by processor 102. For example, processor 102 may execute codes stored in a computer-readable medium such as memory 100. The computer-readable medium may be stored in, for example, electronic (for example, RAM (random access memory), ROM (read-only memory), EPROM (erasable programmable read-only memory), magnetic, optical (for example, CD (compact disc), DVD (digital video disc)), electromagnetic, semiconductor technology, or any other suitable medium.

In some embodiments, the instructions include dimensions of a mesh bag 70 to be made. For example, the instructions may include programming as to the length and thickness of mesh bag 70. Processor 102 carries out the instructions by causing movement of base 16 relative to print head 30 while material 40 is applied to printing surface 12. Additionally, processor 102 may cause movement of print head 30 in a direction away from printing surface 12 to allow for a thicker layer of material 40, according to the predetermined specifications in the instructions. In some embodiments, processor 102 is configured to provide a single layer of material 40 to make mesh bag 70. The layer of material 40 deposited onto printing surface 12 may have uniform thicknesses or may include varied thicknesses, such as thickness gradients across the length of mesh bag 70. In some embodiments, the dimensions of mesh bag 70 may range from about 1 cm to about 1 meter in length, or from about 3 cm to about 8 cm in length, from about 2 mm to about 30 mm in thickness, or from about 2 mm to about 10 mm in thickness, and from about 2 mm to about 30 mm in width, or from about 2 mm to about 10 mm in width.

Once processor 102 receives the instructions, processor 102 directs 3-D printing device 10 to make mesh bag 70 based on the received instructions. In some embodiments, processor 102 directs the lateral movement of base 16 and printing surface 12, and the movement of print head 30 transverse to base 16 and printing surface 12. In some embodiments, processor 102 also controls the direction of rotation, the degree of rotation and the speed of rotation of printing surface 12. In some embodiments, processor 102 moves, focuses and directs laser 60 to emit radiation at a predetermined point on printing surface 12. In some embodiments, processor 102 directs temperature control unit 50 to heat or cool printing surface 12. Based on the instructions received, processor 102 coordinates simultaneous and/or ordered movement of base 16, printing surface 12, and print head 30 relative to one another. Processor 102 also controls the application of material 40 onto printing surface 12. For example, processor 102 directs the pressure at which material 40 is released onto printing surface 12. Processor 102 also directs the patterns of application onto printing surface 12, including portions where material 40 is not applied to printing surface 12 to reduce waste. Processor 102 may also direct laser 60 to emit radiation, such as for example, focused beams of light, in controlled pulses to sinter preselected portions of material 40 on printing surface 12.

In some embodiments, processor 102 directs motors which control the movement and rotation of at least base 16, printing surface 12, and print head 30 relative to one another. In some embodiments, processor 102 directs coarse and/or fine movement of components of 3-D printing device 10.

Although the components of the system of FIG. 8 are shown as separate, they may be combined in one or more computer systems. Indeed, they may be one or more hardware, software, or hybrid components residing in (or distributed among) one or more local or remote computer systems. It also should be readily apparent that the components of the system as described herein may be merely logical constructs or routines that are implemented as physical components combined or further separated into a variety of different components, sharing different resources (including processing units, memory, clock devices, software routines, logic commands, etc.) as required for the particular implementation of the embodiments disclosed. Indeed, even a single general purpose computer (or other processor-controlled device) executing a program stored on an article of manufacture (for example, recording medium or other memory units) to produce the functionality referred to herein may be utilized to implement the illustrated embodiments. It also will be understood that the plurality of computers or servers can be used to allow the system to be a network based system having a plurality of computers linked to each other over the network or Internet or the plurality of computers can be connected to each other to transmit, edit, and receive data via cloud computers or in a data drop box.

The computer (for example, memory, processor, storage component, etc.) may be accessed by authorized users. Authorized users may include at least one engineer, technician, surgeon, physician, nurse, and/or health care provider, manufacturer, etc.

The user can interface with the computer via a user interface that may include one or more display devices 104 (for example, CRT, LCD, or other known displays) or other output devices (for example, a printer, etc.), and one or more input devices (for example, keyboard, mouse, stylus, touch screen interface, or other known input mechanisms) for facilitating interaction of a user with the system via user interface. The user interface may be directly coupled to database or directly coupled to a network server system via the Internet, Wi-Fi or cloud computing. In accordance with one embodiment, one or more user interfaces are provided as part of (or in conjunction with) the illustrated systems to permit users to interact with the systems.

The user interface device may be implemented as a graphical user interface (GUI) containing display 104 or the like, or may be a link to other user input/output devices known in the art. Individual ones of a plurality of devices (for example, network/stand-alone computers, personal digital assistants (PDAs), WebTV (or other Internet-only) terminals, set-top boxes, cellular phones, screen phones, pagers, blackberry, smart phones, iPhone, iPad, table, peer/non-peer technologies, kiosks, or other known (wired or wireless) communication devices, etc.) may similarly be used to execute one or more computer programs (for example, universal Internet browser programs, dedicated interface programs, etc.) to allow users to interface with the systems in the manner described. Database hardware and software can be developed for access by users through personal computers, mainframes, and other processor-based devices. Users may access and data stored locally on hard drives, CD-ROMs, stored on network storage devices through a local area network, or stored on remote database systems through one or more disparate network paths (for example, the Internet).

The database can be stored in storage devices or systems (for example, Random Access Memory (RAM), Read Only Memory (ROM), hard disk drive (HDD), floppy drive, zip drive, compact disk-ROM, DVD, bubble memory, flash drive, redundant array of independent disks (RAID), network accessible storage (NAS) systems, storage area network (SAN) systems, etc.). CAS (content addressed storage) may also be one or more memory devices embedded within a CPU, or shared with one or more of the other components, and may be deployed locally or remotely relative to one or more components interacting with the memory or one or more modules. The database may include data storage device, a collection component for collecting information from users or other computers into a centralized database, a tracking component for tracking information received and entered, a search component to search information in the database or other databases, a receiving component to receive a specific query from a user interface, and an accessing component to access centralized database. A receiving component is programmed for receiving a specific query from one of a plurality of users. The database may also include a processing component for searching and processing received queries against a data storage device containing a variety of information collected by a collection device.

The disclosed system may, in some embodiments, be a computer network based system. The computer network may take any wired/wireless form of known connective technology (for example, corporate or individual LAN, enterprise WAN, intranet, Internet, Wi-Fi, Virtual Private Network (VPN), combinations of network systems, etc.) to allow a server to provide local/remote information and control data to/from other locations (for example, other remote database servers, remote databases, network servers/user interfaces, etc.). In accordance with one embodiment, a network server may be serving one or more users over a collection of remote and disparate networks (for example, Internet, Wi-Fi, intranet, VPN, cable, special high-speed ISDN lines, etc.). The network may comprise one or more interfaces (for example, cards, adapters, ports) for receiving data, transmitting data to other network devices, and forwarding received data to internal components of the system (for example, 3-D printers, print heads, etc.).

In accordance with one embodiment of the present application, the data may be downloaded in one or more textual/graphical formats (for example, RTF, PDF, TIFF, JPEG, STL, XML, XDFL, TXT etc.), or set for alternative delivery to one or more specified locations (for example, via e-mail) in any desired format (for example, print, storage on electronic media and/or computer readable storage media such as CD-ROM, etc.). The user may view the search results and underlying documents at the user interface, which allows viewing of one or more documents on the same display 104.

Mesh Formulations

Figure 5:
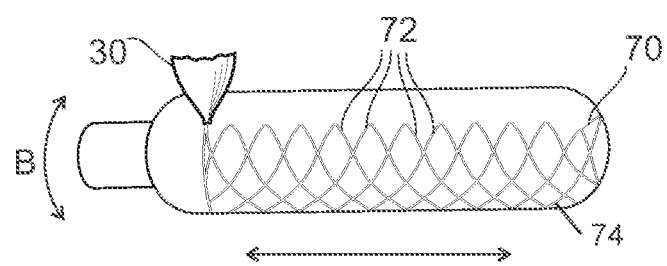
FIG. 5 illustrates a perspective view of components of an exemplary 3-D printing device according to an aspect of the present application. Specifically, shown is the movement of a printing surface while a print head, such as, for example, an applicator continuously extrudes material to the surface to form a mesh pattern.

In FIG. 5, a mesh bag 70 is being printed. In some embodiments, mesh bag 70 is formed from material extruded from print head 30. Mesh bag 70 comprises a system of threads 72 which are extruded directly onto printing surface. Threads 72 may be extruded in various patterns, and may be sized according to the requirements of a particular application. For example, threads 72 may be extruded from print head 30 in a weave pattern in which threads 72 are interwoven with one another such that each thread 72 alternatingly interlaces above and below adjacent threads 72. In other embodiments, threads 72 may be extruded in other ways. For example, horizontal rows of threads 72 may be extruded in a first step, and in second step vertical rows of threads 72 may be extruded on top of the horizontal rows. The threads 72 may include bone material 74 (e.g., DBM particles, allograft tissue particles, cortical bone particles, etc.) uniformly disposed throughout the threads 72. The material to make the threads 72 (e.g., biodegradable polymer) and the bone material 74 may be combined into one print head or be in separate print heads and then printed together or separately until the mesh bag 70 is formed. A radiation source, such as laser may be configured to sinter the extruded rows together to form mesh bag 70.

Figure 5A:
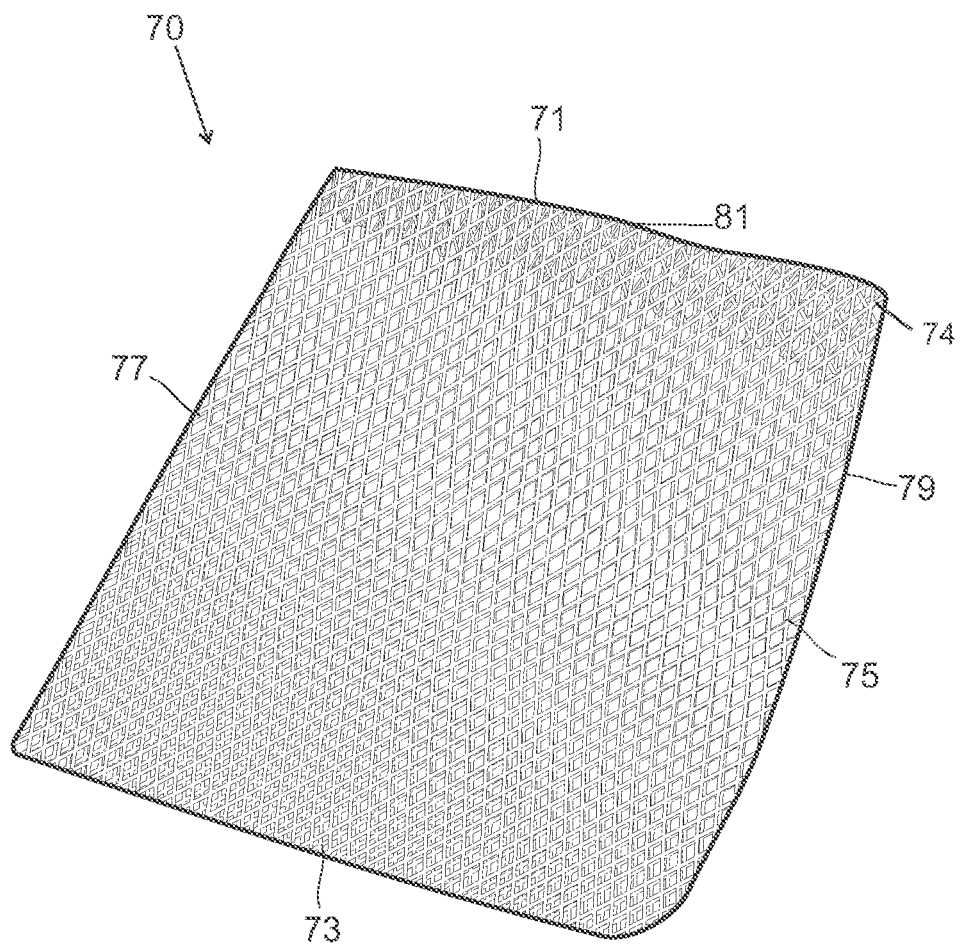
FIG. 5A illustrates a perspective view of a mesh bag having a hollow interior region formed from a 3-D printing device according to an aspect of the present application.

In some embodiments as shown in FIG. 5A, a completely printed mesh bag 70 is formed having a continuous surface 75 formed from threads 72. Mesh bag 70 includes oppositely positioned ends 77 and 79. There is no seal at these ends as mesh bag 70 was 3-D printed allowing for continuous manufacture. Mesh bags 70 that are not manufactured by 3-D printing would have seals on three of the four corners of the bag. In one embodiment of the 3-D printed mesh bag 70, a bottom end 73 of mesh bag 70 is the only one sealed so that contents do not fall out. In other embodiments, an end 71 is open to allow placement of bone material into the hollow region or compartment 81 of mesh bag 70. End 71 allows entrance into the hollow region or compartment 81 of mesh bag 70, where bone material is placed inside of it; the implant is then placed at a bone defect and mesh bag 70 allows the osteoinductive factors to leave mesh bag 70 and allows influx of bone cells into mesh bag 70. Mesh bag 70 is porous so as to allow influx and efflux of material.

Figure 5B:
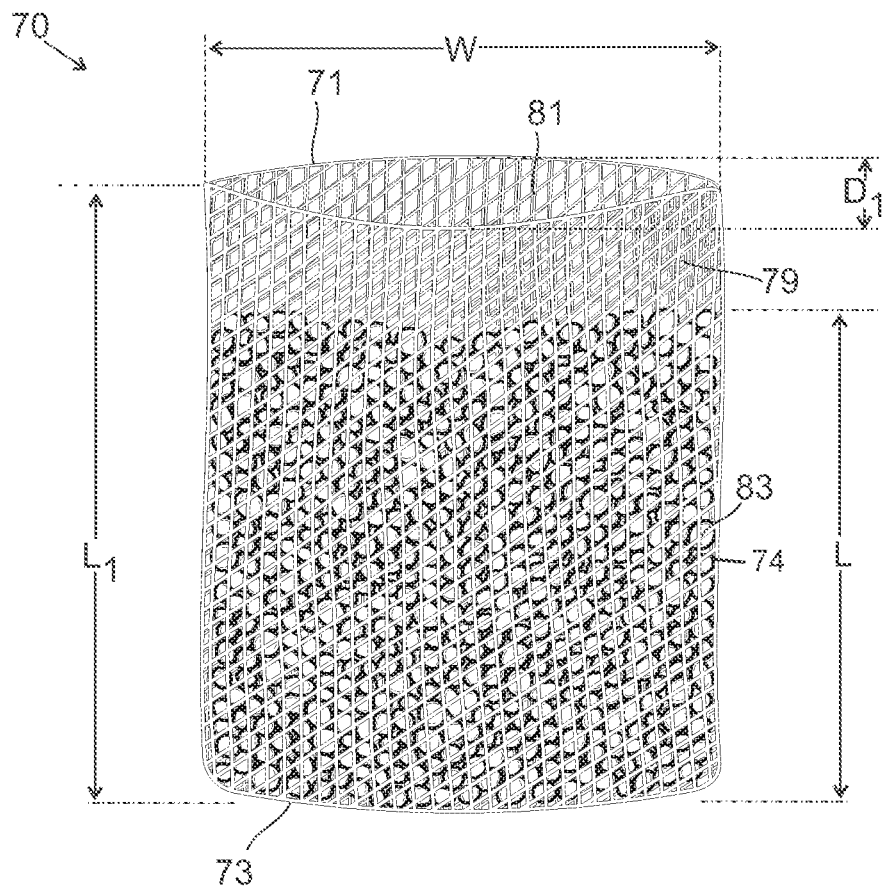
FIG. 5B illustrates a perspective view of a mesh bag as in FIG. 5A containing an osteogenic material in a hollow interior region or compartment.

In FIG. 5B, the hollow region or compartment 81 of mesh bag 70 is shown having end 71 of mesh bag 70. Mesh bag 70 is filled manually by hand or via an automated process with bone particles 83 (for example, surface demineralized chips and fully demineralized fibers) for use to enhance bone growth. The computer system may have a sensor to determine the proper level of filling of mesh bag 70 with bone material.

In some embodiments, the dimensions of printing surface 12 allows for printing mesh bag 70 of different dimensions and shapes that correspond to printing surface 12 (for example, circular, rectangular, square, etc.) The rotation of printing surface 12 shown as B in FIGS. 2 and 3, allows the implant (for example, mesh bag 70) to be printed continuously so that there is a reduced need for sealing the hollow region of the implant. The computer system can calculate the proper volume, length, width, and thickness of the cover to match the volume, length, width, and thickness of the compartment and/or mesh bag 70.

In some embodiments, mesh bag 70 is flexible so that it can be packed flat and it extends between oppositely positioned ends 77 and 79. In some embodiments, mesh bag 70 forms a cylindrical shape between oppositely positioned ends 77 and 79.

Threads 72 may be configured to allow ingrowth of cells while also retaining the osteogenic material within compartment 81 of mesh bag 70. In some embodiments, print head 30 is configured to extrude threads 72 having a predetermined thickness. In some embodiments, threads 72 have a thickness of about 0.01 mm to about 2.0 mm. In some embodiments, threads 72 have a thickness of about 0.05 mm to about 1.0 mm, or about 0.1 to about 0.5 mm. The thickness of threads 72 may be uniform along the length of each thread, or varied across the length of each thread. In some embodiments, some threads 72 have a greater thickness than other threads 72 in a mesh bag 70. Threads 72 may be sized to allow for customizable pore sizes between threads 72. In some embodiments, porous mesh bag 70 is configured to facilitate transfer of substances and/or materials surrounding the surgical site. Upon implantation to a surgical site, mesh bag 70 may participate in, control, or otherwise adjust, or may allow penetration of mesh bag 70 by surrounding materials, such as cells or tissue.

In various embodiments, mesh bag 70 may be sized according to the needs of a particular application. For example, mesh bag 70 may include dimensions between about 1 mm to about 100 mm in diameter, shown as W in FIG. 5B. In some embodiments, mesh bag 70 includes a diameter DI as illustrated in FIG. 5B of about 5 mm, 10 mm, 15 mm, 20 mm, 25 mm, 30 mm, 35 mm, 40 mm, 45 mm, 50 mm, 55 mm, 60 mm, 65 mm, 70 mm, 75 mm, 80 mm, 85 mm, 90 mm, 95 mm, or 100 mm. In some embodiments, mesh bag 70 includes a length or depth from about 0.1 cm to about 10 cm illustrated as L1 in FIG. 5B. In some embodiments, mesh bag 70 includes a length or depth of about 1 cm, 2 cm, 3 cm, 4 cm, 5 cm, 6 cm, 7 cm, 8 cm, 9 cm, or 10 cm. The desired dimensions can be selected by the user and the computer system can print the implant according to the selection.

In various embodiments, based on the foregoing dimensions, the volume of a 3-D printed tubular shaped mesh bag 70 can be easily calculated. For example, in some embodiments, a 3-D printed tubular mesh bag 70 having a diameter of 0.5 cm and a length of 0.1 cm would provide a volume of 0.02 cc. In other embodiments, a 3-D printed tubular mesh bag 70 having a diameter of 1 cm and a length of 1 cm would provide a volume of 0.79 cc. In yet other embodiments, a 3-D printed tubular mesh bag 70 having a diameter of 1.5 cm and length of 3 cm would provide a volume of 5.3 cc.

In some embodiments, threads 72 are extruded onto printing surface 12 in a wave-like configuration having alternating peaks and crests. In some embodiments, printing surface 12 is rotated in alternating clockwise and counterclockwise directions while material 40 is extruded onto the surface to create sinusoidal shaped waves having evenly shaped curves on the peaks and crests. In some embodiments, the peaks and crests of the waves are pointed to impart variable characteristics to mesh bag 70. In some embodiments, threads 72 are extruded adjacent to one another such that the peaks of a first thread 72 is extruded to contact the crest of an adjacent second thread 72. In some embodiments, mesh bag 70 may be created entirely from threads 72 having this configuration. Wave-shaped threads 72 impart flexibility and stretchable characteristics onto the manufactured mesh bag 70. The wavelength of the wave-shaped threads 72 may be altered to customize stretchability of mesh bag 70. For example, threads 72 having shorter wavelengths will be able to be stretched more than threads 72 having longer wavelengths. In some embodiments, the stretchability of mesh bag 70 is uniform across its length. In some embodiments, mesh bag 70 includes regions of increased stretchability according to the needs of a surgical application.

The shape, mesh size, thickness, and other structural characteristics, of mesh bags 70, for example, architecture, may be customized for the desired application. For example, to optimize cell or fluid migration through the mesh, the pore size may be optimized for the viscosity and surface tension of the fluid or the size of the cells. For example, pore sizes between threads 72 on the order of approximately 100-200 μm may be used if cells are to migrate through the mesh. In other embodiments, the wave-shaped threads 72 may be extruded to have larger peaks and crests and the size of the pores may be larger. For example, in some embodiments, the pore size between threads 72 may be about 0.1 mm to about 5 mm, about 0.5 mm to about 3 mm, or about 1 mm to about 2 mm. Mesh size may be controlled by physically weaving threads 72 and by controlling the thickness of threads 72 extruded and sintered on printing surface 12.

In various embodiments, mesh bag 70 made by 3-D printing device 10 may have varying degrees of permeability across its surface. It may be permeable, semi-permeable, or non-permeable. Permeability may be with respect to cells, to liquids, to proteins, to growth factors, to bone morphogenetic proteins, or other. In further embodiments, material 40 may be braided.

Mesh bag 70 may have any suitable configuration. For example, mesh bag 70 may be 3-D printed onto a printing surface 12 having a variety of shapes, such as, for example, a ring, a cylinder, a cage, a rectangular shape, a suture-like wrap, a continuous tube, or other configurations. Printing surface 12 provides a scaffold onto which mesh bag 70 is 3-D printed and from which mesh bag 70 derives its shape. In specific embodiments, mesh bag 70 may be formed as a thin tube designed to be inserted through catheters or an introducer tube; a rectangular shape designed to fit adjacent to spinal processes for posterolateral spine fusion; a cube; a rectangular prism like structure, as shown in FIG. 4, designed to fit between vertebral bodies or within cages for interbody spinal fusion; a tube-like shape; relatively flat shapes; rectangular shapes; structures pre-shaped to fit around various implants (e.g., dental, doughnut with hole for dental implants); or relatively elastic ring-like structures that will stretch and then conform to shapes (e.g. rubber band fitted around processes). In an embodiment, wherein mesh bag 70 is formed as a cage, the cage may comprise a plurality of crossed threads 72, which define between them a series of openings for tissue ingrowth. Any of these shapes may be used to contain osteogenic material such as bone material, as discussed herein. Mesh bags 70 may be printed and sintered onto printing surface 12 in such a way as to have one open end, as shown in FIGS. 5A and 5B.

Additionally, the flexible character of the mesh material allows for mesh bag 70 to be manipulated into a plurality of compartments. For example, in a tubular embodiment, the tube may be formed into a plurality of compartments by tying a cord around the tube at one or more points, or by other suitable mechanism such as crimping, twisting, knotting, stapling, or sewing and also including 3-D printing based on a 3-D digital model as more particularly described in this application.

A suitable mesh bag 70 that can be made by 3-D printing device 10 of the current application is the MAGNIFUSE® Bone Graft, available from Medtronic, which comprises surface demineralized bone chips mixed with non-demineralized cortical bone fibers or fully demineralized bone fibers sealed in an absorbable poly(glycolic acid) (PGA) mesh implant, bag or pouch.

In certain embodiments, a bone void can be filled by mesh bag 70 containing bone material. Compartment 81 within mesh bag 70 can be at least partially filled with a bone repair substance. In various embodiments, at least partially filled as used herein, can mean that a percentage of the volume of a compartment 81 or hollow interior region is at least 70% occupied, at least 75% occupied, at least 80% occupied, at least 85% occupied, at least 90% occupied, at least 95% occupied, or 100% occupied. In various embodiments, a sensing means or sensor in communication with the hollow compartment 81 of mesh bag 70 and also coupled to a computer processor can instruct the processor when a desired percentage volume of the compartment 81 was occupied. The processor can then instruct the 3-D printer to generate a covering for enclosing the bone material within mesh bag 70. Mesh bag 70 can be inserted into an opening in the defect until the defect is substantially filled. In various embodiments, substantially filled, as used herein, can mean that a percentage of the volume of a defect is at least 70% occupied, at least 75% occupied, at least 80% occupied, at least 85% occupied, at least 90% occupied, at least 95% occupied, or 100% occupied.

In some embodiments, mesh bag 70 may be labeled. Such labeling may be done in any suitable manner and at any suitable location on mesh bag 70. In some embodiments, labeling may be done by using a silk screen printing, using an altered weaving or knotting pattern, by using different colored threads 72, or other means. The labeling may indicate information regarding mesh bag 70. Such information might include a part number, donor ID number, number, lettering or wording indicating order of use in the procedure or implant size, etc.

In one embodiment, mesh bag 70 may comprise a penetrable material at a first compartment 81 configured for placement adjacent bone and a substantially impenetrable material at a second compartment 81 configured for placement adjacent soft tissue. For example, the pore size between threads 72 at a first region of mesh bag 70 may be sized large enough to allow cell migration through mesh bag 70, but the pore size between threads 72 at a second region of mesh bag 70 may be sized small enough (or may include a lack of pores altogether) to prevent cell migration. Alternatively, material 40 of mesh bag 70 may have a uniform configuration such that adjacent compartments 81 may have substantially identical characteristics. By way of example only, mesh bag 70 may have a porous surface that is positioned adjacent bone, and a separate or opposite surface that has a generally impenetrable surface that is positioned adjacent soft tissue. Alternatively, mesh bag 70 may have one compartment 81 that comprises a porous material, and a second compartment 81 that comprises a substantially impenetrable material.

For either single or multi-compartment mesh bags 70, mesh bag 70 may be closed after filling substances. Accordingly, mesh bag 70 may be provided in an unfilled, unsealed state immediately following fabrication with 3-D printing device 10. After a substance for delivery is placed in mesh bag 70, mesh bag 70 may be permanently or temporarily closed. Permanent closure may be, for example, by 3-D printing a covering for enclosing the bone material within compartment 81 of mesh bag 70. Temporary closure may be by tying, fold lock, cinching, or other means. A temporarily closed mesh bag 70 can be opened without damaging mesh bag 70 during surgical implantation to add or remove substances in mesh bag 70.

Suitable adhesives for use for closing mesh bag 70 may include, for example, cyanoacrylates (such as histoacryl, B Braun, which is n-butyl-2 cyanoacrylate; or Dermabond, which is 2-octylcyanoacrylate), epoxy-based compounds, dental resin sealants, dental resin cements, glass ionomer cements, polymethyl methacrylate, gelatin-resorcinol-formaldehyde glues, collagen-based glues, inorganic bonding agents such as zinc phosphate, magnesium phosphate or other phosphate-based cements, zinc carboxylate, L-DOPA (3,4-dihydroxy-L-phenylalanine), proteins, carbohydrates, glycoproteins, mucopolysaccharides, other polysaccharides, hydrogels, protein-based binders such as fibrin glues and mussel-derived adhesive proteins, and any other suitable substance. Adhesives may be selected for use based on their bonding time; for example, in some circumstances, a temporary adhesive may be desirable, for example, for fixation during the surgical procedure and for a limited time thereafter, while in other circumstances a permanent adhesive may be desired. Where compartment 81 is made of a material that is resorbable, the adhesive can be selected that would adhere for about as long as the material is present in the body.

In some embodiments, biological attachment may be via mechanisms that promote tissue ingrowth such as by a porous coating or a hydroxyapatite-tricalcium phosphate (HA/TCP) coating. Generally, hydroxyapatite bonds by biological effects of new tissue formation. Porous ingrowth surfaces, such as titanium alloy materials in a beaded coating or tantalum porous metal or trabecular metal may be used and facilitate attachment at least by encouraging bone to grow through the porous implant surface. These mechanisms may be referred to as biological attachment mechanisms. In some embodiments, mesh bag 70 may be attached to a tissue structure through a wrap, a suture, a wire, a string, an elastic band, a cable or a cable tie, or a combination thereof. In some embodiments, the attachment mechanism can be (i) integral to the 3-D printed seamless biodegradable mesh bag 70 or (ii) is provided separately from the 3-D printed seamless biodegradable mesh bag 70 and can be attached to the 3-D printed seamless biodegradable mesh bag 70 for use at an intended graft site.

In some embodiments, mesh bag 70 comprises an extruded material 40 arranged in a mesh configuration. In some embodiments, material 40 of mesh bag 70 is biodegradable. In some embodiments, mesh bag 70 includes only one material which is uniformly extruded to form the entirety of mesh bag 70. In some embodiments, mesh bag 70 comprises a blend of suitable materials 40. In some embodiments, a first group of threads 72 may comprise a first material 40 and a second group of threads 72 comprises a second material 40. In some embodiments, print head 30 is configured to extrude more than one type of material 40. In some embodiments, a first print head 30 is configured to extrude a first material 40 to form threads 72 and a second print head 30 is configured to extrude a second material 40 to form threads 72.

In other embodiments, suitable materials include natural materials, synthetic polymeric resorbable materials, synthetic polymeric non-resorbable materials, and other materials. Natural mesh materials include silk, extracellular matrix (such as DBM, collagen, ligament, tendon tissue, or other), silk-elastin, elastin, collagen, and cellulose. Synthetic polymeric resorbable materials include poly(lactic acid) (PLA), poly(glycolic acid) (PGA), poly(lactic acid-glycolic acid) (PLGA), polydioxanone, PVA, polyurethanes, polycarbonates, and others.

In various embodiments, material 40 of mesh bag 70 comprises a polymer matrix. In some embodiments, DBM fibers and/or DBM powder are suspended in the polymer matrix to facilitate transfer of cells into and out of mesh bag 70 to induce bone growth at the surgical site. In other embodiments, mesh bag 70 further comprises mineralized bone fibers suspended in the polymer matrix. In some embodiments, the DBM powder is suspended in the polymer matrix between the DBM fibers and the mineralized bone fibers. In some embodiments, the DBM powder is suspended between the DBM fibers in the polymer matrix so as to reduce and/or eliminate gaps that exist between the fibers. In some embodiments, the DBM powder is suspended between the DBM fibers in the polymer matrix to improve osteoinductivity for facilitating bone fusion, for example, interspinous process fusion.

In some embodiments, the polymer matrix comprises a bioerodible, a bioabsorbable, and/or a biodegradable biopolymer that may provide immediate release or sustained release. Examples of suitable sustained release biopolymers include, but are not limited to, poly (alpha-hydroxy acids), poly (lactide-co-glycolide) (PLGA), polylactide (PLA), polyglycolide (PG), polyethylene glycol (PEG), conjugates of poly (alpha-hydroxy acids), poly(orthoester)s (POE), polyaspirins, polyphosphagenes, collagen, starch, pre-gelatinized starch, hyaluronic acid, chitosans, gelatin, alginates, albumin, fibrin, vitamin E compounds, such as alpha tocopheryl acetate, d-alpha tocopheryl succinate, D,L-lactide, or L-lactide, caprolactone, dextrans, vinylpyrrolidone, polyvinyl alcohol (PVA), PVA-g-PLGA, PEGT-PBT copolymer (polyactive), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate), or combinations thereof. As persons of ordinary skill in the art are aware, mPEG and/or PEG may be used as a plasticizer for PLGA, but other polymers/excipients may be used to achieve the same effect. mPEG imparts malleability to the polymer. In some embodiments, these biopolymers may also be coated on mesh bag 70 to provide a desired release profile or ingrowth of tissue. In some embodiments, the coating thickness may be thin, for example, from about 5, 10, 15, 20, 25, 30, 35, 40, 45 or 50 microns to thicker coatings 60, 65, 70, 75, 80, 85, 90, 95, 100 microns to delay release of the substance from mesh implant 70. In some embodiments, the range of the coating on mesh bag 70 ranges from about 5 microns to about 250 microns or from about 5 microns to about 200 microns.

In various embodiments, various components of mesh bag 70 comprise poly(lactide-co-glycolide) (PLGA), polylactide (PLA), polyglycolide (PGA), D-lactide, D,L-lactide, L-lactide, D,L-lactide-co-ε-caprolactone, D,L-lactide-co-glycolide-co-ε-caprolactone, L-lactide-co-ε-caprolactone or a combination thereof.

In some embodiments, material 40 of mesh bag 70 further comprises bone morphogenetic proteins (BMPs), growth factors, antibiotics, angiogenesis promoting materials, bioactive agents or other actively releasing materials.

Mesh bag 70 may be used to deliver a substance comprising any suitable biocompatible material. In specific embodiments, mesh bag 70 may be used to deliver surface demineralized bone chips, optionally of a predetermined particle size, demineralized bone fibers, optionally pressed, and/or allograft. For embodiments wherein the substance is biologic, the substance may be autogenic, allogenic, xenogenic, or transgenic. Other suitable materials that may be positioned in mesh bag 70 include, for example, protein, nucleic acid, carbohydrate, lipids, collagen, allograft bone, autograft bone, cartilage stimulating substances, allograft cartilage, TCP, hydroxyapatite, calcium sulfate, polymer, nanofibrous polymers, growth factors, carriers for growth factors, growth factor extracts of tissues, DBM, dentine, bone marrow aspirate, bone marrow aspirate combined with various osteoinductive or osteoconductive carriers, concentrates of lipid derived or marrow derived adult stem cells, umbilical cord derived stem cells, adult or embryonic stem cells combined with various osteoinductive or osteoconductive carriers, transfected cell lines, bone forming cells derived from periosteum, combinations of bone stimulating and cartilage stimulating materials, committed or partially committed cells from the osteogenic or chondrogenic lineage, or combinations of any of the above.

In accordance with some embodiments, the material to be positioned in hollow compartment 81 of mesh bag 70 may be supplemented, further treated, or chemically modified with one or more bioactive agents or bioactive compounds. Bioactive agent or bioactive compound, as used herein, refers to a compound or entity that alters, inhibits, activates, or otherwise affects biological or chemical events. For example, bioactive agents may include, but are not limited to, osteogenic or chondrogenic proteins or peptides; DBM powder; collagen, insoluble collagen derivatives, etc., and soluble solids and/or liquids dissolved therein; anti-AIDS substances; anti-cancer substances; antimicrobials and/or antibiotics such as erythromycin, bacitracin, neomycin, penicillin, polymycin B, tetracyclines, biomycin, chloromycetin, and streptomycins, cefazolin, ampicillin, azactam, tobramycin, clindamycin and gentamycin, etc.; immunosuppressants; anti-viral substances such as substances effective against hepatitis; enzyme inhibitors; hormones; neurotoxins; opioids; hypnotics; anti-histamines; lubricants; tranquilizers; anti-convulsants; muscle relaxants and anti-Parkinson substances; anti-spasmodics and muscle contractants including channel blockers; miotics and anti-cholinergics; anti-glaucoma compounds; anti-parasite and/or anti-protozoal compounds; modulators of cell-extracellular matrix interactions including cell growth inhibitors and antiadhesion molecules; vasodilating agents; inhibitors of DNA, RNA, or protein synthesis; anti-hypertensives; analgesics; anti-pyretics; steroidal and non-steroidal anti-inflammatory agents; anti-angiogenic factors; angiogenic factors and polymeric carriers containing such factors; anti-secretory factors; anti-coagulants and/or antithrombotic agents; local anesthetics; ophthalmics; prostaglandins; anti-depressants; anti-psychotic substances; anti-emetics; imaging agents; biocidal/biostatic sugars such as dextran, glucose, etc.; amino acids; peptides; vitamins; inorganic elements; co-factors for protein synthesis; endocrine tissue or tissue fragments; synthesizers; enzymes such as alkaline phosphatase, collagenase, peptidases, oxidases and the like; polymer cell scaffolds with parenchymal cells; collagen lattices; antigenic agents; cytoskeletal agents; cartilage fragments; living cells such as chondrocytes, bone marrow cells, mesenchymal stem cells; natural extracts; genetically engineered living cells or otherwise modified living cells; expanded or cultured cells; DNA delivered by plasmid, viral vectors, or other member; tissue transplants; autogenous tissues such as blood, serum, soft tissue, bone marrow, or the like; bioadhesives; bone morphogenetic proteins (BMPs including BMP-2); osteoinductive factor (IFO); fibronectin (FN); endothelial cell growth factor (ECGF); vascular endothelial growth factor (VEGF); cementum attachment extracts (CAE); ketanserin; human growth hormone (HGH); animal growth hormones; epidermal growth factor (EGF); interleukins, for example, interleukin-1 (IL-1), interleukin-2 (IL-2); human alpha thrombin; transforming growth factor (TGF-beta); insulin-like growth factors (IGF-1, IGF-2); parathyroid hormone (PTH); platelet derived growth factors (PDGF); fibroblast growth factors (FGF, BFGF, etc.); periodontal ligament chemotactic factor (PDLGF); enamel matrix proteins; growth and differentiation factors (GDF); hedgehog family of proteins; protein receptor molecules; small peptides derived from growth factors above; bone promoters; cytokines; somatotropin; bone digesters; antitumor agents; cellular attractants and attachment agents; immuno-suppressants; permeation enhancers, for example, fatty acid esters such as laureate, myristate and stearate monoesters of polyethylene glycol, enamine derivatives, alpha-keto aldehydes; and nucleic acids.

In certain embodiments, the bioactive agent may be a drug. In some embodiments, the bioactive agent may be a growth factor, cytokine, extracellular matrix molecule, or a fragment or derivative thereof, for example, a protein or peptide sequence such as RGD.

In some embodiments, the polymer material used to make mesh bag 70 may have a modulus of elasticity in the range of from about $1 \times 10^2$ to about $6 \times 10$ dynes/cm$^2$, or $2 \times 10^4$ to about $5 \times 10^5$ dynes/cm$^2$, or $5 \times 10^4$ to about $5 \times 10$ dynes/cm$^2$.

Material 40 may have functional characteristics. Alternatively, other materials 40 having functional characteristics may be incorporated into mesh bag 70. Functional characteristics may include radiopacity, bacteriocidity, source for released materials, tackiness, etc. Such characteristics may be imparted substantially throughout mesh bag 70 or at only certain positions or portions of mesh bag 70.

Suitable radiopaque materials include, for example, ceramics, mineralized bone, ceramics/calcium phosphates/calcium sulfates, metal particles, fibers, and iodinated polymer (see, for example, WO/2007/143698). Polymeric materials may be used to form a bone graft or mesh bag 70 and be made radiopaque by iodinating them, such as taught for example in U.S. Pat. No. 6,585,755, herein incorporated by reference in its entirety. Other techniques for incorporating a biocompatible metal or metal salt into a polymer to increase radiopacity of the polymer may also be used. Suitable bacteriocidal materials may include, for example, trace metallic elements. In some embodiments, trace metallic elements may also encourage bone growth.

In some embodiments, mesh bag 70 may comprise a carrier material that becomes tacky upon wetting. Such material may be, for example, a protein or gelatin based material. Tissue adhesives, including mussel adhesive proteins and cryanocrylates, may be used to impart tackiness to mesh bag 70. In further examples, alginate or chitosan material may be used to impart tackiness to mesh bag 70. In further embodiments, an adhesive substance or material may be placed on a portion of mesh bag 70 or in a particular region of mesh bag 70 to anchor that portion or region of mesh bag 70 in place at an implant site.

Bone Material

In various embodiments, bone grafts, for example, mesh bags 70 made by 3-D printing device 10 include compartments 81 to hold osteogenic material, such as bone material. In various embodiments, the bone material may be particulated such as, for example, in bone chip, powder or fiber form. If the bone is demineralized, the bone may be made into a particulate before, during or after demineralization. In some embodiments, the bone may be monolithic and may not be a particulate.

The bone may be milled and ground or otherwise processed into particles of an appropriate size before or after demineralization. The particles may be particulate (for example, powder) or fibrous. The terms milling or grinding are not intended to be limited to production of particles of a specific type and may refer to production of particulate or fibrous particles. In certain embodiments, the particle size may be greater than 25 microns, such as ranging from about 25 to about 2000 microns, or from about 25 to about 500 microns or from about 200 to about 5000 microns. In some embodiments, the size of the bone particles are less than 100 microns. In some embodiments, the size of the bone particles are less than 500 microns.

After grinding, the bone particles may be sieved to select those particles of a desired size. In certain embodiments, the particles may be sieved though a 25 micron sieve, a 50 micron sieve, a 75 micron sieve, a 100 micron sieve, a 125 micron sieve, a 150 micron sieve, a 175 micron sieve and/or a 200 micron sieve.

In some embodiments, the bone particles comprise DBM and/or mineralized bone. In some embodiments, the size of the bone particles is less than 25 microns. In some embodiments, the bone particle size is about 1, 2, 3, 4, 5, 6, 7, 8, 9, 10, 11, 12, 13, 14, 15, 16, 17, 18, 19, 20, 21, 22, 23 and/or 24 microns.

In various embodiments, the bone particles and/or the DBM and/or mineralized bone fibers have a sticky outer surface such that the bone particles can adhere to DBM and/or mineralized bone fibers. In various embodiments, the bone particles are naturally sticky. In some embodiments, an adhesive agent is applied to the bone particles and/or the bone fibers comprising a bio-adhesive, glue, cement, cyanoacrylate, silicones, hot melt adhesives and/or cellulosic binders. In various embodiments, the adhesive may be applied to the surface of the bone particles by spraying or brushing. In some embodiments, a charge is applied to the fibers and an opposite charge is applied to the bone particles, (e.g., the technique of electrostatic precipitation). The bone particles will be attracted to, and tenaciously adhere to, the surface of the fiber. Any of these application techniques can be repeated one or more times to build up a relatively thick layer of adherent bone particles on the surface of the fibers.

The bone particles can be applied directly to the DBM fiber and/or fully mineralized fiber and the mixture can be disposed in mesh bag 70. In some embodiments, the bone material inserted into mesh bag 70 contains pores having a pore size from about 0.5 to about 2,000 microns. In some embodiments, bone material inserted into mesh bag 70 contains pores having a pore size of from about 0.5, 5, 50, 100, 150, 200, 250, 300, 350, 400, 450, 500, 550, 600, 650, 700, 750, 800, 850, 900, 950, 1,000, 1,050, 1,100, 1,150, 1,200, 1,250, 1,300, 1,350, 1,400, 1,450, 1,500, 1,550, 1,600, 1,650, 1,700, 1,750, 1,800, 1,850, 1,900, 1,950 to about 2,000 microns. In some embodiments, the pore size of the bone material is uniform. In some embodiments, the pore size of bone material is non-uniform and includes various pore sizes in the range from 0.5 to about 2,000 microns. Alternatively, the DBM fiber, and DBM particles can be placed in a polymer (for example, collagen) and inserted into a porous biodegradable graft body (for example, a pouch, container, mesh bag, and the like).

Following shaving, milling or other technique whereby they are obtained, the bone material is subjected to demineralization in order to reduce its inorganic content to a very low level, in some embodiments, to not more than about 5% by weight of residual calcium and preferably to not more than about 1% by weight of residual calcium. Demineralization of the bone material ordinarily results in its contraction to some extent.

Bone used in the methods described herein may be autograft, allograft, or xenograft. In various embodiments, the bone may be cortical bone, cancellous bone, or corticocancellous bone. While specific discussion is made herein to demineralized bone matrix, bone matrix treated in accordance with the teachings herein may be non-demineralized, demineralized, partially demineralized, or surface demineralized. This discussion applies to demineralized, partially demineralized, and surface demineralized bone matrix. In one embodiment, the demineralized bone is sourced from bovine or human bone. In another embodiment, demineralized bone is sourced from human bone. In one embodiment, the demineralized bone is sourced from the patient's own bone (autogenous bone). In another embodiment, the demineralized bone is sourced from a different animal (including a cadaver) of the same species (allograft bone).

Any suitable manner of demineralizing the bone may be used. Demineralization of the bone material can be conducted in accordance with known conventional procedures. For example, in a demineralization procedure, the bone materials useful for the implantable composition of this application are subjected to an acid demineralization step that is followed by a defatting/disinfecting step. The bone material is immersed in acid over time to effect its demineralization. Acids which can be employed in this step include inorganic acids such as hydrochloric acid and organic acids such as peracetic acid, acetic acid, citric acid, or propionic acid. The depth of demineralization into the bone surface can be controlled by adjusting the treatment time, temperature of the demineralizing solution, concentration of the demineralizing solution, agitation intensity during treatment, and other applied forces such as vacuum, centrifuge, pressure, and other factors such as known to those skilled in the art. Thus, in various embodiments, the bone material may be fully demineralized, partially demineralized, or surface demineralized.

After acid treatment, the bone is rinsed with sterile water for injection, buffered with a buffering agent to a final predetermined pH and then finally rinsed with water for injection to remove residual amounts of acid and buffering agent or washed with water to remove residual acid and thereby raise the pH. Following demineralization, the bone material is immersed in solution to effect its defatting. A defatting/disinfectant solution is an aqueous solution of ethanol, the ethanol being a good solvent for lipids and the water being a good hydrophilic carrier to enable the solution to penetrate more deeply into the bone. The aqueous ethanol solution also disinfects the bone by killing vegetative microorganisms and viruses. Ordinarily, at least about 10 to 40 weight percent by weight of water (e.g., about 60 to 90 weight percent of defatting agent such as alcohol) should be present in the defatting/disinfecting solution to produce optimal lipid removal and disinfection within the shortest period of time. A concentration range of the defatting solution is from about 60 to 85 weight percent alcohol or about 70 weight percent alcohol.

Further in accordance with this application, the DBM material can be used immediately for preparation of the implant or it can be stored under aseptic conditions, advantageously in a critical point dried state prior to such preparation. In one embodiment, the bone material can retain some of its original mineral content such that the composition is rendered capable of being imaged utilizing radiographic techniques.

In various embodiments, this application also provides bone matrix compositions comprising critical point drying (CPD) fibers DBM includes the collagen matrix of the bone together with acid insoluble proteins including bone morphogenetic proteins (BMPs) and other growth factors. It can be formulated for use as granules, gels, sponge material or putty and can be freeze-dried for storage. Sterilization procedures used to protect from disease transmission may reduce the activity of beneficial growth factors in the DBM. DBM provides an initial osteoconductive matrix and exhibits a degree of osteoinductive potential, inducing the infiltration and differentiation of osteoprogenitor cells from the surrounding tissues.

DBM preparations have been used for many years in orthopedic medicine to promote the formation of bone. For example, DBM has found use in the repair of fractures, in the fusion of vertebrae, in joint replacement surgery, and in treating bone destruction due to underlying disease such as rheumatoid arthritis. DBM is thought to promote bone formation in vivo by osteoconductive and osteoinductive processes. The osteoinductive effect of implanted DBM compositions is thought to result from the presence of active growth factors present on the isolated collagen-based matrix. These factors include members of the TGF-β, IGF, and BMP protein families. Particular examples of osteoinductive factors include TGF-β, IGF-1, IGF-2, BMP-2, BMP-7, parathyroid hormone (PTH), and angiogenic factors. Other osteoinductive factors such as osteocalcin and osteopontin are also likely to be present in DBM preparations as well. There are also likely to be other unnamed or undiscovered osteoinductive factors present in DBM.

In various embodiments, the DBM provided in the methods described in this application is prepared from elongated bone fibers which have been subjected to critical point drying. The elongated CPD bone fibers employed in this application are generally characterized as having relatively high average length to average width ratios, also known as the aspect ratio. In various embodiments, the aspect ratio of the elongated bone fibers is at least from about 50:1 to at least about 1000:1. Such elongated bone fibers can be readily obtained by any one of several methods, for example, by milling or shaving the surface of an entire bone or relatively large section of bone.

In other embodiments, the length of the fibers can be at least about 3.5 cm and average width from about 20 mm to about 1 cm. In various embodiments, the average length of the elongated fibers can be from about 3.5 cm to about 6.0 cm and the average width from about 20 mm to about 1 cm. In other embodiments, the elongated fibers can have an average length from about 4.0 cm to about 6.0 cm and an average width from about 20 mm to about 1 cm.

In yet other embodiments, the diameter or average width of the elongated fibers is, for example, not more than about 1.00 cm, not more than 0.5 cm or not more than about 0.01 cm. In still other embodiments, the diameter or average width of the fibers can be from about 0.01 cm to about 0.4 cm or from about 0.02 cm to about 0.3 cm.

In another embodiment, the aspect ratio of the fibers can be from about 50:1 to about 950:1, from about 50:1 to about 750:1, from about 50:1 to about 500:1, from about 50:1 to about 250.1, or from about 50.1 to about 100:1 Fibers according to this disclosure can advantageously have an aspect ratio from about 50:1 to about 1000:1, from about 50:1 to about 950:1, from about 50:1 to about 750:1, from about 50:1 to about 600:1, from about 50:1 to about 350:1, from about 50:1 to about 200:1, from about 50:1 to about 100:1, or from about 50:1 to about 75:1.

In some embodiments, the chips to fibers ratio is about 90:10, 80:20, 75:25, 70:30, 60:40, 50:50, 40.60, 30:70, 25:75, 20.80 and/or 10:90. In various embodiments, the ratio of surface demineralized chips to fibers is about 90:10, 80:20, 75:25, 70:30, 60:40, 50:50, 40:60, 30:70, 25:75, 20:80 and/or 10:90. In some embodiments, a surface demineralized chips to fully demineralized fibers ratio is about 90:10, 80:20, 75:25, 70:30, 60:40, 50:50, 40:60, 30:70, 25:75, 20:80 and/or 10:90.

In some embodiments, the DBM fibers have a thickness of about 0.5-4 mm. In various embodiments, the DBM fibers have a thickness of about 0.5, 0.6, 0.7, 0.8, 0.9, 1, 1.5, 2, 2.5, 3, 3.5 and/or 4 mm. In various embodiments, the ratio of DBM fibers to DBM powder is about 40:60 to about 90:10 W/W, W/V or V/V. In some embodiments, the ratio of mineralized bone fibers to DBM powder is about 25:75 to about 75:25 W/W, W/V or V/V. In various embodiments, the bone graft material comprises DBM fibers and mineralized fibers in a ratio of 40:60 to about 90:10 W/W, W/V or V/V. In some embodiments, the DBM fibers to DBM powder ratio, mineralized bone fibers to DBM powder ratio and/or the DBM fibers and mineralized fibers ratio is from 5:95 to about 95:5 W/W, W/V or V/V. In some embodiments, the DBM fibers to DBM powder ratio, mineralized bone fibers to DBM powder ratio and/or the DBM fibers and mineralized fibers ratio is 5:95, 10:90, 15:85, 20:80, 25:75, 30:70, 35:65, 40:60, 45:55, 50:50, 55:45, 60:40, 65:35, 70:30, 75:25, 80:20, 85:15, 90:10 and/or 95:5 W/W, W/V or V/V.

In some embodiments, the bone material comprises demineralized bone material comprising demineralized bone, fibers, powder, chips, triangular prisms, spheres, cubes, cylinders, shards or other shapes having irregular or random geometries. These can include, for example, "substantially demineralized," "partially demineralized," or "fully demineralized" cortical and/or cancellous bone. These also include surface demineralization, where the surface of the bone construct is substantially demineralized, partially demineralized, or fully demineralized, yet the body of the bone construct is fully mineralized.

In various embodiments, the bone graft material comprises fully DBM fibers and surface demineralized bone chips. In some embodiments, the ratio of fully DBM fibers to surface demineralized bone chips is from 5:95 to about 95:5 fibers to chips. In some embodiments, the ratio of fully DBM fibers to surface demineralized bone chips is 5:95, 10:90, 15:85, 20:80, 25:75, 30:70, 35:65, 40:60, 45:55, 50:50, 55:45, 60:40, 65:35, 70:30, 75:25, 80:20, 85:15, 90:10 and/or 95:5 fibers to chips. In various embodiments, the fully DBM fibers have a thickness of about 0.5-4 mm. In various embodiments, the fully DBM fibers have a thickness of about 0.5, 0.6, 0.7, 0.8, 0.9, 1, 1.5, 2, 2.5, 3, 3.5 and/or 4 mm.

In various embodiments, the fibers and/or the powder is surface DBM. In some embodiments, the fibers and/or the powder is surface DBM cortical allograft. In various embodiments, surface demineralization involves surface demineralization to at least a certain depth. For example, the surface demineralization of the allograft can be from about 0.25 mm, 0.5 mm, 1 mm, 1.5 mm, 2.0 mm, 2.5 mm, 3.0 mm, 3.5 mm, 4 mm, 4.5 mm, to about 5 mm. The edges of the bone fibers and/or powder may further be machined into any shape or to include features such as grooves, protrusions, indentations, etc., to help improve fit and limit any movement or micromotion to help fusion and/or osteoinduction to occur.

To prepare the osteogenic DBM, a quantity of fibers is combined with a biocompatible carrier material to provide a demineralized bone matrix.

DBM typically is dried, for example via lyophilization or solvent drying, to store and maintain the DBM in active condition for implantation. Moreover, each of these processes is thought to reduce the overall surface area structure of bone. As may be appreciated, the structural damage of the exterior surface reduces the overall surface area. Physical alterations to the surface and reduction in surface area can affect cell attachment, mobility, proliferation, and differentiation. The surface's affinity for growth factors and release kinetics of growth factors from the surface may also be altered.

Accordingly, in some embodiments, methods for drying bone to store and maintain the bone in active condition for implantation that maintains or increases the surface area of the bone are provided. In one embodiment, the bone matrix is treated using critical point drying (CPD) technique, thereby reducing destruction of the surface of the bone. While specific description is made to critical point drying, it is to be appreciated that, in alternative embodiments, super critical point treatment may be used. In various embodiments utilizing CPD, a percentage of collagen fibrils on the surface of the bone are non-denatured after drying to a residual moisture content of approximately 15% or less. In some embodiments, after drying, the bone matrix has a residual moisture content of approximately 8% or less. In some embodiments, after drying, the bone matrix has a residual moisture content of approximately 6% or less. In some embodiments, after drying, the bone matrix has a residual moisture content of approximately 3% or less.

Evaporative drying and freeze drying of specimens can cause deformation and collapse of surface structures, leading to a decrease in surface area. Without wishing to be bound by a particularly theory, this deformation and structure is thought to occur because as a substance crosses the boundary from liquid to gas, the substance volatilizes such that the volume of the liquid decreases. As this happens, surface tension at the solid-liquid interface pulls against any structures to which the liquid is attached. Delicate surface structures tend to be broken apart by this surface tension. Such damage may be caused by the effects of surface tension on the liquid/gas interface. Critical point drying is a technique that avoids effects of surface tension on the liquid/gas interface by substantially preventing a liquid/gas interface from developing. Critical point or supercritical drying does not cross any phase boundary, instead passing through the supercritical region, where the distinction between gas and liquid ceases to apply. As a result, materials dehydrated using critical point drying are not exposed to damaging surface tension forces. When the critical point of the liquid is reached, it is possible to pass from liquid to gas without abrupt change in state. Critical point drying can be used with bone matrices to phase change from liquid to dry gas without the effects of surface tension. Accordingly, bone dehydrated using critical point drying can retain or increase at least some of the surface structure and therefore the surface area.

In some embodiments, critical point drying is carried out using carbon dioxide. However, other mediums such as Freon, including Freon 13 (chlorotrifluoromethane), may be used. Generally, fluids suitable for supercritical drying include carbon dioxide (critical point 304.25 K at 7.39 MPa or 31.1° C. at 1072 psi or 31.2° C. and 73.8 bar) and Freon (about 300 K at 3.5-4 MPa or 25 to 30° C. at 500-600 psi). Nitrous oxide has similar physical behavior to carbon dioxide, but is a powerful oxidizer in its supercritical state. Supercritical water is also a powerful oxidizer, partly because its critical point occurs at such a high temperature (374° C.) and pressure (3212 psi/647K and 22.064 MPa).

In some embodiments, the bone may be pretreated to remove water prior to critical point drying. Thus, in accordance with one embodiment, bone matrix is dried using carbon dioxide in (or above) its critical point status. After demineralization, bone matrix samples (in water) may be dehydrated to remove residual water content. Such dehydration may be obtained, for example, by using a series of graded ethanol solutions (for example, 20%, 50%, 70%, 80%, 90%, 95%, 100% ethanol in deionized water). In some embodiments, penetrating the tissue with a graded series of ethanol solutions or alcohols may be accomplished in an automated fashion. For example, pressure and vacuum could be used to accelerate penetration into the tissue.

Methods of Making a Mesh Implant

Figure 10:
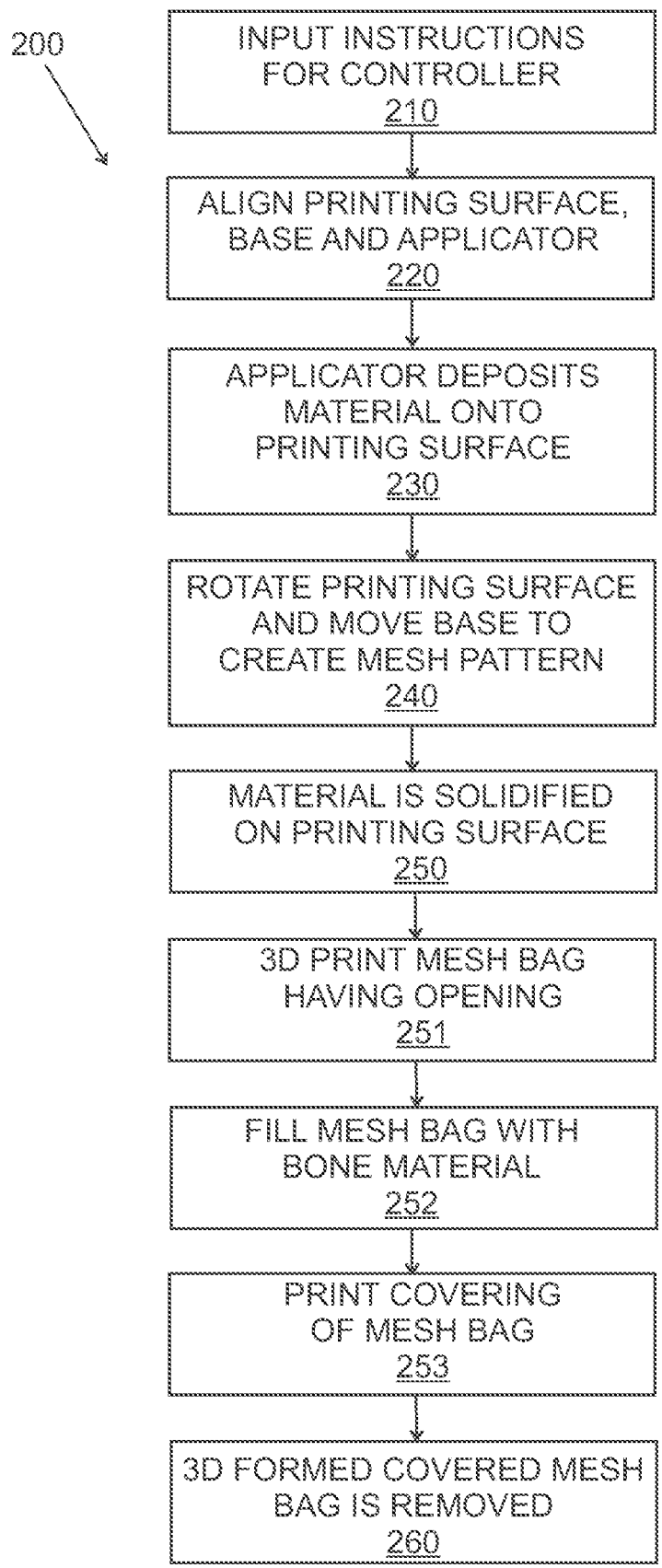
FIG. 10 is a flow diagram illustrating an embodiment of a system for producing a hollow structure, such as a mesh implant or bag, through the use of a 3-D printing machine having a rotating printing surface.

In various embodiments as shown in FIG. 10, a computer implemented method 200 of fabricating a hollow structure, such as mesh bag 70, through use of a 3-D printing device 10 is provided. In some embodiments, the method includes step 210 for inputting instructions for a computer processor 102 to carry out the fabrication, step 220 for aligning printing surface 12, base 16 and print head 30 relative to one another, step 230 for depositing material 40 onto printing surface 12, step 240 for rotating printing surface 12 and moving base 16 to create a mesh pattern, step 250 for solidifying material 40 on printing surface 12, step 251 for 3-D printing of mesh bag 70 having compartment 81 that is accessible through an opening, step 252 for filling compartment 81 with bone material, step 253 for enclosing mesh bag 70 by 3-D printing a covering for enclosing the bone material within compartment 81 of mesh bag 70 and step 260 for removing the 3-D formed and covered mesh bag 70. In some embodiments, the method comprises: rotating a print surface in alternating clockwise and counterclockwise directions, ejecting material from a print head to the print surface to make a strand having a wave-like pattern with alternating peaks and crests, and rotating the print head such an angular distance to create a plurality of interconnected threads on the printing surface.

In some embodiments, a method for fabricating a hollow structure is provided which includes providing a 3-D printing machine 10 having a table 14, a base 16 and a printing surface 12. In various embodiments, printing surface 12 is rotatable about an axis of rotation. Base 16 is configured for planar movement. Printing surface 12 is fixedly disposed with table 14 such that lateral movement of base 16 causes lateral movement of printing surface 12. In some embodiments, base 16 is movable in the x-y plane and is laterally movable in both the x axis and the y axis for precise positioning of printing surface 12. Movement of base 16 allows for positioning of printing surface 12 relative to extension shaft 20 to facilitate depositing materials 40 onto printing surface 12, as discussed herein. 3-D printing device 10 further includes a print head 30 to deposit material 40 onto printing surface 12. The deposit material 40 includes material used to make the mesh (e.g., biodegradable polymer, biodegradable polymer and bioactive agent mixed together, biodegradable polymer and bone material mixed together, etc.).

In other embodiments, a processor 102 receives instructions for the fabrication of a mesh bag 70. A user may input instructions directly into 3-D printing device 10 or may input instructions into an external computer in communication with processor 102. Processor 102 directs movement of base 16, printing surface 12 and print head 30 relative to one another. Processor 102 also directs application of material 40 from print head 30 onto printing surface 12.

According to various aspects, a user loads a material reservoir (not shown) in communication with print head 30 with a suitable material 40. Material 40 may be in powder form, particulate form, gel form, or solid form. Processor 102 moves printing surface 12 and one or more print heads 30 into place relative to one another. Once positioned, print head 30 begins to deposit material 40 onto printing surface 12. In some embodiments, print head 30 continuously deposits material 40 as printing surface 12 is rotated and/or moved laterally along the x-y plane. In some embodiments, printing surface 12 is rotated in the clockwise and counterclockwise directions while base 16 moves laterally to form wave-shaped threads 72. The degree of rotation may be adjusted to impart flexible and stretchable qualities onto each of the formed threads 72. For example, threads 72 having shorter wavelengths will be able to be stretched more than threads 72 having longer wavelengths. In some embodiments, processor 102 directs rotation of printing surface 12 and lateral movement of base 16 to impart stretchability of mesh bag 70 that is uniform across its length. In some embodiments, processor 102 directs variable rotation of printing surface 12 and lateral movement of base 16 such that mesh bag 70 includes regions of increased stretchability according to the needs of a surgical application.

The movement of base 16, printing surface 12 and print head 30 relative to one another and the application of material 40 onto printing surface 12 is repeated a number of times such that threads 72 encompass the surface of printing surface 12. That is, each time a thread having a wave-like shape is applied to printing surface 12, a similar thread 72 is applied to printing surface 12 adjacent the first thread. In some embodiments, threads 72 are extruded adjacent to one another such that the peaks of a first thread 72 are extruded to contact the crest of an adjacent second thread 72. In some embodiments, mesh bag 70 may be created entirely from threads 72 having this configuration.

In some embodiments, print head 30 deposits material 40 in powdered form onto printing surface 12. Material 40 must be sintered and/or melted to form threads 72. In some embodiments, a radiation source, such as laser 60 may be used in conjunction with print head 30. Processor 102 directs laser 60 to be focused at a point on which material 40 has been deposited adjacent print head 30. Processor 102 also provides power to laser 60 during desired intervals to prevent unwanted damage to mesh bag 70 and/or printing surface 12 according to the instructions. That is, laser 60 will emit a beam while sintering material 40 to create threads 72, but will not emit a beam when printing surface 12 is being repositioned relative to print head 30. Once all desired sintering has been completed, any excess material 40 may be brushed away from printing surface 12 to be discarded or recycled.

In some embodiments, material 40 may be sintered through use of temperature control unit 50 (e.g., a heating unit) as illustrated in FIG. 1. Temperature control unit 50 provides energy to printing surface 12 such that powdered material 40 melts and molds together. An amount of heat may be provided such that material 40 melts quickly upon contact with printing surface 12.

In some embodiments, printing surface 12 is heated or cooled using temperature control unit 50 to remove mesh bag 70. In some embodiments, printing surface 12 may be removed from 3-D printing device 10 and submerged in a solvent to loosen and remove mesh bag 70.

Figure 9:
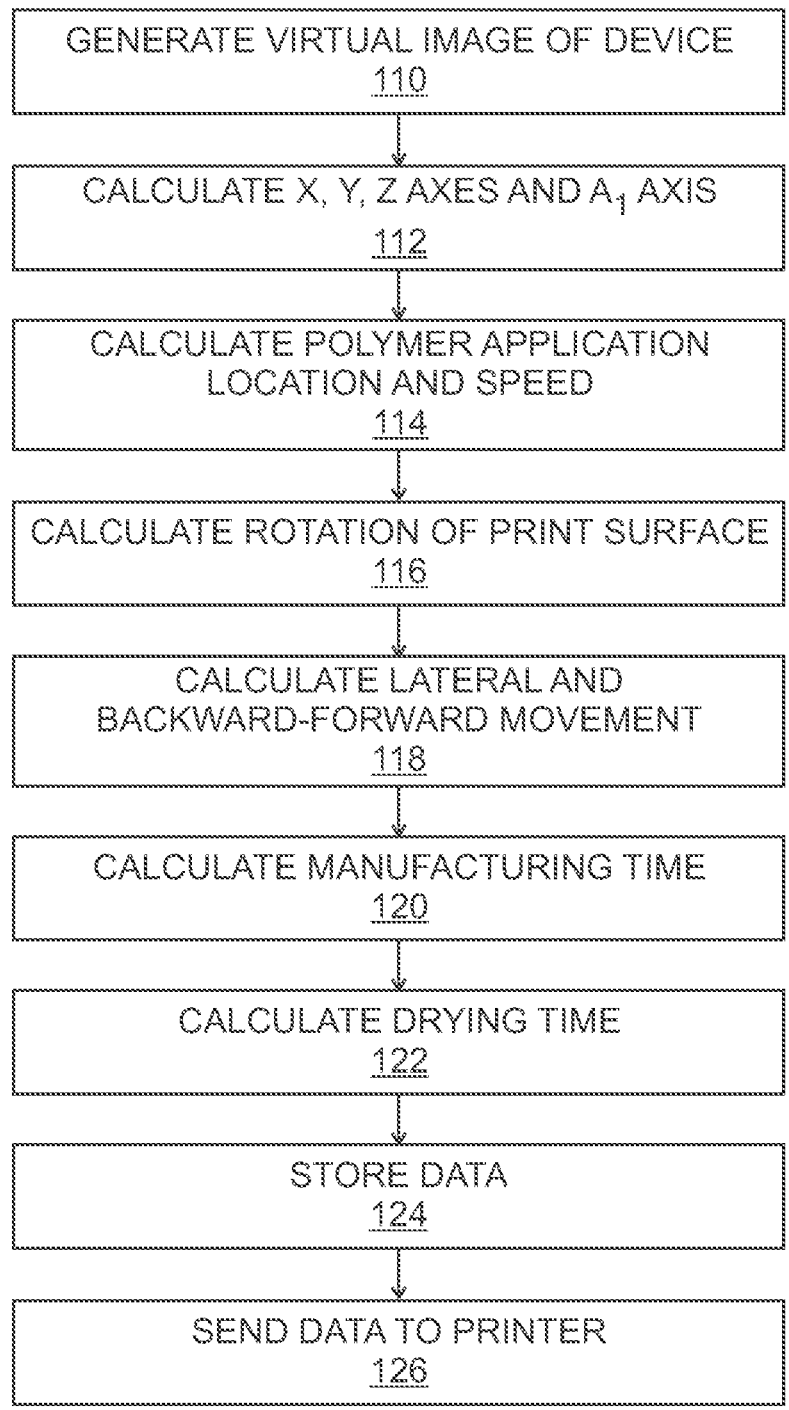
FIG. 9 is a flow diagram illustrating an embodiment of the computer-implemented system for producing a hollow structure, such as a mesh bag.

As shown in FIG. 9, a computer implemented method for producing a hollow structure such as a mesh bag is illustrated. In a first step 110, a user or a designer generates a virtual image of the object or a 3-D digital model to be created with the 3-D printing machine, such as, for example, mesh bag 70 including a virtual volume of compartment 81 to enclose the bone material therein and a virtual depth, thickness and volume of mesh bag 70 and a covering configured for enclosing compartment 81 of mesh bag 70. The computer can generate a virtual 3-D image of the cover including a virtual volume, length, and width of the covering to be printed. Commercially available CAM software can make the CAD drawing/design of mesh bag 70 into a computer code, (for example, g-code). This code is sent to the device and the controller controls the device and the loading of print head 30 with material 40, the heating and cooling temperature and time of material 40, laser emit time, rotation, rotation speed of printing surface 12, print head 30, table 14, lateral movement of printing surface 12, print head 30, and table 14 as well as other parameters. The controller device creates a medical implant from or in the material based on the 3-D digital model. In some embodiments the 3-D digital model of mesh bag 70 is generated based on the 3-D image of an intended bone repair site. The 3-D image of a bone repair site can be obtained by using (i) one or more X-ray images; (ii) a computer aided design (CAD) program (iii) a cone beam imaging device; (iv) a computed tomography (CT) scan device; (v) a magnetic resonance imaging (MRI); (vi) 3-D laser camera, or a combination thereof.

In a second step 112, processor 102 calculates the X, Y, Z and $A_1$ axes. The device employs Cartesian coordinate system (X, Y, Z) for 3-D motion control and employs a 4th axis ($A_1$) for the rotation of printing surface 12 (for example, 360 degrees) relative to print head 30. The implant can be designed virtually in the computer with a CAD/CAM program, which is on a computer display. The user inputs specific parameters into the computer and then presses print on the display to start the 3-D printing manufacturing. The computer logic programs the computer with instructions for loading of print head 30 with material 40; application and thickness of the polymer from print head 30; the heating and cooling temperature and time of the device; laser emit time; rotation; rotation speed of printing surface 12, print head 30, and/or table 14; and/or lateral movement of printing surface 12, print head 30, and/or table 14 as well as other parameters in accordance with the received instructions. The controller device causes print head 30 to be located at the appropriate X, Y, Z coordinates for 3-D motion control and employs a 4th axis ($A_1$) for the rotation of printing surface 12 (for example, 360 degrees, 180 degrees, 120 degrees) relative to print head 30 to make a medical implant from or in material 40. After the medical implant is produced on all or a portion of printing surface 12, it will have compartment 81 or a hollow region which typically is greater than the diameter or thickness of printing surface 12 and can be removed by a tool that engages printing surface 12. In some embodiments, the device can have a tool to etch, shape, and/or dry the implant before, during or after it is removed from printing surface 12.

In a third step 114, processor 102 calculates the polymer application location and speed by planning coordination of printing surface 12 and print head 30. In some embodiments, the current device does not manufacture the implant device by printing material 40 in successive layers to form the implant. In a fourth step 116 and a fifth step 118, processor 102 calculates the rotation of printing surface 12 and the lateral and/or backward and forward movement of printing surface 12 and print head 30. In some embodiments, printing surface 12 of the current application has the polymer continuously dispensed from print head 30 and onto printing surface 12 as printing surface 12 rotates in 360 degrees clockwise and/or counterclockwise relative to print head 30 and table 14, and/or printing surface 12 can, in some embodiments, move in a forward, lateral, and/or backward direction so that the threads to make the medical implant (for example, mesh bag 70) are formed in accordance with the instructions received from the computer. In some embodiments, printing surface 12 of the current application has a heat sensitive polymer disposed on it and then print head 30 receives instructions to heat the surface area to be removed (for example, by laser, heating element, or the like). In this way, threads 72 of the polymer are made by removing the heated portions of the polymer and what is left on printing surface 12 are threads 72 for the implant. Printing surface 12 rotates in 360 degrees clockwise and/or counterclockwise relative to print head 30 and table 14, and/or printing surface 12 can, in some embodiments, move in a forward, lateral, and/or backward direction so that threads 72 make the medical implant (for example, mesh bag 70) are formed as the rest of the polymer is removed from printing surface 12 in accordance with the instructions received from the computer.

In some embodiments, printing surface 12 of the current application has the polymer in dry powder form continuously dispensed from print head 30 and onto printing surface 12 as printing surface 12 rotates in 360 degrees clockwise and/or counterclockwise relative to print head 30 and table 14, and/or printing surface 12 can, in some embodiments, move in a forward, lateral, and/or backward direction so that threads 72 make the medical implant (for example, mesh bag 70) are formed in accordance with the instructions received from the computer. After, the powder application, which can be from print head 30 from a reservoir therein, print head 30 (for example, a laser 60 or heating element coupled thereto) can heat the powder polymer and form threads 72 for the medical implant.

Based on the above calculations, processor 102 calculates a projected amount of time it will take to manufacture the medical implant in step 120. In a subsequent step 122, processor 102 calculates the amount of time it will take for the printed medical device to dry. In some embodiments, material 40 applied to printing surface 12 is temperature sensitive and dries and/or cures through heating or cooling. In some embodiments, processor 120 directs temperature control unit 50 to heat or cool printing surface 12. In some embodiments, processor 120 directs laser 60 to focus its beam on material 40 applied to printing surface 12 to sinter and cure material 40.

In step 124, the data calculated by processor 102 is stored in memory 100 for subsequent implementation. In some embodiments, processor 102 processes and organizes the calculated data into memory 100. In some embodiments, processor 102 includes value-determining logic, development logic, security logic, and/or analytical logic. In some embodiments, processor 102 updates memory 100 with any new calculation data received from the user. In some embodiments, there is a computer readable storage medium storing instructions that, when executed by a computer, cause the computer to display options for a user to enter, view, and edit some or all features for manufacturing the implant including the loading of print head 30 with material 40; the heating and cooling temperature and time of material 40; laser emit time; rotation angle; rotation speed of printing surface 12, print head 30 and/or table 14; lateral movement of printing surface 12, print head 30 and table 14; as well as other parameters. The controller device creates a medical implant from or in material 40 by instructions received from the computer. The device employs Cartesian coordinate system (X, Y, Z) for 3-D motion control and employs a 4th axis ($A_1$) for the rotation of printing surface 12 (for example, 360 degrees) relative to print head 30.

In a final step 126, the user inputs a command to send the stored data to the printer to create the medical device. The user inputs specific parameters into the computer and then presses print on the display to start the 3-D printing manufacturing. The computer logic causes the computer to execute loading of print head 30 with material 40; the heating and cooling temperature and time of the device; laser emit time; rotation; rotation speed of printing surface 12, print head 30, and/or table 14; and/or lateral movement of printing surface 12, print head 30, and/or table 14; as well as other parameters. The controller device causes print head 30 to be located at the appropriate X, Y, Z coordinates for 3-D motion control and employs a 4th axis ($A_1$) for the rotation of printing surface 12 (for example, 360 degrees, 180 degrees, 120 degrees) relative to print head 30 to make a medical implant from or in material 40.

Method of Making a Bone Graft

In various embodiments, a computer implemented method for producing a bone graft is provided. The computer implemented method for producing a bone graft includes obtaining a 3-D image of an intended bone graft site, generating a 3-D digital model of the bone graft based on the 3-D image of the intended bone graft site, the 3-D digital model of the bone graft being configured to fit within the intended bone graft site; storing the 3-D digital model previously obtained on a database coupled to a processor, the processor having instructions for retrieving the stored 3-D digital model of the bone graft, and the processor also having instructions for combining a carrier material with, in or on a bone material based on the stored 3-D digital model and for instructing a 3-D printer to produce the bone graft.

In some aspects, the computer implemented method produces the bone graft by combining the carrier material with the bone material and instructing the 3-D printer to print the bone graft based on the stored 3-D digital model. In other aspects, the computer implemented method produces the bone graft by instructing the 3-D printer to print the carrier material and then print the bone material in or on the carrier based on the stored 3-D digital model. In yet other embodiments, the computer implemented method produces a bone graft which is customized to the intended bone graft site.

In certain embodiments, the 3-D image of an intended bone graft site is a computed tomography image of an unhealthy bone graft site, based on a computed tomography image of a healthy bone graft site. In other embodiments, the 3-D image is obtained from (i) one or more X-ray images; (ii) a computer aided design (CAD) program; (iii) a cone beam imaging device; (iv) a computed tomography (CT) scan device; (v) a magnetic resonance imaging (MRI) or a combination thereof.

Generally, in many implementations, the carrier material comprises a biodegradable polymer, a metal, or a combination thereof and the bone material comprises mineralized or demineralized bone.

In some embodiments, the bone graft includes biodegradable polymers. Exemplary biodegradable materials include lactide-glycolide copolymers of any ratio (e.g., 85:15, 40:60, 30:70, 25:75, or 20:80), poly(L-lactide-co-D,L-lactide), polyglyconate, poly(arylates), poly(anhydrides), poly(hydroxy acids), polyesters, poly(ortho esters), poly(alkylene oxides), polycarbonates, poly(propylene fumarates), poly (propylene glycol-co fumaric acid), poly(caprolactones), polyamides, polyesters, polyethers, polyureas, polyamines, polyamino acids, polyacetals, poly(orthoesters), poly(pyrolic acid), poly(glaxanone), poly(phosphazenes), poly(organophosphazene), polylactides, polyglycolides, poly(dioxanones), polyhydroxybutyrate, polyhydroxyvalyrate, polyhydroxybutyrate/valerate copolymers, poly(vinyl pyrrolidone), biodegradable polycyanoacrylates, biodegradable polyurethanes including glucose-based polyurethanes and lysine-based polyurethanes, and polysaccharides (e.g., chitin, starches, celluloses). In certain embodiments, the polymer used in the bone graft is poly(lactide-co-glycolide). The ratio of lactide and glycolide units in the polymer may vary.

Particularly useful ratios are approximately 45-80% lactide to approximately 44-20% glycolide. In certain embodiments, the ratio is approximately 50% lactide to approximately 50% glycolide. In other certain embodiments, the ratio is approximately 65% lactide to approximately 45% glycolide. In other certain embodiments, the ratio is approximately 60% lactide to approximately 40% glycolide. In other certain embodiments, the ratio is approximately 70% lactide to approximately 30% glycolide. In other certain embodiments, the ratio is approximately 75% lactide to approximately 25% glycolide. In certain embodiments, the ratio is approximately 80% lactide to approximately 20% glycolide. In certain of the above embodiments, lactide is D,L-lactide. In other embodiments, lactide is L-lactide. In certain particular embodiments, RESOMER® 824 (poly-L-lactide-co-glycolide) (Boehringer Ingelheim) is used as the polymer in the bone graft. In certain particular embodiments, RESOMER® 504 (poly-D,L-lactide-co-glycolide) (Boehringer Ingelheim) is used as the polymer in the bone graft. In certain particular embodiments, PURASORB PLG (75/25 poly-L-lactide-co-glycolide) (Purac Biochem) is used as the polymer in the bone graft. In certain particular embodiments, PURASORB PG (polyglycolide) (Purac Biochem) is used as the polymer in the bone graft. In certain embodiments, the polymer is PEGylated-poly(lactide-co-glycolide). In certain embodiments, the polymer is PEGylated-poly(lactide). In certain embodiments, the polymer is PEGylated-poly(glycolide). In other embodiments, the polymer is polyurethane. In other embodiments, the polymer is polycaprolactone.

In certain embodiments, the biodegradable polymer is a copolymer of poly(caprolactone) and poly(lactide). For polyesters such as poly(lactide) and poly(lactide-co-glycolide), the inherent viscosity of the polymer ranges from about 0.4 dL/g to about 5 dL/g. In certain embodiments, the inherent viscosity of the polymer ranges from about 0.6 dL/g to about 2 dL/g. In certain embodiments, the inherent viscosity of the polymer ranges from about 0.6 dL/g to about 3 dL/g. In certain embodiments, the inherent viscosity of the polymer ranges from about 1 dL/g to about 3 dL/g. In certain embodiments, the inherent viscosity of the polymer ranges from about 0.4 dL/g to about 1 dL/g. For poly(caprolactone), the inherent viscosity of the polymer ranges from about 0.5 dL/g to about 1.5 dL/g. In certain embodiments, the inherent viscosity of the poly(caprolactone) ranges from about 1.0 dL/g to about 1.5 dL/g. In certain embodiments, the inherent viscosity of the poly(caprolactone) ranges from about 1.0 dL/g to about 1.2 dL/g. In certain embodiments, the inherent viscosity of the poly(caprolactone) is about 1.08 dL/g.

Natural polymers, including collagen, polysaccharides, agarose, glycosaminoglycans, alginate, chitin, and chitosan, may also be employed. Tyrosine-based polymers, including but not limited to polyarylates and polycarbonates, may also be employed (Pulapura, et al., "Tyrosine-derived polycarbonates: Backbone-modified "pseudo"-poly(amino acids) designed for biomedical applications," *Biopolymers,* 1992, 32: 411-417; Hooper, et al., "Diphenolic monomers derived from the natural amino acid α-L-tyrosine: an evaluation of peptide coupling techniques," *J. Bioactive and Compatible Polymers,* 1995, 10:327-340, the contents of both of which are incorporated herein by reference). Monomers for tyrosine-based polymers may be prepared by reacting an L-tyrosine-derived diphenol compound with phosgene or a diacid (Hooper, 1995; Pulapura, 1992). Similar techniques may be used to prepare amino acid-based monomers of other amino acids having reactive side chains, including imines, amines, thiols, and the like. In one embodiment, the degradation products include bioactive materials, biomolecules, small molecules, or other such materials that participate in metabolic processes.

Polymers may be manipulated to adjust their degradation rates. The degradation rates of polymers are well characterized in the literature (see *Handbook of Biodegradable Polymers,* Domb, et al., eds., Harwood Academic Publishers, 1997, the entire contents of which are incorporated herein by reference). In addition, increasing the cross-link density of a polymer tends to decrease its degradation rate. The cross-link density of a polymer may be manipulated during polymerization by adding a cross-linking agent or promoter. After polymerization, cross-linking may be increased by exposure to UV light or other radiation. Co-monomers or mixtures of polymers, for example, lactide and glycolide polymers, may be employed to manipulate both degradation rate and mechanical properties.

In some embodiments, the bone graft comprises biodegradable polymeric or non-polymeric material. In some embodiments, the biodegradable polymer may provide immediate release, or sustained release of the biologically active material. For example, the biodegradable polymer comprises polyether ether ketone (PEEK). In some embodiments, the bone graft may comprise one or more poly (alpha-hydroxy acids), polyglycolide (PG), polyethylene glycol (PEG) conjugates of poly (alpha-hydroxy acids), polyorthoesters (POE), polyaspirins, polyphosphagenes, collagen, hydrolyzed collagen, gelatin, hydrolyzed gelatin, fractions of hydrolyzed gelatin, elastin, starch, pre-gelatinized starch, hyaluronic acid, chitosan, alginate, albumin, fibrin, vitamin E analogs, such as alpha tocopheryl acetate, d-alpha tocopheryl succinate, D,L-lactide, or L-lactide, caprolactone, dextrans, vinylpyrrolidone, polyvinyl alcohol (PVA), PVA-g-PLGA, PEGT-PBT copolymer (polyactive), methacrylates, PEO-PPO-PAA copolymers, PLGA-PEO-PLGA, PEG-PLG, PLA-PLGA, poloxamer 407, PEG-PLGA-PEG triblock copolymers, POE, SAIB (sucrose acetate isobutyrate), polydioxanone, methylmethacrylate (MMA), MMA and N-vinylpyyrolidone, polyamide, oxycellulose, copolymer of glycolic acid and trimethylene carbonate, polyesteramides, polyether ether ketone, polymethylmethacrylate, silicone, hyaluronic acid, chitosan, or combinations thereof.

In some embodiments, the bone graft may not be fully biodegradable. For example, the bone graft may comprise polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon device, glass device, plastics, ceramics, methacrylates, poly (N-isopropylacrylamide), PEO-PPO-PEO (pluronics) or combinations thereof. Typically, these types of matrices may need to be removed after a certain amount of time.

In some embodiments, the bone graft comprises biodegradable polymers comprising one or more of poly(lactide-co-glycolide) (PLGA), polylactide (PLA), polyglycolide (PGA), D-lactide, D,L-lactide, L-lactide, D,L-lactide-co-ε-caprolactone, L-lactide-co-ε-caprolactone, D,L-lactide-co-glycolide-co-ε-caprolactone, poly(D,L-lactide-co-caprolactone), poly(L-lactide-co-caprolactone), poly(D-lactide-co-caprolactone), poly(D,L-lactide), poly(D-lactide), poly(L-lactide), poly(esteramide) or a combination thereof. In some embodiments, a biologically active material can be encapsulated in a biodegradable polymer.

In various embodiments, the particle size distribution of the biodegradable polymer may be about 10 micrometers, 13 micrometers, 85 micrometers, 100 micrometers, 151 micrometers, 200 micrometers and all subranges therebetween. In some embodiments, at least 75% of the particles have a size from about 10 micrometers to about 200 micrometers. In some embodiments, at least 85% of the particles have a size from about 10 micrometers to about 200 micrometers. In some embodiments, at least 95° % of the particles have a size from about 10 micrometers to about 200 micrometers. In some embodiments, all of the particles have a size from about 10 micrometers to about 200 micrometers. In some embodiments, at least 75% of the particles have a size from about 20 micrometers to about 180 micrometers. In some embodiments, at least 85% of the particles have a size from about 20 micrometers to about 180 micrometers. In some embodiments, at least 95% of the particles have a size from about 20 micrometers to about 180 micrometers. In some embodiments, all of the particles have a size from about 20 micrometers to about 180 micrometers.

In some embodiments, the bone graft comprises one or more polymers (e.g., PLA, PLGA, etc.) having a MW of from about 15,000 to about 150,000 Da or from about 25,000 to about 100,000 Da.

In some embodiments, the bone graft comprises at least one biodegradable material in a wt % of from about 99.5%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 76%, 75%, 74%, 73%, 72%, 71%, 70%, 65%, 60%, 55%, 50%, 45%, 35%, 25%, 20%, 15%, 10%, to about 5% based on the total weight of the bone graft. In some embodiments, the biodegradable polymer comprises a range of about 0.1% to about 20% based on the total weight of the bone graft. In some embodiments, the biodegradable polymer comprises a range of about 0.1% to about 15% based on the total weight of the bone graft. In some embodiments, the biodegradable polymer comprises 14%, 13%, 12%, 11%, 10%, 9%, 8%, 7%, 6%, or 5% based on the total weight of the bone graft.

In some embodiments, the biodegradable polymer is present in an amount of about 0.01 wt % to about 50 wt % or about 8.0 wt % to about 50 wt % of the bone graft. In some embodiments, the biodegradable polymer is present in an amount of about 0.1 wt % to about 10 wt %, about 10 wt % to about 20 wt %, about 20 wt % to about 30 wt %, about 30 wt % to about 40 wt %, or about 40 wt % to about 50 wt %. In other embodiments, the biodegradable polymer comprises 0.2 to 2% and the ceramic particles about 98 to 99.8% by weight of the bone graft.

Mannitol, trehalose, dextran, mPEG and/or PEG may be used as a plasticizer for the polymer. In some embodiments, the polymer and/or plasticizer may also be coated on the bone graft to provide a desired release profile. In some embodiments, the coating thickness may be thin, for example, from about 5, 10, 15, 20, 25, 30, 35, 40, 45 or 50 microns to thicker coatings 60, 65, 70, 75, 80, 85, 90, 95 or 100 microns to delay release of a biologically active material from the bone graft. In some embodiments, the range of the coating on the bone graft ranges from about 5 microns to about 250 microns or 5 microns to about 200 microns to delay release from the bone graft.

In various embodiments, the carrier material can be a metal, for example a biodegradable metal. The term "biodegradable metal" (BM) has been generally used to describe degradable metallic biomaterials for medical applications. Useful biodegradable metals include without limitation magnesium based BMs including pure magnesium, magnesium-calcium alloy, magnesium zinc alloy and iron based BMs include pure iron, iron manganese alloys.

In another embodiment, a magnesium alloy may include from about 90 to about 98 weight % magnesium, from about 0 to about 6 weight % aluminum, from about 0 to about 2 weight % zinc, and from about 0 to about 3% rare earth metal(s). In another embodiment, the magnesium alloy may be AE42, which includes 94 weight % magnesium, 4 weight % aluminum, and 2 weight % rare earth metal(s).

In various implementations, the bone material useful for the computer implemented method for producing the bone graft of this application and which can be used with a 3-D printer includes allograft, demineralized bone matrix fiber, demineralized bone chips or a combination thereof.

In accordance with some embodiments, the carrier material for use by the 3-D printer with, in or on a bone material may be supplemented, further treated, or chemically modified with one or more bioactive agents or bioactive compounds. Bioactive agent or bioactive compound, as used herein, refers to a compound or entity that alters, inhibits, activates, or otherwise affects biological or chemical events. For example, bioactive agents may include, but are not limited to, osteogenic or chondrogenic proteins or peptides; DBM powder; collagen, insoluble collagen derivatives, etc., and soluble solids and/or liquids dissolved therein; anti-AIDS substances; anti-cancer substances; antimicrobials and/or antibiotics such as erythromycin, bacitracin, neomycin, penicillin, polymycin B, tetracyclines, biomycin, chloromycetin, and streptomycins, cefazolin, ampicillin, azactam, tobramycin, clindamycin and gentamycin, etc.; immunosuppressants; anti-viral substances such as substances effective against hepatitis; enzyme inhibitors; hormones; neurotoxins; opioids; hypnotics; anti-histamines; lubricants; tranquilizers; anti-convulsants; muscle relaxants and anti-Parkinson substances; anti-spasmodics and muscle contractants including channel blockers; miotics and anti-cholinergics; anti-glaucoma compounds; anti-parasite and/or anti-protozoal compounds; modulators of cell-extracellular matrix interactions including cell growth inhibitors and antiadhesion molecules, vasodilating agents; inhibitors of DNA, RNA, or protein synthesis; anti-hypertensives; analgesics; anti-pyretics; steroidal and non-steroidal anti-inflammatory agents; anti-angiogenic factors; angiogenic factors and polymeric carriers containing such factors; anti-secretory factors; anticoagulants and/or antithrombotic agents; local anesthetics; prostaglandins; anti-depressants; anti-psychotic substances; anti-emetics; imaging agents; biocidal/biostatic sugars such as dextran, glucose, etc.; amino acids; peptides; vitamins; inorganic elements; co-factors for protein synthesis; endocrine tissue or tissue fragments; synthesizers; enzymes such as alkaline phosphatase, collagenase, peptidases, oxidases and the like; polymer cell scaffolds with parenchymal cells; collagen lattices; antigenic agents; cytoskeletal agents; cartilage fragments; living cells such as chondrocytes, bone marrow cells, mesenchymal stem cells; natural extracts; genetically engineered living cells or otherwise modified living cells; expanded or cultured cells; DNA delivered by plasmid, viral vectors, or other member; tissue transplants; autogenous tissues such as blood, serum, soft tissue, bone marrow, or the like; bioadhesives; bone morphogenetic proteins (BMPs); osteoinductive factor (IFO); fibronectin (FN); endothelial cell growth factor (ECGF); vascular endothelial growth factor (VEGF); cementum attachment extracts (CAE); ketanserin; human growth hormone (HGH); animal growth hormones; epidermal growth factor (EGF); interleukins, for example, interleukin-1 (IL-1), interleukin-2 (IL-2); human alpha thrombin; transforming growth factor (TGF-beta); insulin-like growth factors (IGF-1 IGF-2); parathyroid hormone (PTH), platelet derived growth factors (PDGF); fibroblast growth factors (FGF, BFGF, etc.); periodontal ligament chemotactic factor (PDLGF); enamel matrix proteins; growth and differentiation factors (GDF); hedgehog family of proteins; protein receptor molecules; small peptides derived from growth factors above; bone promoters; cytokines; somatotropin; bone digesters; antitumor agents; cellular attractants and attachment agents; immuno-suppressants; permeation enhancers, for example, fatty acid esters such as laureate, myristate and stearate monoesters of polyethylene glycol, enamine derivatives, alpha-keto aldehydes; and nucleic acids.

In certain embodiments, the bioactive agent may be a drug, a growth factor, a protein or a combination thereof. In some embodiments, the bioactive agent may be a growth factor, cytokine, extracellular matrix molecule, or a fragment or derivative thereof, for example, a protein or peptide sequence such as RGD.

In some embodiments, the polymer may have a modulus of elasticity in the range of from about $1 \times 10^2$ dynes/cm$^2$ to about $6 \times 10^5$ dynes/cm$^2$, or $2 \times 10^4$ to about $5 \times 10^5$ dynes/cm$^2$, or $5 \times 10^4$ to about $5 \times 10^5$ dynes/cm$^2$.

Microspheres in the Carrier Material

In some embodiments, the bioactive agent included in the carrier material for use by the 3-D printer may be entrapped in a microsphere or polymer beads prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nanoparticles and nanocapsules) or in macroemulsions. Such techniques are disclosed in Remington's Pharmaceutical Sciences, 16th edition, Osol, A. Ed. (1980).

In certain implementations, the microspheres incorporated into the carrier material are from about 1 µm to about 750 µm diameter in size. In other implementations the microspheres can vary from about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, to about 750 µm diameter in size. In yet other aspects, the microspheres are porous and comprise pores having a size from about 1 µm to about 100 µm. By adding a known amount of bioactive agent to the microspheres or polymer beads present in the carrier material during the formation of the bone graft by 3-D printing, it is possible to control the delivery mechanism of the bioactive agent from the bone graft in a graded fashion preventing too much of the bioactive agent to be released all at once.

In other aspects, a 3-D printer can prepare a 3-D bone graft by combining a carrier material containing microspheres including bioactive agents and a bone material, wherein the bone graft is printed on a substrate that has load bearing strength, for example, a biocompatible or biodegradable metal or other non-metallic graft. In various aspects, the microspheres of the carrier material can include additional additives, for examples drugs, growth factors, proteins or a combination thereof.

Curable Ink

In several implementations, the carrier material comprises an ink that dries, is cured or reacts to form a porous, biodegradable, biocompatible material that is osteoinductive and has a load bearing strength comparable to bone. The ink can, in some aspects, be supplied in the form of a precursor powder and a precursor liquid. These may be fed to separate containers in the 3-D printer. Prior to printing, a quantity of the precursor powder and the precursor liquid may be mixed to form the ink to be used for printing the custom bone graft. The printing may be accomplished by delivering quantities of the ink via a suitably sized print nozzle that may be moved in a raster scan with respect to the custom bone graft being printed.

The precursor powder of the ink can contain a variety of ingredients such as, but not limited to, demineralized allograft bone matrix (DMB), a radical polymerization initiator, for example, dibenzoyl peroxide or some combination thereof. The precursor liquid may contain a variety of ingredients such as, for example, methyl methacrylate (MMA), a radiopaque compound, an antibiotic, and a compound to increase the biodegradability, or a combination thereof. In some aspects, a radiopaque compound can be, without limitations, zirconium dioxide or barium sulfate or a combination thereof. In other aspects, useful antibiotics include without limitation amoxicillin, doxycycline, gentamicin, clindamycin or a combination thereof. Other additives which may increase the biodegradability of the ink include, without limitation, cellulose acetate (CA), cellulose acetate phthalate (CAP) or a combination thereof.

In alternate embodiments, the ink may include synthetic bone substitutes, and other slow reabsorbing biocompatible, bioactive adhesives as discussed above. Examples of artificial bone substitutes include without limitation hydroxyapatite, synthetic calcium phosphate ceramic or a combination thereof. These may be used instead of, or with natural bone particulates such as without limitation allograft, fully demineralized bone fibers and surface demineralized bone chips, or a combination thereof. These may be used with synthetically produced bone morphogenetic agents such as, without limitation, recombinant human bone morphogenetic protein rhBMP-2. Alternative inks may also include other biocompatible, bioactive adhesives such as, for example, glass polyalkenoate cements, oleic methyl ester based adhesives, or a combination thereof.

In accordance with other embodiments, the carrier material for use by the 3-D printer with, in or on a bone material may be supplemented with other microparticles and/or nanoparticles which can be incorporated before or during 3-D printing in order to impart certain desirable mechanical, magnetic, piezoelectric properties and/or stimulate cellular functions upon implantation under a variety of in vivo or in vitro conditions to the custom made bone graft described in this disclosure.

Sterilization of the Bone Graft

In various aspects, the 3-D printed bone grafts obtained by the methods of this application can be terminally sterilized as they are formed, during the curing process or in the final packaging step. In various embodiments, one or more components of the bone graft may be sterilizable by radiation in a terminal sterilization step in the final packaging. Terminal sterilization of a product provides greater assurance of sterility than from processes such as an aseptic process, which require individual product components to be sterilized separately and the final package assembled in a sterile environment.

In various embodiments, gamma radiation is used in the terminal sterilization step, which involves utilizing ionizing energy from gamma rays that penetrates deeply into the bone graft. Gamma rays are highly effective in killing microorganisms, they leave no residues nor have sufficient energy to impart radioactivity to the bone graft. Gamma rays can be employed when the bone graft is in the package and gamma sterilization does not require high pressures or vacuum conditions, thus, package seals and other components are not stressed. In addition, gamma radiation eliminates the need for permeable packaging materials.

In some embodiments, the bone graft may be packaged in a moisture resistant package and then terminally sterilized by gamma irradiation. In use, the surgeon removes one or all components from the sterile package for use.

In various embodiments, electron beam (e-beam) radiation may be used to sterilize one or more components of the bone graft. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity.

Other methods may also be used to sterilize the bone graft and/or one or more components of the bone graft, including, but not limited to, gas sterilization, such as, for example, with ethylene oxide or steam sterilization.

Composite Ink

In various embodiments, an ink for use with a 3-D printer system described herein is a composite ink. In some aspects, the 3-D printer can use as ink a composite filament comprising a polymer and chips, microparticles, nanoparticles and/or fibers of demineralized bone, non-demineralized bone or a combination thereof. In some embodiments, the composite filament comprises a bioerodible polymer, one or more ceramics and demineralized bone matrix (DBM) where the demineralized bone matrix particles are embedded within or coated on the surface of the bioerodible polymer and ceramic particles. In a further embodiment, the demineralized bone matrix particles are dispersed throughout the bioerodible polymer and ceramic particles. In some embodiments, the demineralized bone matrix particles are dispersed homogeneously throughout the polymer and ceramic particles.

In certain embodiments, the composite filament comprises a combination of fibers of demineralized bone matrix from allograft bone and fibers of non-allograft bone material, the fibers of non-allograft bone material comprising non-fibrous demineralized bone matrix particles embedded within or disposed on the fibers of the non-allograft bone material.

In other embodiments, the fibers of non-allograft bone material comprise a bioerodible polymer and one or more ceramics either alone or in combination. In some embodiments, the fibers of non-allograft bone material comprise ceramics and collagen, hyaluronic acid, chitosan, keratin, and derivatives thereof, either alone or in combination. In some embodiments, the bioerodible polymer is collagen. In some embodiments, the collagen is porous. In other embodiments, the diameter of the fibers of allograft bone and non-allograft bone material is between about 50 μm and about 1 mm. In some embodiments, the diameter of the fibers of allograft bone and non-allograft bone material is between about 75 nm and about 250 nm. In some embodiments, the length of the fibers of the allograft bone and non-allograft material is between about 5 mm and about 30 mm. In some embodiments, the composite filament composition contains a bioactive agent. In some embodiments, the ceramic is a calcium phosphate ceramic and/or a silicon ceramic. In other embodiments, the ceramic is tricalcium phosphate. In some embodiments, the ratio of fibers of demineralized bone matrix from allograft bone to fibers of non-allograft material ranges from about 80:20 to about 70:30, or from about 40:60 to about 60:40. In some embodiments, the ratio of fibers of demineralized bone matrix from allograft bone to fibers of non-allograft material is about 50:50. In some embodiments, the non-fibrous demineralized bone matrix particles embedded within or disposed on the fibers of the non-allograft bone material range in diameter size from between about 50 μm and about 30 mm.

The fibers of the non-allograft bone material comprises a bioerodible polymer and a synthetic ceramic to which demineralized bone matrix particles are embedded either within and/or on the surface of the non-allograft bone material. The demineralized bone matrix particles are non-fibrous. In other embodiments, the particles are powders, microspheres, sponges, pastes, gels, and/or granules. In one embodiment, the particles are powders.

DBM particles for use in the present disclosure can be obtained commercially or can be prepared by known techniques. In general, advantageous, osteoinductive DBM materials can be prepared by decalcification of cortical and/or cancellous bone, often by acid extraction. This process can be conducted so as to leave collagen, noncollagenous proteins, and growth factors together in a solid matrix. Methods for preparing such bioactive demineralized bone matrix are known, in respect of which reference can be made to U.S. Pat. Nos. 5,073,373, 5,484,601; and 5,284,655, as examples. DBM products are also available commercially, including for instance, from sources such as Regeneration Technologies, Inc. (Alachua, Fla.), The American Red Cross (Arlington, Va.), and others. For the purposes of this disclosure, any shape and particle size of DBM can be used, including DBM in the form of fragments, slices, pellets, shavings, granules, chips, fibers, or powder a well as demineralized whole bones. In various embodiments, the demineralized bone is of a small particle size, and in the form of powder. In certain embodiments, the particulate DBM material can have an average particle size of less than about 100 to about 1000 microns. For instance, the DBM material can have particle sizes in the range of 50 to 850 microns. DBM materials that are solely osteoconductive can be prepared using similar techniques that have been modified or supplemented to remove or inactivate (e.g., by crosslinking or otherwise denaturing) components in the bone matrix responsible for osteoinductivity. Osteoinductive and/or osteoconductive DBM materials used in the present disclosure can be derived from human donor tissue, especially in regard to implant devices intended for use in human subjects.

In regard to the incorporated materials considered on a dry weight basis, the particulate DBM material, which are embedded onto the non-allograft fibers can constitute about 10% to about 50% of the compositions, about 20% to about 40%, and about 25% to about 35% by weight. In various embodiments, particulate DBM material embedded onto the non-allograft fibers can constitute about 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49% or about 50% of the composite filament. In a similar vein, composite filaments can contain about 5% to about 30% by weight insoluble collagen particulate on a dry weight basis, about 8% to about 20%, or about 10% to about 15%; and can contain the ceramics at a level of about 1% to about 200,% on a dry weight basis, about 5% to about 15%, or about 8% to about 12%. It will be understood, however, that other amounts of these materials can be used within the broader aspects of the present disclosure.

In some embodiments, the demineralized bone fibers of allograft bone and fibers of non-allograft bone have an average length to average thickness ratio or aspect ratio of the fibers from about 50:1 to about 1000:1. In overall appearance, the elongated demineralized bone fibers can be in the form of threads, narrow strips, and/or thin sheets. The elongated demineralized bone fibers can be substantially linear in appearance or they can be coiled to resemble springs. In some embodiments, the elongated demineralized bone fibers are of irregular shapes including, for example, linear, serpentine and/or curved shapes. The elongated bone fibers can be demineralized however some of the original mineral content may be retained when desirable for a particular embodiment. The bone graft composition of the composite filament may further comprise mineralized bone particles.

The bioerodible polymer will exhibit dissolution when placed in a mammalian body and may be hydrophilic (e.g., collagen, hyaluronic acid, polyethylene glycol). Synthetic polymers are suitable according to the present disclosure, as they are biocompatible and available in a range of copolymer ratios to control their degradation.

In some embodiments, hydrophobic polymers (e.g., poly(lactide-co-glycolyde), polyanhydrides) may be used. Alternatively, a combination of hydrophilic and hydrophobic polymers may be used in the bone graft composition of the disclosure.

Exemplary materials may include biopolymers and synthetic polymers such as human skin, human hair, bone, collagen, fat, thin cross-linked sheets containing fibers and/or fibers and chips, polyethylene glycol (PEG), chitosan, alginate sheets, cellulose sheets, hyaluronic acid sheets, as well as copolymer blends of poly (lactide-co-glycolide) PLGA.

In some embodiments, the particles disclosed herein can also include other biocompatible and bioresorbable substances. These materials may include, for example, natural polymers such as proteins and polypeptides, glycosaminoglycans, proteoglycans, elastin, hyaluronic acid, dermatan sulfate, gelatin, or mixtures or composites thereof. Synthetic polymers may also be incorporated into the bone graft composites. These include, for example biodegradable synthetic polymers such as polylactic acid, polyglycolide, polylactic polyglycolic acid copolymers ("PLGA"), polycaprolactone ("PCL"), poly(dioxanone), poly(trimethylene carbonate) copolymers, polyglyconate, poly(propylene fumarate), poly(ethylene terephthalate), poly(butylene terephthalate), polyethylene glycol, polycaprolactone copolymers, polyhydroxybutyrate, polyhydroxyvalerate, tyrosine-derived polycarbonates and any random or (multi-)block copolymers, such as bipolymer, terpolymer, quaterpolymer, that can be polymerized from the monomers related to previously-listed homo- and copolymers.

In some embodiments, the bioerodible polymer is collagen. Collagen has excellent histocompatibility without antibody formation or graft rejection. Any suitable collagen material may be used, including known collagen materials, or collagen materials as disclosed in U.S. patent application Ser. No. 12/030,181, filed Feb. 12, 2008, hereby incorporated by reference in its entirety. Various collagen materials can be used, alone or in combination with other materials.

Insoluble collagen material for use in the disclosure can be derived from natural tissue sources, (e.g., xenogenic, allogenic, or autogenic relative to the recipient human or other patient) or recombinantly prepared. Collagens can be subclassified into several different types depending upon their amino acid sequence, carbohydrate content and the presence or absence of disulfide crosslinks. Types I and III collagen are two of the most common subtypes of collagen and may be used in the present disclosure. Type I collagen is present in skin, tendon and bone, whereas Type III collagen is found primarily in skin. The collagen used in compositions of the disclosure can be obtained from skin, bone, tendon, or cartilage and purified by methods well known in the art and industry. Alternatively, the collagen can be purchased from commercial sources.

The collagen can be atelopeptide collagen and/or telopeptide collagen. Still further, either or both of non-fibrillar and fibrillar collagen can be used. Non-fibrillar collagen is collagen that has been solubilized and has not been reconstituted into its native fibrillar form.

Suitable collagen products are available commercially, including for example from Kensey Nash Corporation (Exton, Pa.), which manufactures a fibrous collagen known as Semed F, from bovine hides. Collagen materials derived from bovine hide are also manufactured by Integra Life Science Holding Corporation (Plainsboro, N.J.). Naturally-derived or recombinant human collagen materials are also suitable for use in the disclosure. Illustratively, recombinant human collagen products are available from Fibrogen, Inc. (San Francisco, Calif.).

The solid particulate collagen incorporated into the inventive compositions can be in the form of intact or reconstituted fibers, or randomly-shaped particles, for example. In certain embodiments, the solid particulate collagen will be in the form of particles derived from a sponge material, for example by randomly fragmenting the sponge material by milling, shredding or other similar operations. Such particulated sponge material can have an average maximum particle diameter of less than about 6 mm, less than about 3 mm, or in the range of about 0.5 mm to 2 mm. Such materials can, for example, be obtained by milling or grinding a porous sponge material and sieving the milled or ground material through a screen having openings sized about 6 mm or smaller, or about 0.5 mm to about 2 mm. Retch grinders with associated sieves are suitable for these purposes. Other sources of chemically crosslinked, particulate collagen, in fiber, irregular or other shapes, can also be used, and their use is considered to be another aspect of the present disclosure. These crosslinked particulate materials can be provided as starting materials for preparing composite compositions as disclosed herein, and therefore as incorporated in the bone graft, these particles are individually crosslinked. Crosslinked solid collagen particles can be used in combination with non-crosslinked collagen in compositions of the disclosure, wherein the non-crosslinked collagen can be solid (insoluble) or soluble collagen, or combinations thereof. Such crosslinked and non-crosslinked collagen mixtures can be used, for example, to modulate the residence time of the collagen portion of the bone graft compositions in vivo.

Suitable crosslinking agents include, but are not limited to, mono- and dialdehydes, including glytaraldehyde and formaldehyde; polyepoxy compounds such as glycerol; and sugars such as glucose. In one embodiment, the crosslinking agent is glycerol.

Exemplary collagen particles can be obtained from various collagen sources including human or non-human (bovine, ovine, and/or porcine), as well as recombinant collagen or combinations thereof. Examples of suitable collagen include, but are not limited to, human collagen type I, human collagen type II, human collagen type III, human collagen type IV, human collagen type V, human collagen type VI, human collagen type VII, human collagen type VIII, human collagen type IX, human collagen type X, human collagen type XI, human collagen type XII, human collagen type XIII, human collagen type XIV, human collagen type XV, human collagen type XVI, human collagen type XVII, human collagen type XVIII, human collagen type XIX, human collagen type XXI, human collagen type XXII, human collagen type XXIII, human collagen type XXIV, human collagen type XXV, human collagen type XXVI, human collagen type XXVII, and human collagen type XXVIII, or combinations thereof. Collagen further may comprise hetero- and homo-trimers of any of the above-recited collagen types. In some embodiments, the collagen comprises hetero- or homo-trimers of human collagen type I, human collagen type II, human collagen type III, or combinations thereof. In some embodiments, the collagen is porous.

In some embodiments, the bioerodible polymer may be hyaluronic acid, chitosan, chitin, keratin, cellulose, glycosaminoglycans and derivatives thereof (e.g. esters of hyaluronic acid) or others of synthetic origin which may be used as an alternative to or in combination with collagen.

In some embodiments, the synthetic ceramics disclosed herein may be selected from one or more materials comprising calcium phosphate ceramics or silicon ceramics. Biological glasses such as calcium-silicate-based bioglass, silicon calcium phosphate, tricalcium phosphate (TCP), biphasic calcium phosphate, calcium sulfate, hydroxyapatite, coralline hydroxyapatite, silicon carbide, silicon nitride ($Si_3N_4$), and biocompatible ceramics may be used. In some embodiments, the ceramic is tri-calcium phosphate or biphasic calcium phosphate and silicon ceramics. In some embodiments, the ceramic is tricalcium phosphate.

In some embodiments, the ceramics are a combination of a calcium phosphate ceramic and a silicon ceramic. In some embodiments, the calcium phosphate ceramic is resorbable biphasic calcium phosphate (BCP) or resorbable tri-calcium phosphate (TCP).

Biphasic calcium phosphate can have a tricalcium phosphate:hydroxyapatite weight ratio of about 50:50 to about 95:5, about 70:30 to about 95:5, about 80:20 to about 90:10, or about 85:15. The mineral material can be a granular particulate having an average particle diameter between about 0.2 and 5.0 mm, between about 0.4 and 3.0 mm, or between about 0.4 and 2.0 mm.

The ceramics of the disclosure may also be oxide ceramics such as alumina ($Al_2O_3$) or zirconia ($ZrO_2$) or composite combinations of oxides and non-oxides such as silicon nitride.

The ceramics of the disclosure may be porous and may have pore sizes large enough to permit osteoinduction via invasion of the material by bone forming cells. Examples of porous ceramics are hydroxyapatite and TCP.

In some embodiments, the non-allograft bone material includes from about 40 to about 60 weight percent collagen, from about 20 to about 50 weight percent DBM, and from about 10 to about 50 weight percent ceramics. In some embodiments, the ratio of DBM particles to collagen and/or ceramics is about 5:1, about 4:1, about 3:1, about 2:1, about 1:1, about 1:5, about 1:4, about 1:3, or about 1:2. In some embodiments, the ratio of DBM particles to collagen and/or ceramics is about 1.5:0.5, about 1:1, or about 0.5:1.5.

In some embodiments, the particles disclosed herein also include synthetic ceramics that are effective to provide a scaffold for bone growth and which are completely bioresorbable and biocompatible. The synthetic ceramics should provide high local concentrations of calcium, phosphate and silicon ions that act as a nidus for de-novo bone formation. The use of such resorbable ceramics provides many advantages over alternative conventional materials. For instance, it eliminates the need for post-therapy surgery for removal and degrades in the human body to biocompatible, bioresorbable products.

In other embodiments, the composite filament for use in a 3-D printer system described herein is a curable composite ink. The composite ink comprises a curable material and, optionally a colorant dispersed in the ink, in amount from about 0.01 to about 5% by weight of the composite ink. In some cases, the colorant is present in the composite ink in an amount between about 0.01 and 3 weight %, between about 0.01 and 1 weight %, between about 0.05 and 5 weight %, between about 0.05 and 3 weight %, between about 0.05 and 1 weight %, between about 0.1 and 5 weight %, between about 0.1 and 3 weight %, or between about 0.1 and 1 weight %. In some aspects, the colorant of a composite ink comprises an inorganic pigment, such as $TiO_2$ and ZnO. In some embodiments, the colorant of a composite ink comprises a colorant for use in a RGB, sRGB, CMY, CMYK, L*a*b*, or Pantone® colorization scheme. Moreover, in some cases, a particulate colorant described herein has an average particle size of less than 500 nm, such as an average particle size of less than 400 nm, less than 300 nm, less than 250 nm, less than 200 nm, or less than 150 nm. In some instances, a particulate colorant has an average particle size of 50-1000 nm, 50-500 nm, 50-400 nm, 50-300 nm, 50-200 nm, 70-500 nm, 70-300 nm, 70-250 nm, or 70-200 nm.

In certain embodiments, the curable material included in the composite filament is present in an amount up to about 99 weight %, up to about 95 weight %, up to about 90 weight %, or up to about 80 weight %, based on the total weight of the composite ink. In some cases, a composite ink described herein comprises about 10-95 weight % curable material based on the total weight of the carrier ink. In some embodiments, a carrier ink comprises about 20-80 weight % curable material, about 30-70 weight % curable material, or about 70-90 weight % curable material.

In some cases, a curable material comprises one or more polymerizable components. As used herein, a polymerizable component comprises a component that can be polymerized or cured to provide a 3-D printed article or object. In some embodiments, polymerizing or curing comprises irradiating with electromagnetic radiation having sufficient energy to initiate a polymerization or cross-linking reaction. In other embodiments, ultraviolet (UV) radiation can be used.

In some embodiments, a polymerizable component comprises a monomeric chemical species, such as a chemical species having one or more functional groups or moieties that can react with the same or different functional groups or moieties of another monomeric chemical species to form one or more covalent bonds, such as in a polymerization reaction. A polymerization reaction, in some embodiments, comprises a free radical polymerization, such as that between points of unsaturation, including points of ethylenic unsaturation. In some embodiments, a polymerizable component comprises at least one ethylenically unsaturated moiety, such as a vinyl group or allyl group. In some embodiments, a polymerizable component comprises an oligomeric chemical species capable of undergoing additional polymerization, such as through one or more points of unsaturation as described herein. In other embodiments, a polymerizable component comprises one or more monomeric chemical species and one or more oligomeric chemical species as described herein. A monomeric chemical species and/or an oligomeric chemical species described herein can have one polymerizable moiety or a plurality of polymerizable moieties.

In some embodiments, a polymerizable component comprises one or more photo-polymerizable or photo-curable chemical species. A photo-polymerizable chemical species, in some embodiments, comprises a UV-polymerizable chemical species. In some embodiments, a polymerizable component is photo-polymerizable or photo-curable at wavelengths ranging from about 300 nm to about 400 nm. Alternatively, in some embodiments, a polymerizable component is photo-polymerizable at visible wavelengths of the electromagnetic spectrum.

In some embodiments, a polymerizable component described herein comprises one or more species of (meth) acrylates including acrylate or methacrylate or mixtures or combinations thereof. In other embodiments, a polymerizable component comprises an aliphatic polyester urethane acrylate oligomer, a urethane (meth)acrylate resin, and/or an acrylate amine oligomeric resin, such as EBECRYL 7100. In yet other embodiments, a UV polymerizable or curable resin or oligomer can comprise any methacrylate or acrylate resin which polymerizes in the presence of a free radical photoinitiator, is thermally stable in an exposed state for at least one week at a jetting temperature and for at least 4 weeks in an enclosed state, and/or has a boiling point greater than the jetting temperature. In some embodiments, a polymerizable component has a flash point above the jetting temperature.

Urethane (meth)acrylates suitable for use in inks described herein, in some embodiments, can be prepared in a known manner, typically by reacting a hydroxyl-terminated urethane with acrylic acid or methacrylic acid to give the corresponding urethane (meth)acrylate, or by reacting an isocyanate-terminated prepolymer with hydroxyalkyl acrylates or methacrylates to give the urethane (meth)acrylate. The weight average molecular weight of such (meth)acrylate oligomers is generally in the range from about 400 to 10,000, or from about 500 to 7,000. Urethane (meth)acrylates are commercially available from the SARTOMER Company under the product names CN980, CN981, CN975 and CN2901, or from Bomar Specialties Co. (Winsted, Conn.) under the product name BR-741. In some embodiments, a urethane (meth)acrylate oligomer has a viscosity ranging from about 140,000 cP to about 160,000 cP at about 50° C. or from about 125,000 cP to about 175,000 cP at about 50° C. when measured in a manner consistent with ASTM D2983. In some embodiments described herein, a urethane (meth)acrylate oligomer has a viscosity ranging from about 100,000 cP to about 200,000 cP at about 50° C. or from about 10,000 cP to about 300,000 cP at about 50° C. when measured in a manner consistent with ASTM D2983.

In various embodiments, a polymerizable component comprises one or more low molecular weight materials, such as methacrylates, dimethacrylates, triacrylates, and diacrylates, which can be used in a variety of combinations. In some embodiments, for example, a polymerizable component comprises one or more of tetrahydrofurfuryl methacrylate, triethylene glycol dimethacrylate, 2-phenoxyethyl methacrylate, lauryl methacrylate, ethoxylated trimethylolpropane triacrylate, tricyclodecane dimethanol diacrylate, 2-phenoxyethylacrylate, triethylene glycol diacrylate, a monofunctional aliphatic urethane acrylate, polypropylene glycol monomethacrylate, polyethylene glycol monomethacrylate, cyclohexane dimethanol diacrylate, and tridecyl methacrylate.

In some embodiments, a polymerizable component comprises diacrylate and/or dimethacrylate esters of aliphatic, cycloaliphatic or aromatic diols, including 1,3- or 1,4-butanediol, neopentyl glycol, 1,6-hexanediol, diethylene glycol, triethylene glycol, tetraethylene glycol, polyethylene glycol, tripropylene glycol, ethoxylated or propoxylated neopentyl glycol, 1,4-dihydroxymethylcyclohexane, 2,2-bis (4-hydroxycyclohexyl)propane or bis(4-hydroxycyclohexyl)methane, hydroquinone, 4,4'-dihydroxybiphenyl, bisphenol A, bisphenol F, bisphenol S, ethoxylated or propoxylated bisphenol A, ethoxylated or propoxylated bisphenol F or ethoxylated or propoxylated bisphenol S.

A polymerizable component, in some embodiments, comprises one or more tri(meth)acrylates. In some embodiments, tri(meth)acrylates comprise 1,1-trimethylolpropane triacrylate or methacrylate, ethoxylated or propoxylated 1,1,1-trimethylolpropanetriacrylate or methacrylate, ethoxylated or propoxylated glycerol triacrylate, pentaerythritol monohydroxy triacrylate or methacrylate, or tris(2-hydroxy ethyl) isocyanurate triacrylate.

In other embodiments, a polymerizable component of the composite filament described herein comprises one or more higher functional acrylates or methacrylates such as dipentaerythritol monohydroxy pentaacrylate or bis(trimethylolpropane) tetraacrylate. In some embodiments, a (meth) acrylate of an ink has a molecular weight ranging from about 250 to 700.

In certain embodiments, a polymerizable component comprises allyl acrylate, allyl methacrylate, methyl (meth) acrylate, ethyl (meth)acrylate, n-propyl (meth)acrylate, n-butyl (meth)acrylate, isobutyl (meth)acrylate, n-hexyl (meth)acrylate, 2-ethylhexyl (meth)acrylate, n-octyl (meth) acrylate, n-decyl (meth)acrylate and n-dodecyl (meth)acrylate, 2-hydroxyethyl (meth)acrylate, 2- and 3-hydroxypropyl (meth)acrylate, 2-methoxyethyl(meth)acrylate, 2-ethoxyethyl (meth)acrylate and 2- or 3-ethoxypropyl (meth)acrylate, tetrahydrofurfuryl methacrylate, 2-(2-ethoxyethoxyl) ethyl acrylate, cyclohexyl methacrylate, 2-phenoxyethyl acrylate, glycidyl acrylate, isodecyl acrylate, or a combination thereof.

Additional non-limiting examples of species of polymerizable components useful in some embodiments described herein include the following: isobornyl acrylate (IBOA), commercially available from SARTOMER under the trade name SR 506A; isobornyl methacrylate, commercially available from SARTOMER under the trade name SR 423A; alkoxylated tetrahydrofurfuryl acrylate, commercially available from SARTOMER under the trade name SR 611; monofunctional urethane acrylate, commercially available from RAHN USA under the trade name GENOMER 1122; aliphatic urethane diacrylate, commercially available from ALLNEX under the trade name EBECRYL 8402; triethylene glycol diacrylate, commercially available from SARTOMER under the trade name SR 272; triethylene glycol dimethacrylate, commercially available from SARTOMER under the trade name SR 205; tricyclodecane dimethanol diacrylate, commercially available from SARTOMER under the trade name SR 833S; tris(2-hydroxy ethyl)isocyanurate triacrylate, commercially available from SARTOMER under the trade name SR 368; and 2-phenoxyethyl acrylate, commercially available from SARTOMER under the trade name SR 339. Other commercially available curable materials may also be used.

The composite filament ink useful for the 3-D printing system described in this disclosure can also include one or more additives selected from the group consisting of photoinitiators, inhibitors, stabilizing agents, sensitizers, and combinations thereof. In some embodiments, suitable photoinitiators comprise benzoins, including benzoin, benzoin ethers, such as benzoin methyl ether, benzoin ethyl ether and benzoin isopropyl ether, benzoin phenyl ether and benzoin acetate, acetophenones, including acetophenone, 2,2-dimethoxyacetophenone and 1,1-dichloroacetophenone, benzil, benzil ketals, such as benzil dimethyl ketal and benzil diethyl ketal, anthraquinones, including 2-methylanthraquinone, 2-ethylanthraquinone, 2-tert-butylanthraquinone, 1-chloroanthraquinone and 2-amylanthraquinone, triphenylphosphine, benzoylphosphine oxides, for example 2,4,6-trimethylbenzoyldiphenylphosphine oxide (Lucirin TPO), benzophenones, such as benzophenone and 4,4'-bis(N,N'-dimethylamino)benzophenone, thioxanthones and xanthones, acridine derivatives, phenazine derivatives, quinoxaline derivatives or 1-phenyl-1,2-propanedione, 2-O-benzoyl oxime, 1-aminophenyl ketones or 1-hydroxyphenyl ketones, such as 1-hydroxycyclohexyl phenyl ketone, phenyl 1-hydroxyisopropyl ketone and 4-isopropylphenyl 1-hydroxyisopropyl ketone.

In some cases, suitable photoinitiators comprise those operable for use with a HeCd laser radiation source, including acetophenones, 2,2-dialkoxybenzophenones and 1-hydroxyphenyl ketones, such as 1-hydroxycyclohexyl phenyl ketone or 2-hydroxyisopropyl phenyl ketone (2-hydroxy-2,2-dimethylacetophenone). Additionally, in other aspects, suitable photoinitiators comprise those operable for use with an Ar laser radiation source including benzil ketals, such as benzil dimethyl ketal. In some embodiments, a photoinitiator comprises an α-hydroxyphenyl ketone, benzil dimethyl ketal or 2,4,6-trimethylbenzoyldiphenylphosphine oxide or a mixture thereof.

Other suitable photoinitiators comprise ionic dye-counter ion compounds capable of absorbing actinic radiation and generating free radicals for polymerization initiation. In some embodiments, inks containing ionic dye-counter ion compounds can be cured more variably with visible light within the adjustable wavelength range of about 400 nm to about 700 nm.

A photoinitiator can be present in an ink described herein in any amount not inconsistent with the objectives of the present disclosure. In some embodiments, a photoinitiator is present in an ink in an amount of up to about 5 weight percent, based on the total weight of the ink. In some embodiments, a photoinitiator is present in an amount ranging from about 0.1 weight percent to about 5 weight percent.

In some embodiments, a method of printing a 3-D bone graft comprises selectively depositing layers of a composite ink described herein in a fluid state onto a substrate. For example, in some cases, the composite filament ink comprises a curable material and a colorant dispersed in the curable material in an amount of about 0.01 to 5 weight %, based on the total weight of the composite ink. Further, the layers of a composite filament ink can be deposited according to an image of the 3-D bone graft in a computer readable format. In some embodiments, the ink is deposited according to preselected computer aided design (CAD) parameters on to a metal or non-metal substrate.

Moreover, in some cases, one or more layers of a composite ink described herein have a thickness of about 0.03 to about 5 mm, a thickness of about 0.03 to about 3 mm, a thickness of about 0.03 to about 1 mm, a thickness of about 0.03 to about 0.5 mm, a thickness of about 0.03 to about 0.3 mm, a thickness of about 0.03 to about 0.2 mm, a thickness of about 0.05 to about 5 mm, a thickness of about 0.05 to about 1 mm, a thickness of about 0.05 to about 0.5 mm, a thickness of about 0.05 to about 0.3 mm, or a thickness of about 0.05 to about 0.2 mm. Other thicknesses are also possible.

A method described herein can also comprise curing the layers of the composite ink. In some embodiments, a method of printing a 3-D bone graft further comprises subjecting the ink to electromagnetic radiation of sufficient wavelength and intensity to cure the ink, where curing can comprise polymerizing one or more polymerizable functional groups of one or more components of the ink. In some embodiments of printing a 3-D bone graft, a layer of deposited ink is cured prior to the deposition of another or adjacent layer of ink.

In some embodiments, a preselected amount of ink described herein is heated to the appropriate temperature and jetted through the print head or a plurality of print heads of a suitable inkjet printer to form a layer on a print pad in a print chamber. In some embodiments, each layer of ink is deposited according to the preselected CAD parameters. A suitable print head to deposit the ink, in some embodiments, is a piezoelectric print head. Additional suitable print heads for the deposition of ink and support material described herein are commercially available from a variety of ink jet printing apparatus manufacturers. For example, Xerox, Hewlett Packard, or Ricoh print heads may also be used in some instances.

In some embodiments, a method of printing a 3-D article comprises using a composite ink, wherein the composite ink remains substantially fluid upon deposition. In other embodiments, the ink exhibits a phase change upon deposition and/or solidifies upon deposition. In some embodiments, the temperature of the printing environment can be controlled so that the jetted droplets of ink solidify on contact with the receiving surface. In other embodiments, the jetted droplets of ink do not solidify on contact with the receiving surface, remaining in a substantially fluid state. In some embodiments, after each layer is deposited, the deposited material is planarized and cured with electromagnetic (e.g., UV) radiation prior to the deposition of the next layer. Optionally, several layers can be deposited before planarization and curing, or multiple layers can be deposited and cured followed by one or more layers being deposited and then planarized without curing. Planarization corrects the thickness of one or more layers prior to curing the material by evening the dispensed material to remove excess material and create a uniformly smooth exposed or flat up-facing surface on the support platform of the printer.

In another embodiment, mechanical, magnetic, and/or piezoelectric sensitive micro-, nanoparticles or patterns are incorporated during 3-D printing to stimulate cellular functions upon implantation under a variety of in vivo or in vitro mechanical magnetic or pressure conditions.

Figure 11:
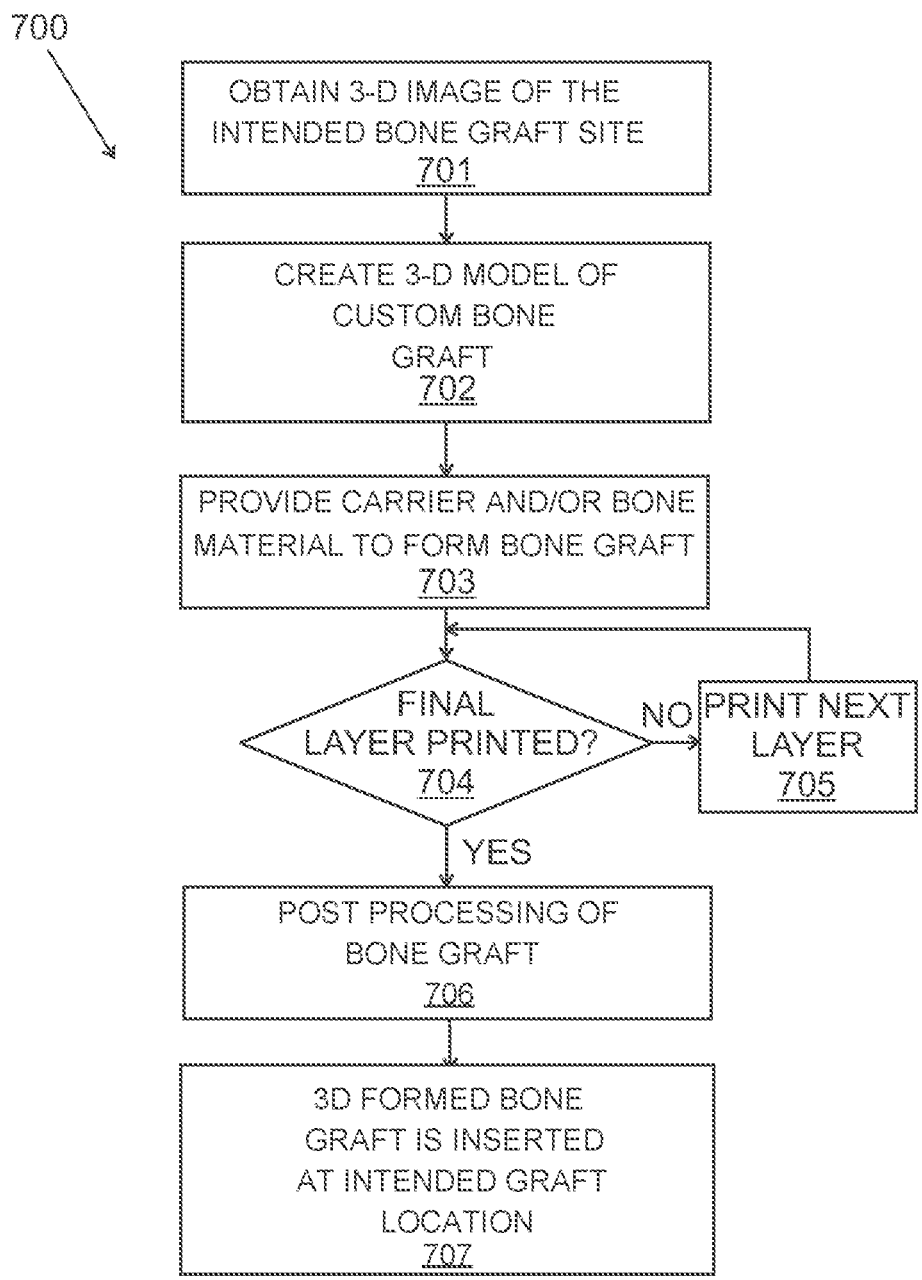
FIG. 11 is a flow diagram illustrating representative steps that the logic performs for producing a bone graft according to an embodiment of this application.

FIG. 11 is a flow diagram of representative steps of a method, a computer implemented method of producing a custom bone graft. The method includes step 701 for obtaining a 3-D image of the implant location or intended bone repair site including the topography of the bone repair site or mesh bag 70, or the location of mesh bag 70. Step 701 can be accomplished by using many known techniques of obtaining a 3-D image including, but not limited to, (i) one or more X-ray images; (ii) a computer aided design (CAD) program; (iii) a cone beam imaging device; (iv) a computed tomography (CT) scan device; (v) a magnetic resonance imaging (MRI); or a combination thereof. In step 702, the images obtained in step 701 may be inputted into a suitable digital data processor to create a 3-D model of a custom bone graft. In step 703, osteogenic material including, in some cases, polymers that preserves the biological activity of demineralized bone particles and/or fibers and has a load bearing structure is supplied to form ink that can be used in steps 704 and 705. The load bearing structure, in some aspects, can be a metal or non-metal structure. In step 704, the 3-D printer may first check to determine if the final layer has printed all the layers required to produce the custom bone graft.

These layers may have been provided by a programmed module operative on a digital data processing device, and may be the 3-D model of the custom bone graft reduced to consecutive slices that when printed in the correct order, may result in the desired bone graft.

In step 705, the 3-D printer may print the next layer if the final layer has not yet been printed. This may be done, for instance, by moving the print nozzle in a raster fashion, depositing ink where required. The printing is performed in a sterilized environment.

In step 706, once the 3-D printer has printed all the required layers that constitute the custom bone graft, the bone graft may undergo post print processing. This post processing step may, for instance, include actions such as, but not limited to, dissolving out the sucrose crystals, if any are present, to provide a porous structure and sterilization of the custom bone graft.

In step 707, the 3-D printed custom bone graft is removed and may now be inserted into the patient at the intended bone repair site.

Figure 12:
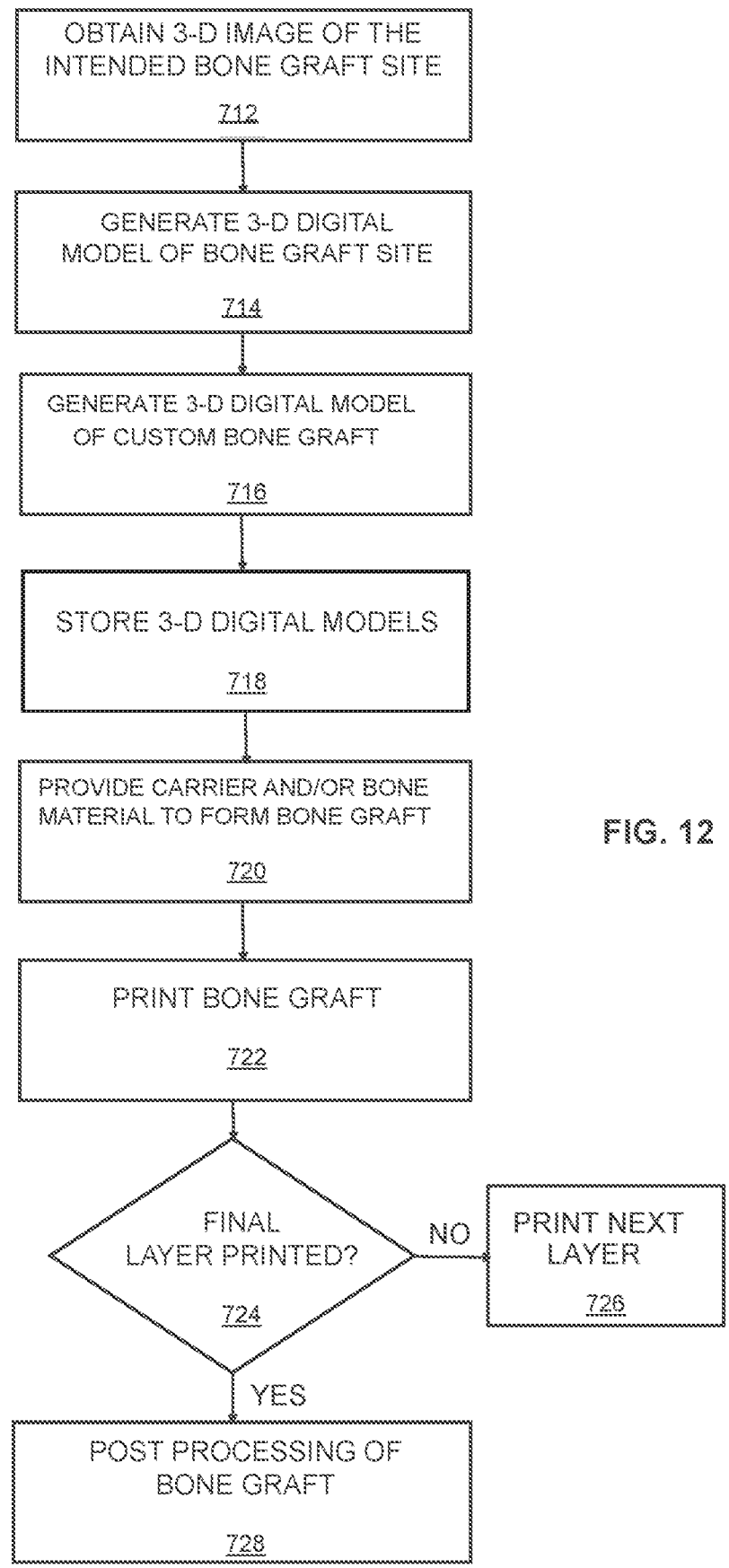
FIG. 12 is a flow diagram illustrating representative steps that the logic performs for producing a bone graft according to an embodiment of this application.

FIG. 12 is a flow diagram illustrating representative steps that the logic performs for producing a bone graft according to an embodiment of this application. The computer is programmed for 3-D printing of a bone graft by obtaining a 3-D image of an intended bone graft site, this can be by taking one or more X-ray images, a computer aided design (CAD) program, a cone beam imaging device, a computed tomography (CT) scan device, a magnetic resonance imaging (MRI) and the image can be scanned or input into the computer system in step 712. A 3-D digital model of the intended bone graft site is generated in step 714 based on the 3-D image of the intended bone graft site, the 3-D digital model of the bone graft site including a virtual depth, thickness and volume of the intended bone graft site. Based on the 3-D image of the intended bone graft site, a 3-D digital model of the custom bone graft is generated in step 716. For example, if the intended bone graft site has a bone defect, the computer will generate a virtual 3-D model of the bone graft including a virtual depth, thickness and volume of the bone graft that can fit within the bone defect. Thus, a variety of 3-D models of the bone graft can be generated that will fit within the bone defect. In some embodiments, the computer will create a variety of shapes and sizes of the bone graft that will fit within the bone defect and the user can select the desired shape. In this way, a custom bone graft can be selected. The computer will store the digital models in step 718 on the database.

The computer processor will have instructions to retrieve the stored 3-D digital model of the bone graft and combine a carrier material with, in or on the bone material based on the stored 3-D digital model of the bone graft in step 720. Thus, the computer will control the amount of bone material and/or carrier used in the printing process either in one or more printing heads to print the bone graft in step 722. The carrier in an ink that fills the printer can include the polymer, a bioactive agent, bone material or a combination therefore used to manufacture the bone graft. For example, osteogenic material including, in some cases, a polymer that preserves the biological activity of demineralized bone particles and/or fibers can be supplied to form ink that can be used in steps 720, 722, 724 and 726. In step 724, the computer may first check to determine if the final layer has printed all the layers required to produce the custom bone graft. These layers may have been provided by a programmed module operative on a digital data processing device, and may be the 3-D model of the custom bone graft reduced to consecutive slices that when printed in the correct order, may result in the desired bone graft.

In step 726, the 3-D printer may print the next layer if the final layer has not yet been printed. This may be done, for instance, by moving the print nozzle in a raster fashion, depositing ink where required. The printing may be performed in a sterilized environment.

In step 728, once the 3-D printer has printed all the required layers that constitute the custom bone graft, the bone graft may undergo post print processing. This post processing step may, for instance, include actions such as, but not limited to, dissolving out the sucrose crystals, if any are present, to provide a porous structure and sterilization of the custom bone graft.

Layered 3-D Printed Bone Graft

In certain embodiments, the computer implemented method described herein provides a layered 3-D printed bone graft. In some implementations, the 3-D printed bone graft includes a first layer of biodegradable polymer followed by a second layer of bone material disposed on the first layer of biodegradable polymer, which is followed by a third layer of biodegradable polymer disposed on the second layer, each layer repeating until a 3-D printer has completed the layered bone graft. In other embodiments, the 3-D printed bone graft includes a first layer of biodegradable polymer mixed with bone material, a second layer of biodegradable polymer mixed with bone material, the second layer disposed on the first layer, a third layer of biodegradable polymer mixed with bone material, the third layer disposed on the second layer, each layer repeating until the 3-D printer has completed the layered bone graft.

As discussed above in connection with the computer implemented method for producing the customized bone graft of this disclosure, in some embodiments, the bone material of the bone graft comprises (i) mineralized allograft and non-demineralized allograft or a combination thereof, or (ii) allograft, demineralized bone matrix fiber and demineralized bone chips or a combination thereof. In other embodiments, the layered 3-D printed bone graft contains bone material which comprises (i) fully demineralized bone fibers and surface demineralized bone chips, or (ii) a demineralized bone matrix material comprising fully demineralized bone matrix fibers and surface demineralized bone chips in a ratio of from about 25:75 to about 75:25.

Figure 13:
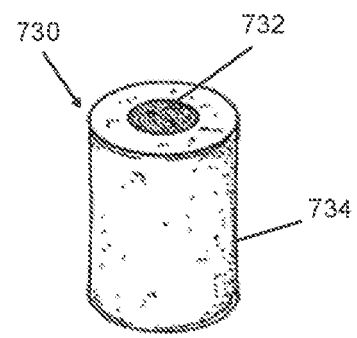
FIG. 13 illustrates an embodiment of a 3-D printed bone graft that is custom made to fit in the intended bone graft site.

FIG. 13 illustrates an embodiment of a 3-D printed bone graft that is custom made to fit in the intended bone graft site. In FIG. 13, a 3-D printed substantially cylindrically shaped bone graft 730 is shown, which contains bone material 732 that is partially enclosed by a container 734 made from a biodegradable polymer. This 3-D printed substantially cylindrically shaped bone graft 730 can be made using two print heads coupled to the computer system described above, where one print head contains the bone material 732 and the other print head contains the biodegradable polymer used to make the container 734. First, the first print head can print the container 734 made from the biodegradable polymer and then the second print head can print the bone material 732 (e.g., DBM particles) to fill the container 734 to make the substantially cylindrically shaped bone graft 730. The substantially cylindrically shaped bone graft 730 is generated from a 3-D digital model of an intended bone graft site, which is generated based on a 3-D image of the intended bone graft site (e.g., X-ray, CT image, MRI, etc.). The 3-D digital model of the intended bone graft site includes a virtual depth, thickness and volume of the bone graft site, the 3-D digital model of the bone graft being configured to fit within the 3-D digital model of the intended bone graft site. The 3-D digital models of the bone graft and the intended bone graft site are stored on the computer, and the computer system will retrieve the stored 3-D digital model of the bone graft. When instructed, the computer will print the carrier material (e.g., which can be a biodegradable polymer, a bioactive agent or a combination thereof in a mixture) as the container 734. The computer will then print the bone material 732 to form the substantially cylindrically shaped bone graft 730.

Figure 14:
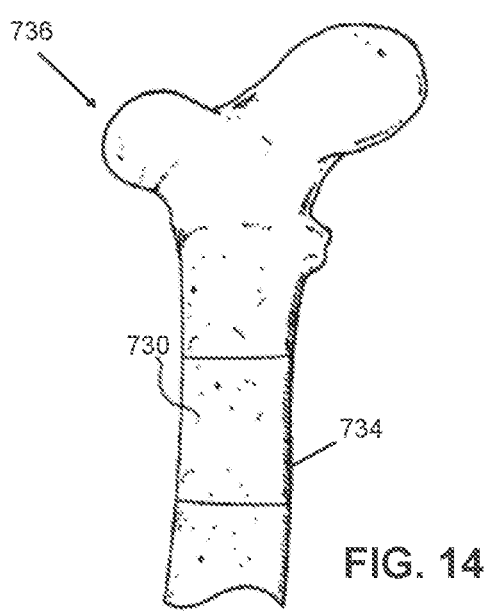
FIG. 14 illustrates a view of a human femur showing a 3-D printed bone graft of the present application that is implanted into the intended bone graft site.

FIG. 14 illustrates a view of a human femur 736 showing a 3-D printed bone graft of the present application that is implanted into the intended bone graft site. In FIG. 14, the intended bone graft site is a substantially cylindrical bone defect in the human femur 736. The 3-D printed substantially cylindrically shaped bone graft 730, which contains bone material that is partially enclosed by a container 734 made from a biodegradable polymer is shown implanted into the bone defect in the human femur 736. In this way, the bone graft can be printed to match the specific shape of the bone defect to have a bone graft custom made based on the bone defect. This can eliminate the need to specifically shape the bone graft to the intended bone graft site. In addition, it can eliminate the need to shape the bone defect to a desired shape by drilling or creating a bone cavity to match the shape of the implant.

In some embodiments, a variety of shapes and sizes of the 3-D digital model can be provided to the user, which will allow the user to select from a library of stored 3-D digital models of the bone graft based on the 3-D digital models of the intended bone graft site. The computer will perform the desired matching routine to match the intended bone graft site with the bone graft. In some embodiments, the computer will provide the preferred 3-D digital model of the bone graft with a 99.9% confidence interval that the user can select. Alternatively, the user can select a bone graft that can be printed that can be molded by the clinician and then implanted. However, the implant will have the desired volume based on the 3-D digital model.

Figure 15:
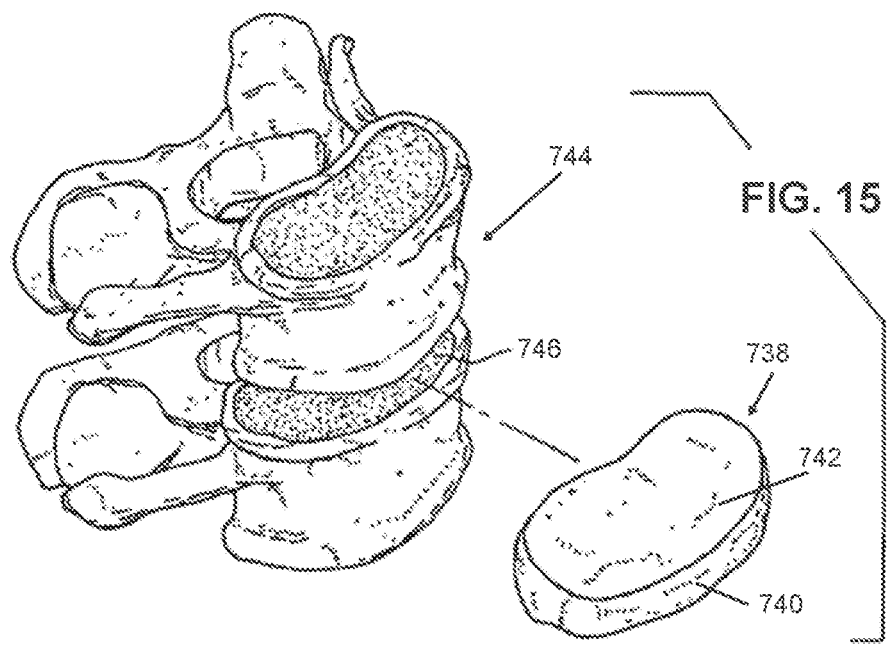
FIG. 15 illustrates a partial view of the human vertebral column showing a 3-D printed disc-shaped bone graft of the present application being implanted at an intended bone graft site, which is an intervertebral site.

FIG. 15 illustrates a partial view of the human vertebral column 744 showing a 3-D printed disc-shaped bone graft 738 of the present application being implanted at an intended bone graft site, which is an intervertebral site 746. In FIG. 15, the 3-D printed disc-shaped bone graft 738 contains bone material 740 that surrounds a polymer 742 of the implant. This 3-D printed disc-shaped bone graft 738 will mimic a natural vertebra as the polymer 742 will mimic the jelly like consistency of the nucleus pulpous and the bone material 740 will surround the polymer 742. Therefore, the disc-shaped bone graft 738 can be made using two print heads coupled to the computer system described above, where one print head contains the bone material 740 and the other print head contains the polymer 742 used to make the disc-shaped bone graft 738. First, the first print head can print the bone material 740 loaded in the printer in the shape of disc-shaped bone graft 738 and then the second print head can print the polymer 742 inside the bone material 740 to make the disc-shaped bone graft 738. The disc-shaped bone graft 738 is generated from a 3-D digital model of an intended bone graft site, which is generated based on a 3-D image of the intended bone graft site (e.g., X-ray, CT image, MRI, etc.). The 3-D digital model of the intended bone graft site includes a virtual depth, thickness and volume of the intended bone graft site. The 3-D digital model of the bone graft being configured to fit within the 3-D digital model of the intended bone graft site. The 3-D digital models of the bone graft and the intended bone graft site are stored on the computer and the computer system will retrieve the stored 3-D digital model of the bone graft once instructed and print the bone material 740 (e.g., bone particles in a binder) and then print the polymer 742 inside the bone material 740 to form the disc-shaped bone graft 738.

In various embodiments, as described above, the polymer of the carrier material comprises a curable biocompatible and/or biodegradable polymer. In these embodiments, the biodegradable polymer comprises at least one of poly(lactic acid), poly(glycolic acid), poly(lactic acid-glycolic acid), polydioxanone, PVA, polyurethanes, polycarbonates, polyhydroxyalkanoates (polyhydroxybutyrates and polyhydroxyvalerates and copolymers), polysaccharides, polyhydroxyalkanoates, polyglycolide-co-caprolactone, polyethylene oxide, polypropylene oxide, polyglycolide-co-trimethylene carbonate, poly(lactic-co-glycolic acid) or combinations thereof. In other embodiments, the biodegradable polymer further comprises at least one of a polymer sugar, protein, hydrophilic block copolymer, hyaluronic acid, polyuronic acid, mucopolysaccharide, proteoglycan, polyoxyethylene, surfactant, polyhydroxy compound, polyhydroxy ester, fatty alcohol, fatty alcohol ester, fatty acid, fatty acid ester, liquid silicone, or combinations thereof.

In some uses, the carrier acts as a temporary scaffold until replaced by new bone. Polylactic acid (PLA), polyglycolic acid (PGA), and various combinations have different dissolution rates in vivo. In bone, the dissolution rates can vary according to where the bone allograft is placed.

Figure 16:
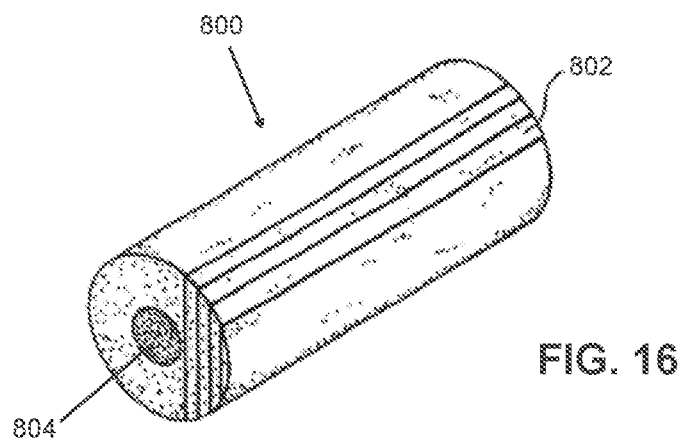
FIG. 16 illustrates a cross-sectional view of a 3-D printed bone graft of the current application that has allograft tissue partially enclosed by layers of polymers that is custom made to fit in the intended bone graft site.

FIG. 16 illustrates a cross-sectional view of a 3-D printed bone graft 800 of the current application that is substantially cylindrically shaped and has allograft tissue particles 804 partially enclosed by layers of polymers 802 that are custom made to fit in the intended bone graft site.

Figure 17:
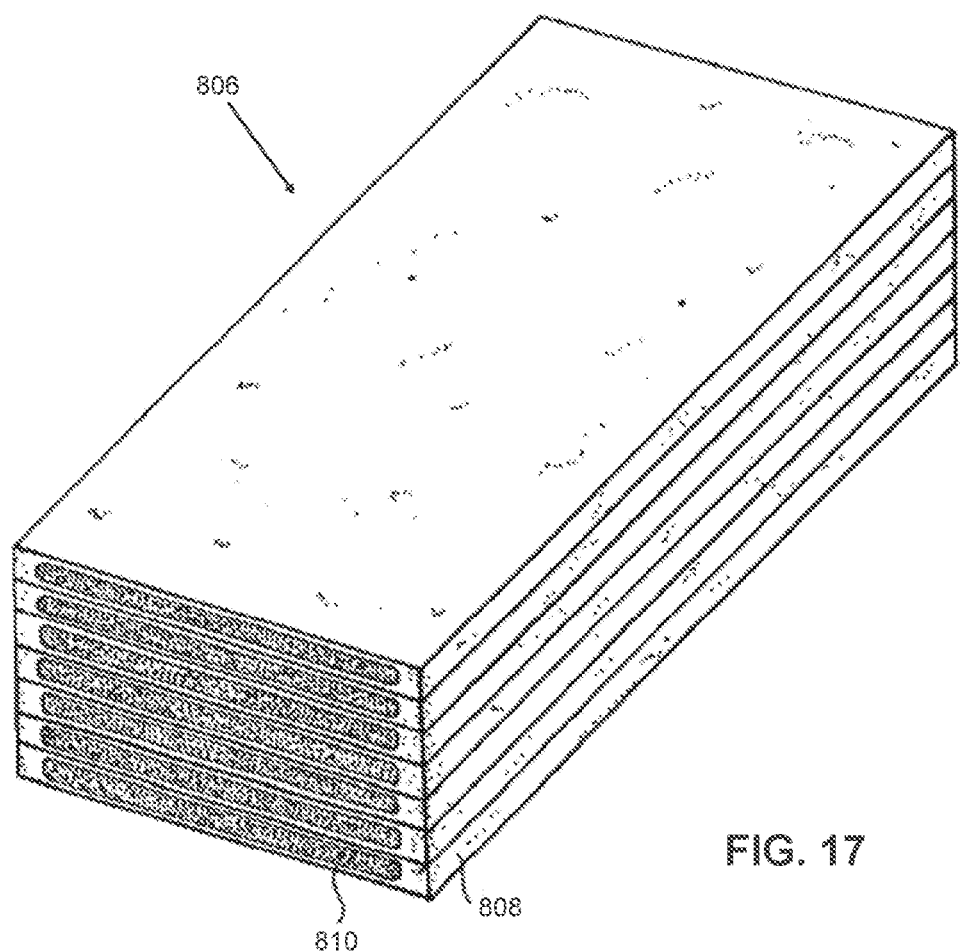
FIG. 17 illustrates an enlarged perspective view of a 3-D printed bone graft of the current application that has allograft tissue partially enclosed by layers of polymers that form strips that are custom made to fit in the intended bone graft site.

FIG. 17 illustrates an enlarged perspective view of a 3-D printed bone graft 806 of the current application that has allograft tissue particles 810 partially enclosed by layers of polymers that form strips 808 that are custom made to fit in the intended bone graft site. These strips 808 can be printed with varying widths, sizes and shapes. It will be understood that the ink or carrier used to print the bone graft can have the polymer, bioactive agent, and/or bone material combined in one carrier or ink to be delivered to one print head or be in separate inks or carriers and in separate print heads where the computer will instruct the print heads to print the bone graft.

The layered 3-D printed bone grafts obtained by the computer implemented method described herein are useful in many applications, including without limitations, in oral maxillofacial surgery, dental implants, orthopedic surgery or any type of reconstructive hard tissue surgery, in some instances, in cortical or trabecular bone. In clinical use, the layered 3-D printed bone grafts of this application allow not only for customizing to accommodate the anatomy of an individual patient, but also, in some embodiments, can successfully be used to release a specific drug from the bone graft to an intended bone repair site.

Accordingly, in some implementations, this application also provides a method of treating a bone defect in a patient, the method comprising administering a layered 3-D printed bone graft to the intended bone defect, wherein the layered 3-D printed bone graft comprises a first layer of biodegradable polymer; a second layer of bone material disposed on the first layer of biodegradable polymer; a third layer of biodegradable polymer disposed on the second layer, each layer repeating until a 3-D printer has completed the layered bone graft. In other implementations, the method of treatment comprises administering a layered 3-D printed bone graft to the intended bone defect, wherein the layered 3-D printed bone graft comprises a first layer of biodegradable polymer mixed with bone material; a second layer of biodegradable polymer mixed with bone material, the second layer disposed on the first layer; a third layer of biodegradable polymer mixed with bone material, the third layer disposed on the second layer, each layer repeating until the 3-D printer has completed the layered bone graft. In various embodiments, the layered 3-D printed bone grafts described in this disclosure can be useful in treating bone defects caused by osteomyelitis or bone cancer.

In certain embodiments, when the 3-D printed bone graft is a mesh bag, any suitable method may be used for loading a bone material into mesh bag 70. In some embodiments, the bone material may be spooned into the mesh bag, placed in the mesh bag body using forceps, loaded into the mesh bag using a syringe (with or without a needle), or inserted into the mesh bag in any other suitable manner including using automation.

For placement, the substance or substances may be provided in the mesh bag and placed in vivo, for example, at a bone defect. In one embodiment, the mesh bag is placed in vivo by placing the mesh bag in a catheter or tubular inserter and delivering the mesh bag with the catheter or tubular inserter. The mesh bag, with a substance provided therein, may be steerable such that it can be used with flexible introducer instruments for, for example, minimally invasive spinal procedures. For example, the bone graft may be introduced down a tubular retractor or scope, during XLIF, TLIF, or other procedures.

In clinical use, a delivery system comprising a mesh implant and delivered substance may be used in any type of spinal fusion procedure including, for example, posterolateral fusion, interbody fusion (of any type), facet fusion, spinous process fusion, anterior only fusion, or other fusion procedure. Examples of such spinal procedures include posterior lumbar interbody fusion (PLIF), anterior lumbar fusion (ALIF) or posterior cervical or cervical interbody fusion approaches. In some embodiments, the mesh bag useful with TLIF, ALIF or XLIF procedures may be tubular and have dimensions of approximately 2.5 cm in length and approximately 0.5 cm in width. In other ALIF procedures, a mesh bag of approximately 1 cm by 1 cm can be used. In various embodiments, the mesh bags may be tubular and may have dimensions of approximately 5 mm to approximately 10 mm long and approximately 0.5 cm to 1 cm wide. In other embodiments, the mesh implant or bag (with or without substance loaded) may be placed in a cage, for example, for interbody fusion.

In some embodiments, the 3-D printed mesh bag may be prefilled with a substance for delivery and other compartments may be empty for filling by the surgeon. In some embodiments, the 3-D mesh bag comprises a first and a second compartment. In other embodiments, the first and second compartments of the 3-D mesh bag are in communication with each other. In several embodiments, one compartment may be bone filled while the other compartment of the 3-D mesh bag is not. In various embodiments, the 3-D printed seamless mesh bag conforms to surrounding bony contours when implanted in vivo.

The mesh bag may be used in any suitable application. In some embodiments, the mesh bag may be used in healing vertebral compression fractures, interbody fusion, minimally invasive procedures, posterolateral fusion, correction of adult or pediatric scoliosis, treating long bone defects, osteochondral defects, ridge augmentation (dental/craniomaxillofacial, e.g., edentulous patients), beneath trauma plates, tibial plateau defects, filling bone cysts, wound healing, around trauma, contouring (cosmetic/plastic/reconstructive surgery), and others. The mesh bag may be used in a minimally invasive procedure via placement through a small incision, via delivery through a tube, or other means. The size and shape may be designed with restrictions on delivery conditions.

In some embodiments, the mesh bag is flexible enough so that it can be folded upon itself before it is implanted at, near, or in the bone defect.

An exemplary application for using a mesh bag as disclosed is fusion of the spine. In clinical use, the mesh bag and delivered substance may be used to bridge the gap between the transverse processes of adjacent or sequential vertebral bodies. The mesh bag may be used to bridge two or more spinal motion segments. The mesh bag surrounds the substance to be implanted, and contains the substance to provide a focus for healing activity in the body.

Generally, the mesh implant or bag may be applied to a pre-existing defect, to a created channel, or to a modified defect. Thus, for example, a channel may be formed in a bone, or a pre-existing defect may be cut to form a channel, for receipt of the device. The mesh implant or bag may be configured to match the channel or defect. In some embodiments, the configuration of the mesh bag may be chosen to match the channel. In other embodiments, the channel may be created, or the defect expanded or altered, to reflect a configuration of the mesh bag. The mesh bag may be placed in the defect or channel and, optionally, coupled using attachment mechanisms.

Although the invention has been described with reference to certain embodiments, persons skilled in the art will recognize that changes may be made in form and detail without departing from the spirit and scope of the invention.

What is claimed is:

1. A computer implemented method for producing a bone graft, the method comprising:
    obtaining a 3-D image of an intended bone graft site, the 3-D image being a computed tomography image of an unhealthy bone graft site based on a 3-D scan of a healthy bone graft site;
    generating a 3-D digital model of the intended bone graft site based on the 3-D image of the intended bone graft site, the 3-D digital model of the bone graft site including a virtual depth, thickness and volume of the intended bone graft site;
    generating a 3-D digital model of the bone graft based on the 3-D digital model of the intended bone graft site, the 3-D digital model of the bone graft including a virtual depth, thickness and volume of the bone graft, the 3-D digital model of the bone graft being configured to fit within the 3-D digital model of the intended bone graft site;
    storing the 3-D digital model of the bone graft on a database coupled to a processor, the processor having instructions for (a) retrieving the stored 3-D digital model of the bone graft; (b) combining a carrier material with, in or on a bone material based on the stored 3-D digital model of the bone graft, the carrier material comprises a curable ink containing microspheres having diameters from about 1 µm to about 750 µm in size; and (c) instructing a 3-D printer having a rotatable cylindrical body to print the complete bone graft having the carrier material around a circumference and along a longitudinal axis of the rotatable cylindrical body by continuous extrusion and rotation such that the 3-D printer has a rotatable printing surface corresponding to a lateral surface area of the rotatable cylindrical body;

printing the bone graft which is a mesh bag customized to the intended bone graft site, wherein the bone graft is produced by instructing the 3-D printer to print the carrier material and then print the bone material in or on the carrier material based on the stored 3-D digital model of the bone graft;

filling the mesh bag with a second bone material;

calculating a volume, a length, a width, and a thickness of a covering to match a volume, a length, a width, and a thickness of the mesh bag;

generating a covering for enclosing the bone material within the mesh bag; and printing the complete bone graft including the mesh bag and the covering customized to the intended bone graft site.

2. The computer implemented method of claim 1, wherein the carrier material comprises a metal, a biodegradable polymer or a combination thereof, and the bone material comprises mineralized or demineralized bone.

3. The computer implemented method of claim 1, wherein the bone material comprises allograft, demineralized bone matrix fiber, demineralized bone chips or a combination thereof.

4. The computer implemented method of claim 1, wherein the bone material comprises (i) fully demineralized bone fibers and surface demineralized bone chips; or (ii) fully demineralized bone matrix fibers and surface demineralized bone chips in a ratio of from about 25:75 to about 75:25.

5. The computer implemented method of claim 1, wherein the 3-D image is obtained from (i) one or more X-ray images; (ii) a computer aided design (CAD) program; (iii) a cone beam imaging device; (iv) a computed tomography (CT) scan device; and/or (v) a magnetic resonance imaging (MRI).

6. The computer implemented method of claim 1, wherein the carrier material further comprises a drug, a growth factor, a protein or a combination thereof.

7. The computer implemented method of claim 6, wherein the drug, the growth factor, or the protein is disposed in microspheres or beads in the carrier material.

8. The computer implemented method of claim 7, wherein the microspheres are porous.

9. The computer implemented method of claim 1, wherein the carrier material comprises an ink that dries, is cured or reacts to form a porous, biodegradable, biocompatible material that is osteoinductive and has a load bearing strength comparable to bone.

10. The computer implemented method of claim 1, wherein the bone material comprises microparticles or nanoparticles varying from about 10 nm to about 500 nm.

11. The computer implemented method of claim 1, wherein the bone graft has a cross-sectional shape corresponding to the cross-sectional shape of the rotatable printing surface.

* * * * *